(12) United States Patent
Kundu et al.

(10) Patent No.: US 9,470,691 B2
(45) Date of Patent: Oct. 18, 2016

(54) APPLICATION OF REDUCED DYES IN IMAGING

(71) Applicant: LI-COR, INC., Lincoln, NE (US)

(72) Inventors: Kousik Kundu, Lincoln, NE (US); Nisha Padhye, Lincoln, NE (US); William Volcheck, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 151 days.

(21) Appl. No.: 14/192,827

(22) Filed: Feb. 27, 2014

(65) Prior Publication Data

US 2014/0213473 A1 Jul. 31, 2014

Related U.S. Application Data

(63) Continuation of application No. PCT/US2012/056739, filed on Sep. 21, 2012.

(51) Int. Cl.

| A61K 51/00 | (2006.01) |
| A61M 36/14 | (2006.01) |
| G01N 33/58 | (2006.01) |
| C07D 209/08 | (2006.01) |
| C09B 23/01 | (2006.01) |
| C09B 23/08 | (2006.01) |

(52) U.S. Cl.
CPC ............ *G01N 33/582* (2013.01); *C07D 209/08* (2013.01); *C09B 23/0008* (2013.01); *C09B 23/0025* (2013.01); *C09B 23/0066* (2013.01); *C09B 23/083* (2013.01); *C09B 23/086* (2013.01)

(58) Field of Classification Search
CPC C07D 209/08; C07D 23/008; C07D 23/025; C07D 23/0066; C07D 23/083; C07D 207/30; C07D 209/44; C07D 209/04; G01N 33/582; C09B 23/008; C09B 23/025; C09B 23/0066; C09B 23/083
USPC .............. 424/1.11, 1.65, 1.81, 9.1, 9.3, 9.6; 548/460, 470, 560

See application file for complete search history.

(56) References Cited

U.S. PATENT DOCUMENTS

| 3,916,069 | A | 10/1975 | Tiers et al. |
| 5,268,486 | A | 12/1993 | Waggoner et al. |
| 5,486,616 | A | 1/1996 | Waggoner et al. |
| 5,569,587 | A | 10/1996 | Waggoner |
| 5,569,766 | A | 10/1996 | Waggoner et al. |
| 5,627,027 | A | 5/1997 | Waggoner |
| 6,051,531 | A | 4/2000 | Noonan et al. |
| 9,089,603 | B2 * | 7/2015 | Xu ............... A61K 49/0032 |
| 2004/0014981 | A1 | 1/2004 | Lugade et al. |
| 2005/0130059 | A1 | 6/2005 | Tao |
| 2007/0083048 | A1 | 4/2007 | Chichiishi et al. |
| 2009/0263327 | A1 | 10/2009 | Achilefu et al. |
| 2010/0274023 | A1 | 10/2010 | Callant et al. |
| 2010/0323389 | A1 | 12/2010 | Xu et al. |
| 2011/0070166 | A1 | 3/2011 | Murthy et al. |

FOREIGN PATENT DOCUMENTS

| WO | 2009/121055 A1 | 10/2009 |
| WO | 2012/061403 A1 | 5/2012 |

OTHER PUBLICATIONS

Extended European Search Report, Apr. 16, 2015, EP Application No. 12833163, 8 pages.
Choi et al., "Synthesis and In Vivo Fate of Zwitterionic Near-Infrared Fluorophores," Angew. Chem. Int. Ed., 2011, vol. 50, pp. 1-7 (final page Nos. 6258-6263).
Selvam et al., "Minimally invasive, longitudinal monitoring of biomaterial-associated inflammation by fluorescence imaging," Biomaterials, 2011, vol. 32, pp. 7785-7792.
PCT application No. PCT/US2010/2056739, International Search Report, Jan. 22, 2013, 3 pages.

* cited by examiner

*Primary Examiner* — D L Jones
(74) *Attorney, Agent, or Firm* — Kilpatrick Townsend & Stockton LLP

(57) ABSTRACT

The present invention provides novel compounds and methods for hydrocyanines derived from near-infrared cyanine dyes, as reactive oxygen species probes in imaging. In certain embodiments, the present invention provides reduced dyes as substrates for ELISA and Western blots.

13 Claims, 12 Drawing Sheets

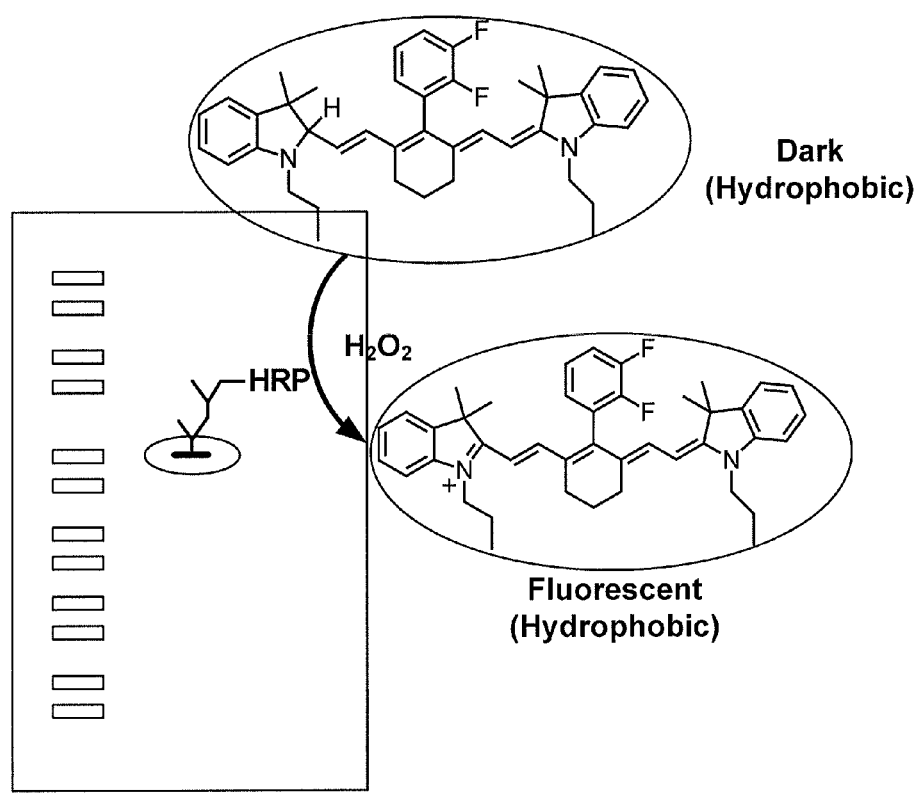
Fig. 14
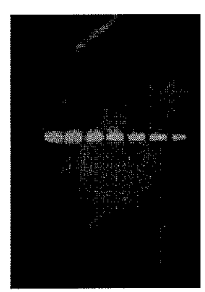
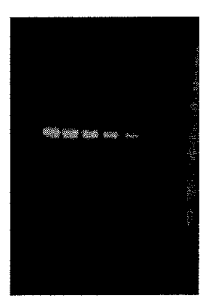
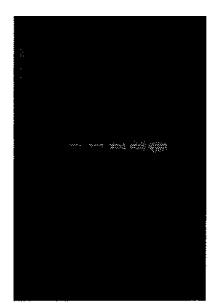
FIG. 15A     FIG. 15B     FIG. 15C     FIG. 15D

APPLICATION OF REDUCED DYES IN IMAGING

CROSS-REFERENCES TO RELATED APPLICATIONS

This application is a continuation of PCT/US2012/056739 filed Sep. 21, 2012, which application claims priority to U.S. Provisional Application No. 61/538,771, filed on Sep. 23, 2011; U.S. Provisional Application No. 61/570,772, filed Dec. 14, 2011; and U.S. Provisional Application No. 61/597,677, filed Feb. 10, 2012, the disclosures of which are hereby incorporated by reference in their entireties for all purposes.

BACKGROUND OF THE INVENTION

Cyanine dyes have been widely used for labeling ligands or biomolecules for a variety of applications such as DNA sequencing. (See, for example, U.S. Pat. No. 5,571,388 for exemplary methods of identifying strands of DNA by means of cyanine dyes.) More recently, they have been used for optical imaging of dye-labeled biomolecules, either in vivo or in vitro. (See, for example, U.S. Pat. No. 7,597,878.) Scientists favor using cyanine dyes in biological applications because, among other reasons, many of these dyes fluoresce in the near-infrared (NIR) region of the spectrum (600-1000 nm). This makes cyanine dyes less susceptible to interference from autofluorescence of biomolecules.

Other advantages of cyanine dyes include, for example: 1) cyanine dyes strongly absorb and fluoresce light; 2) many cyanine dyes do not rapidly bleach under a fluorescence microscope; 3) cyanine dye derivatives can be made that are effective coupling reagents; 4) many structures and synthetic procedures are available, and the class of dyes is versatile; and 5) cyanine dyes are relatively small (a typical molecular weight is about 1,000 daltons), so they do not cause appreciable steric interference in a way that might reduce the ability of a labeled biomolecule to reach its binding site or carry out its function.

Hydrocyanines and deuterocyanines are a reduced form of cyanine dyes. Because of the disrupted p-conjugation, they are essentially nonfluorescent molecules. In the presence of radicals, hydrocyanines or deuterocyanines oxidize back to the fluorescent cyanine dyes.

Hydrocyanine and deuterocyanine dye precursors are needed for use in labeling biomolecules as well as in vivo imaging for the diagnosis and prognosis of diseases such as cancer. Such compositions and methods are needed for aiding in the analysis of responses to various therapies. The present invention satisfies these and other needs.

BRIEF SUMMARY OF THE INVENTION

The present invention provides compounds, methods, assays and systems relating to hydrocyanine or deuterocyanine dyes. In certain instances, the compounds are useful for detecting reactive oxygen species (ROS) probes for in vivo applications.

As such, in one embodiment, the present invention provides a compound of Formula I:

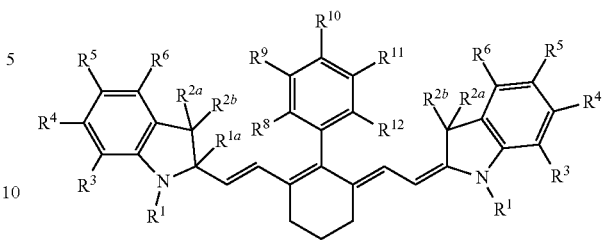

wherein
each $R^1$ is an independently selected alkyl group that is additionally substituted with from 0 to 1 $R^{14}$ and from 0 to 1 -L-Y—Z; wherein the alkyl is optionally interrupted by at least one heteroatom;
$R^{1a}$ is either hydrogen or deuterium;
each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 -L-Y—Z;
each $R^3$, $R^4$, $R^5$, and $R^6$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 -L-Y—Z;
$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein at least one member selected from the group consisting of $R^8$, $R^9$, and $R^{10}$ is halo;
each $R^{13}$ is a member independently selected from the group consisting of hydroxyl, amino, carboxyl, and alkoxycarbonyl;
each $R^{14}$ is a member independently selected from the group consisting of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the alkyl or alkenyl is additionally substituted with from 0 to 1 $R^{13}$ and from 0 to 1 -L-Y—Z;
each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;
each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;
each Z is independently selected from the group consisting of -L-R$^{13}$ and -L-R$^{16}$;
or alternatively, —Y—Z is a member selected from the group consisting of —N(Z)$_2$, —N(Z)C(O)Z, and —C(O)N(Z)$_2$, and the two Z groups may optionally be linked to form a cycloalkynyl group;

each $R^{15}$ is a member independently selected from the group consisting of alkyl and alkoxycarbonylalkyl; wherein the alkyl is optionally interrupted by at least one heteroatom;

each $R^{16}$ is independently a member selected from the group consisting of activated acyl, acrylamido, optionally substituted alkylsulfonate ester, azido, optionally substituted arylsulfonate ester, optionally substituted amino, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, cycloalkynyl, cycloalkynylcarbonyl, spirocycloalkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester; and wherein the compound has a balanced charge.

In another embodiment, the present invention provides a compound of Formula II:

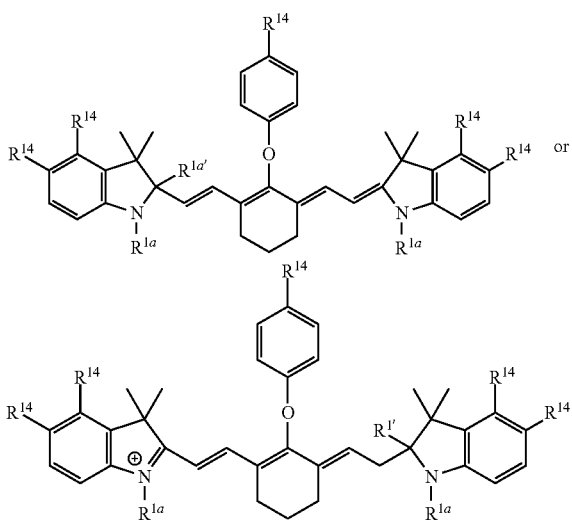

wherein:

$R^1$ and $R^{1a}$ are each independently an alkyl group that is additionally substituted with from 0 to 1 $R^{13}$, wherein the alkyl is optionally interrupted by at least one heteroatom;

$R^{1a\prime}$ and $R^{10}$ are each independently either hydrogen or deuterium;

each $R^{13}$ is independently a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl;

each $R^{14}$ is a member independently selected from the group of alkyl, alkenyl, halo, hydrogen, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 1 $R^{13}$; and wherein at least one $R^{14}$ is sulfonato;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —$NR^{15}$—, —$NR^{15}$C(O)—, —C(O)$NR^{15}$—, —NZ—, —NZC(O)—, and —C(O)NZ—; each Z is an independently selected $C_1$-$C_{10}$ alkyl that is additionally substituted with one member from the group of $R^{13}$ and $R^{16}$; wherein the alkyl is optionally interrupted by at least one heteroatom.

In still another embodiment, the present invention provides a compound of Formula III:

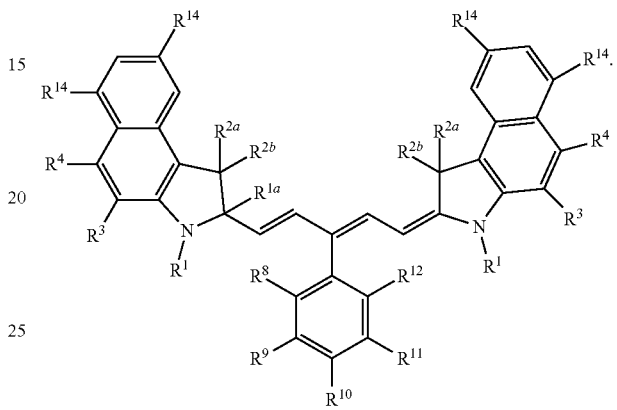

wherein $R^1$ is an alkyl group that is additionally substituted with from 0 to 1 $R^{13}$, and wherein the alkyl group is optionally interrupted by at least one heteroatom;

$R^{1a}$ is either hydrogen or deuterium;

$R^{2a}$ and $R^{2b}$ are each a member independently selected from the group of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl;

$R^3$ and $R^4$ are each a member independently selected from the group of hydrogen, alkyl, alkenyl, halo, hydroxyl, alkoxy, cyano, carboxyl, alkoxycarbonyl, amido, amino, sulfonato, alkoxyalkyl, carboxyalkyl, alkoxycarbonylalkyl, and sulfonatoalkyl;

$R^8$ and $R^9$ are each a member independently selected from the group of hydrogen, alkyl, alkenyl, halo, alkoxy, sulfonato, and -L-Y—Z, wherein exactly one member selected from the group of $R^8$ and $R^9$ is -L-Y—Z;

$R^{10}$, $R^{11}$, and $R^{12}$ are each a member independently selected from the group of hydrogen, alkyl, alkenyl, halo, alkoxy, and sulfonato;

each $R^{13}$ is a member independently selected from the group of hydroxyl, amino, carboxyl, alkoxycarbonyl, amido, sulfonato, and thioacetyl;

each $R^{14}$ is a member independently selected from the group of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 1 $R^{13}$;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —$NR^{15}$—, —$NR^{15}$C(O)—, —C(O)$NR^{15}$—, —NZ—, —NZC(O)—, and —C(O)NZ—;

each Z is an independently selected $C_1$-$C_{10}$ alkyl that is additionally substituted with one member from the group of $R^{13}$ and $R^{16}$; wherein the alkyl is optionally interrupted by at least one heteroatom;

$R^{15}$ is a member selected from the group of alkyl and alkoxycarbonylalkyl; wherein the alkyl is optionally interrupted by at least one heteroatom; and each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl.

In still yet another embodiment, the present invention provides a compound of Formula IVa or IVb:

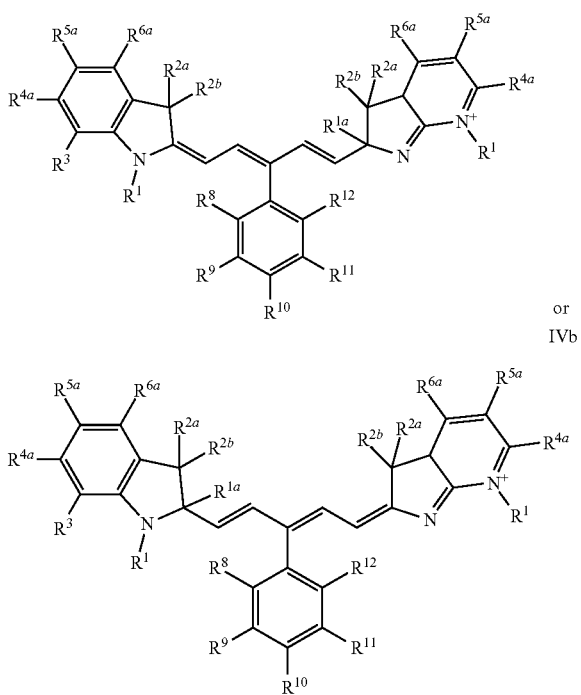

wherein
each $R^1$ is a member selected from the group consisting of L-Y—Z and an alkyl group that is additionally substituted with from 0 to 1 $R^{13}$ and from 0 to 1 $R^{16}$, and wherein the alkyl is optionally interrupted by at least one heteroatom;

$R^{1a}$ is either hydrogen or deuterium;

each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 $R^{16}$;

each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl, wherein a carbon of the member is additionally substituted with from 0 to 1 $R^{16}$;

$R^8$, $R^9$, $R^{10}$, $R^{11}$ and $R^{12}$ are each a member independently selected from the group consisting of hydrogen, alkyl, alkenyl, halo, alkoxy, sulfonato, sulfonatoalkyl, hydroxyl, amino, carboxyl, alkoxycarbonyl, cyano, amido, thioacetyl, and -L-Y—Z; wherein, at least one member selected from the group consisting of $R^8$, $R^9$, and $R^{10}$ is -L-Y—Z;

each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;

each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;

each Z is independently selected from the group consisting of -L-R$^{13}$ and -L-R$^{16}$;

each $R^{13}$ is a member independently selected from the group of hydroxyl, amino, carboxyl, alkoxycarbonyl, amido, sulfonato, and thioacetyl;

each $R^{15}$ is a member independently selected from the group consisting of alkyl and alkoxycarbonylalkyl; wherein the alkyl is optionally interrupted by at least one heteroatom;

each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido, a pegylated alkynyl, a pegylated cycloalkynyl, an ortho substituted phosphinyl aryl ester (e.g., TPPME), a spirocycloalkynyl, and an ortho substituted phosphine oxide aryl ester.

In still yet another embodiment, the present invention provides a compound of Formula V:

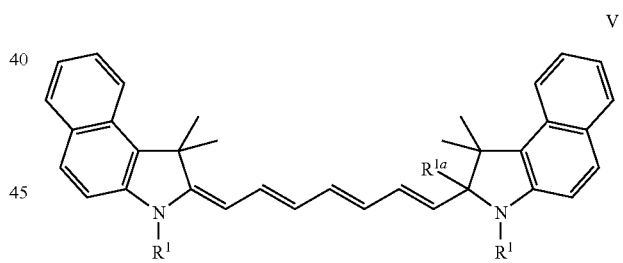

wherein:
each $R^1$ is a member selected from the group consisting of L-Y—Z and an alkyl group that is additionally substituted with from 0 to 1 $R^{13}$ and from 0 to 1 $R^{16}$, wherein the alkyl is optionally interrupted by at least one heteroatom;

$R^{1a}$ is either hydrogen or deuterium;

each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —NR$^{15}$—, —NR$^{15}$C(O)—, —C(O)NR$^{15}$—, —NZ—, —NZC(O)—, and —C(O)NZ—;

each Z is an independently selected $C_1$-$C_{10}$ alkyl that is additionally substituted with one member from the group of $R^{13}$ and $R^{16}$; wherein the alkyl is optionally interrupted by at least one heteroatom;

$R^{15}$ is a member selected from the group of alkyl and alkoxycarbonylalkyl, wherein the alkyl is optionally interrupted by at least one heteroatom; and each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl.

These and other objects, advantages and embodiments will become more apparent when read with the accompanying figures and detailed description which follow.

BRIEF DESCRIPTION OF THE DRAWINGS

FIG. 14 shows a schematic representation of the immunoassay methods of the present invention.

FIG. 15 A-D show the immunoassay analysis of cell lysates using various fluorescent probes. 4-12% Bis-Tris gels were loaded A431 lysate samples, electrophoresed, transferred to nitrocellulose membranes, and blocked. The blots were probed with mouse anti-β actin antibodies followed by HRP goat anti-mouse antibodies (FIGS. 15A-B) or cyanine-antibody conjugates (FIGS. 15C-D). FIGS. 15A-B were incubated for 5 min with chemifluorescent substrate after antibody binding: (FIG. 15A) 10 μM H-IR780F2 (200 μM $H_2O_2$, pH 5.0 Citrate buffer); (FIG. 15B) HRP 680 ELISA substrate (LI-COR). FIG. 15C and FIG. 15D were incubated with IRDye 800CW GAM and IRDye 680RD GAM, respectively, after binding of mouse anti-α actin antibodies.

DETAILED DESCRIPTION

I. Definitions

Figure 1:
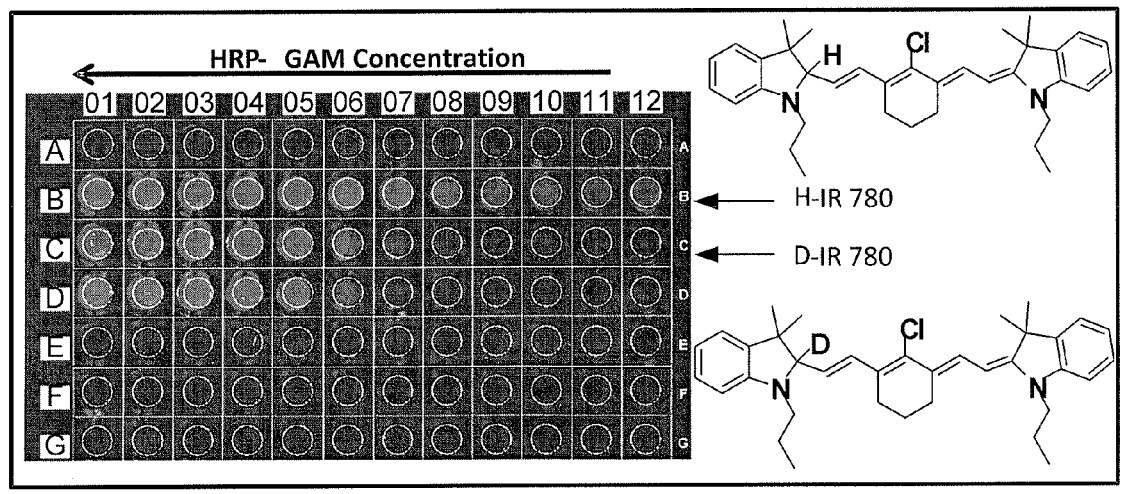
FIG. 1 demonstrates the usefulness of the hydrocyanine dye analog to IRIR-780780 as an HRP substrate. The wells from 01 to 12 show the fluorescence with decreasing HRP-enzyme concentrations (from 800 nM to 0.8 nM).

The terms "a," "an," or "the" as used herein not only include aspects with one member, but also include aspects with more than one member. For example, an embodiment of a method of imaging that comprises using a compound set forth herein would include an aspect in which the method comprises using two or more compounds set forth herein.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 700 to 850 nm" is equivalent to "from about 700 nm to about 850 nm." When "about" is applied to describe the first value of a set of values, it applies to all values in that set. Thus, "about 680, 700, or 750 nm" is equivalent to "about 680 nm, about 700 nm, or about 750 nm." However, when the modifier "about" is applied to describe only the end of the range or only a later value in the set of values, it applies only to that value or that end of the range. Thus, the range "about 2 to 10" is the same as "about 2 to about 10," but the range "2 to about 10" is not.

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride or mixed anhydride —OC(O)R$^a$ or —OC(NR$^a$)NHR$^b$, wherein R and R$^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, N-morpholinoethyl or aryl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl (—$OC_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy). Preferred activated esters include succinimidyloxy and sulfosuccinimidyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double bond. Preferred alkenyl groups have 2 to about 12 carbon atoms. More preferred alkenyl groups contain 2 to about 6 carbon atoms. "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, and the like.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH=CH—, —$CH_2$—CH=CH—, —C($CH_3$)=CH—, —$CH_2$CH=CH$CH_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" as used herein includes an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene- group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 10 or 1 to 6 carbon atoms in the chain. "Branched-chain" as used herein includes that one or more lower alkyl groups such as methyl, ethyl or propyl are attached to a linear alkyl chain (e.g., 2-methylbutyl). "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylsulfonate ester" as used herein includes an alkyl-$SO_3$— group wherein the alkyl group is as defined herein. Preferred alkylsulfonate ester groups are those wherein the alkyl group is lower alkyl. Representative alkylsulfonate ester groups include mesylate ester (i.e., methylsulfonate ester).

An "optionally substituted" alkylsulfonate ester includes an alkylsulfonate ester as defined herein, wherein the aryl group is additionally substituted with from 0 to 3 halo, alkyl, aryl, haloalkyl, or haloaryl groups as defined herein. Preferred optionally substituted alkylsulfonate groups include triflate ester (i.e., trifluoromethylsulfonate ester).

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthioalkylene- group wherein alkylthio and alkylene are defined herein. Representative alkylthioalkyl groups include methylthiomethyl, ethylthiopropyl, isopropylthioethyl, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amido" as used herein includes a group of formula $Y_1Y_2$N—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2$N—C(O)—), methylamido, dimethylamido, diethylamido, and the like. Preferably, "amido" is an —C(O)NRR' group where R and R' are members independently selected from the group consisting of H and alkyl. More preferably, at least one of R and R' is H.

"Amidoalkyl" as used herein includes an amido-alkylene-group wherein amido and alkylene are defined herein. Representative amidoalkyl groups include amidomethyl, amidoethyl, dimethylamidomethyl, and the like.

"Amino" as used herein includes a group of formula $Y_1Y_2N-$ wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N-$), methylamino, dimethylamino, diethylamino, tritylamino, and the like. Preferably, "amino" is an $-NRR'$ group where R and R' are members independently selected from the group consisting of H and alkyl. Preferably, at least one of R and R' is H.

An "optionally substituted" amino group includes an amino group as defined herein.

"Aminoalkyl" as used herein includes an amino-alkylene-group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Arylsulfonate ester" as used herein includes an aryl-$SO_3-$ group wherein the aryl group is as defined herein. Representative arylsulfonate ester groups include phenylsulfonate ester.

An "optionally substituted" arylsulfonate ester includes an arylsulfonate ester as defined herein, wherein the aryl group is additionally substituted with from 0 to 3 halo, alkyl, aryl, haloalkyl, or haloaryl groups as defined herein. Preferred optionally substituted arylsulfonate esters include tosylate ester (i.e., p-tolylsulfonate ester).

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzothiazoline, benzothiophene, benzofurans, benzimidazole, indole, benzoindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring, a cationic counterion (e.g., the cation of a Group I metal such as sodium) must be added to balance the negative charge from additional sulfonato groups. Similarly, anionic counterions must be added to balance any additional cationic groups (e.g., most basic amino groups under physiological conditions). In some embodiments, a counterion can be covalently connected to the compound (e.g., a zwitterionic group containing a sulfonato-anionic group and a trialkylamino cationic group).

"Biomolecule" as used herein includes a natural or synthetic molecule for use in biological systems. Preferred biomolecules include a protein, a peptide, an enzyme substrate, a hormone, an antibody, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragment of RNA, nucleotide triphosphates, acyclo terminator triphosphates, PNA, and the like. More preferred biomolecules include a protein, a peptide, an antibody, an avidin, a streptavidin, and the like. Even more preferred biomolecules include a peptide, an antibody, an avidin, and a streptavidin.

"Carboxy" and "carboxyl" as used herein include a HOC(O)— group (i.e., a carboxylic acid) or a salt thereof. Preferably, the salt counterion is non-toxic (e.g., a cation commonly used in pharmaceuticals). Representative salts include an alkali metal salt (e.g., sodium, potassium) or a tetraalkylammonium salt (e.g., tetraethylammonium), "Carboxyalkyl" as used herein includes a HOC(O)-alkylene- group wherein alkylene is defined herein. Representative carboxyalkyls include carboxymethyl (i.e., HOC(O)$CH_2-$) and carboxyethyl (i.e., HOC(O)$CH_2CH_2-$).

"Cycloalkenyl" as used herein includes a cyclic hydrocarbon group of 4 to about 15 carbon atoms that contains at least one carbon-carbon double bond. The cycloalkenyl ring may include from 0 to 6 $R^{14}$ substituents (e.g., $R^{14}$ as defined in Formula I) and 0 to 2 $R^L$ substituents, and when present, the ring-fused aryl or heteroaryl rings may also include from 0 to 4 $R^{14}$ substituents and 0 to 2 $R^L$ substituents. Preferred alkenyl groups have 5 to about 12 carbon atoms. More preferred alkenyl groups contain 7 to about 14 carbon atoms. Representative cycloalkenyl groups include cyclopentenyl, cyclohexenyl, and the like.

"Cycloalkynyl" as used herein includes a mono- or multicyclic hydrocarbon ring system of 5 to about 15 carbon atoms that contains at least one carbon-carbon triple bond. In a preferred aspect, the cyclic hydrocarbon may optionally be interrupted by a heteroatom (e.g., N, O, S; preferably N) and may include at least one ring-fused aryl or heteroaryl ring (e.g., DBCO or DBCO-1). The cycloalkynyl ring may include from 0 to 6 $R^{14}$ substituents (e.g., $R^{14}$ as defined in Formula I) and 0 to 2 $R^L$ substituents, and when present, the ring-fused aryl or heteroaryl rings may also include from 0 to 4 $R^{14}$ substituents and 0 to 2 $R^L$ substituents. In some aspect, the $R^L$ substituent includes a ring-fused heteroaryl group as part of the linking group with the biomolecule (e.g., the reaction of DBCO with an azide-substituted biomolecule). Preferred alkynyl groups have 5 to about 12 carbon atoms. More preferred alkynyl groups contain 7 to about 14 carbon atoms. Representative cycloalkynyl groups include cyclopentynyl, cyclohexynyl, cyclooctynyl, dibenzocyclooctynyl (or DBCO, which includes a nitrogen in the "octyne" ring or DBCO-1), BARAC, DIFO, DIBO, TMDIBO, DIFO3 and the like.

"Cycloalkynylcarbonyl" includes the definition of cycloalkynyl above with an exocylic carbonyl, for example, a dibenzocyclooctynylcarbonyl or C(O)DBCO, which includes a nitrogen in the "octyne" ring and an exocyclic carbonyl group, and the like.

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one sp²-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Cyanine dye" as used herein includes a compound having two substituted or unsubstituted nitrogen-containing heterocyclic rings joined by an unsaturated bridge. In certain instances, cyanine dyes are referred to herein as "oxidized" dyes. After reduction (by hydrogen or deuterium), the cyanine dyes are reduced to compounds of a preferred embodiment of the present invention (i.e., hydrocyanines). For example, "reduced cyanine dye," "hydrocyanine," or "deuterocyanine" include a cyanine dye wherein the iminium cation has been reduced.

"Exocyclic alkene" or "exocyclic olefin" as used interchangeably herein include an alkene having one alkene carbon that is part of a ring and the other alkene carbon not part of the same ring, though it may be included within a second ring. The second alkene carbon can be unsubstituted or substituted. If the second alkene carbon is disubstituted, the substituents can be the same (e.g., 1,1-dimethyl substitution) or different (e.g., 1-methyl-1-(2-ethoxyethyl) substitution). Examples of compounds with exocyclic alkenes include methylenecyclohexane; (E)-1-ethylidene-2,3-dihydro-1H-indene; pentan-3-ylidenecycloheptane; 2-cyclobutylidenepropan-1-ol; and (3-methoxycyclopent-2-enylidene)cyclohexane.

"Geminal" substituents as used herein includes two or more substituents that are directly attached to the same atom. An example is 3,3-dimethyl substitution on a cyclohexyl or spirocyclohexyl ring.

"Halo" or "halogen" as used herein include fluoro, chloro, bromo, or iodo.

"Haloalkyl" as used herein includes an alkyl group wherein the alkyl group includes one or more halo-substituents (e.g., trifluoromethyl).

"Haloaryl" as used herein includes an alkyl group wherein the aryl group includes one or more halo-substituents (e.g., 2,4,6-phenyl).

"Heptamethine" as used herein includes a polymethine containing seven polymethine carbons. In a preferred embodiment, the heptamethine is substituted at the 4-position.

"Heteroatom" as used herein includes an atom other than carbon or hydrogen. Representative heteroatoms include O, S, P, and N. The nitrogen or sulfur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., $-C_1$-$C_9$ alkylene-O-$C_1$-$C_9$ alkylene-). In some embodiments, a heteroatom is further substituted with an acyl, alkyl, aryl, cycloalkyl, heterocyclyl, or heteroaryl group (e.g., —N(Me)-; —N(Ac)—).

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic saturated monocyclic or multicyclic ring system of about 3 to about 10 ring atoms, preferably about 5 to about 10 ring atoms, in which one or more of the atoms in the ring system is an element or elements other than carbon, e.g., nitrogen, oxygen or sulfur. Preferred heterocyclyl groups contain about 5 to about 6 ring atoms. A heterocyclyl group optionally comprises at least one sp²-hybridized atom (e.g., a ring incorporating an carbonyl, endocyclic olefin, or exocyclic olefin). The prefix "aza," "oxa," or "thia" before heterocyclyl means that at least a nitrogen, oxygen or sulfur atom respectively is present as a ring atom. The nitrogen or sulfur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylene" as used herein includes a bivalent heterocyclyl group. Representative cycloalkylenyl groups include 1,2-, 1,3-, or 1,4-piperdinylene as well as 2,3- or 2,4-cis- or trans-piperidinylene.

"Heteroaryl" as used herein includes an aromatic monocyclic or multicyclic ring system of about 5 to about 14 ring atoms, preferably about 5 to about 10 ring atoms, in which at least one of the atoms in the ring system is an element other than carbon, i.e., nitrogen, oxygen or sulfur. In one embodiment, preferred heteroaryls contain an aromatic ring with about 5 to about 6 ring atoms. The prefix "aza," "oxa," or "thia" before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

"Linking group" as used herein includes the atoms joining a dye compound (e.g., a dye selected from the examples or the dyes of Formula I-VII) with a biomolecule. Table 1 includes a list of preferred bonds for linking groups (i.e., Column C); the linking group comprises the resulting bond and optionally can include additional atoms. See also R. Haugland, Molecular Probes Handbook of Fluorescent Probes and Research Chemicals, Molecular Probes, Inc. (1992). In one embodiment, $R^{16}$ represents a linking group precursor before the attachment reaction with a biomolecule, and $R^L$ represents the resultant attachment between the compound of Formula I-VII and the biomolecule (i.e., $R^L$ comprises the linking group and the biomolecule linked thereby). In one embodiment, preferred reactive functionalities include phosphoramidite groups, an activated ester (e.g., an NHS ester), thiocyanate, isothiocyanate, maleimide, and iodoacetamide.

"Methine carbon" or "polymethine carbon" as used herein include a carbon that is directly connecting the two heterocyclic rings by means of the polymethine bridge. In a preferred embodiment, at least one polymethine carbon of a polymethine bridge is additionally substituted with another group such as alkyl, cycloalkyl, or aryl (e.g., —CH═CH—C(Ar)═CH—CH═ or ═CH—CH═C(Ar)—(CH═CH)$_2$—).

The "oxidized form" of a compound is a compound in its "oxidized state." This designates a compound of formula X (preferably, a fluorescent compound) as opposed to its reduced form of formula (X+2e$^-$+2M), wherein M$^+$ is preferably H$^+$. For example, reaction of a compound of Formula I with an oxidant produces a fluorescent, oxidized form by abstraction of the $R_{1a}$ hydrogen or hydrogen isotope (i.e., the loss of H$^-$ and a cationic counterion).

"Pentamethine" as used herein includes a polymethine containing five polymethine carbons. In a preferred embodiment, the pentamethine is substituted at the 3-position.

A "photoactivatable moiety" is a chemical group or molecule that, upon exposure to light, absorbs a photon to enter an excited state. The excited-state group or molecule undergoes a chemical reaction or series of reactions. Alternatively, the excitation changes the light-emitting properties of the group or molecules (e.g., photoactivatable fluorescent dyes). Examples of photoactivatable moieties include aryl azides, benzophenones (e.g., 4-benzoyloxybenzoic acid as well as its esters and amides), nitroaryl groups (e.g., 5-carboxymethoxy-2-nitrobenzyl (CMNB); α-carboxy-2-nitrobenzyl (CNB); 4,5-dimethoxy-2-nitrobenzyl (DMNB); 1-(4,5-dimethoxy-2-nitrophenyl)ethyl (DMNPE); nitrophenyl (NP); and 1-(2-nitrophenyl)ethyl (NPE) groups), coumarins, diazo groups, photoactivatable fluorescent dyes (e.g., 5-carboxyfluorescein-bis-(5-carboxymethoxy-2-nitrobenzyl) ether, β-alanine-carboxamide, succinimidyl ester), and tetrazoles.

"Polyene" as used herein includes a straight or branched bivalent hydrocarbon chain containing at least two "alkenylene" groups as defined herein that are in conjugation. The polyene is optionally substituted with one or more "alkylene group substituents" as defined herein (i.e., in the Examples and disclosed embodiments). A portion of the polyene may be incorporated into a ring (i.e., ═C(R)—, wherein R and the terminal bond are linked in a larger ring; or —C(R$^1$)═C(R$^2$)—, wherein R$^1$ and R$^2$ are linked in a larger ring). Representative polyenes include —CH═CH—CH═CH—, —CH═CH—C(Ar)═CH—CH═C(R)—, —C(R)═CH—CH═C(Ar)—(CH═CH)$_2$—, and the like.

"Polymethine" or "polymethine bridge" as used herein includes the series of conjugated, sp$^2$-hybridized carbons that form the unsaturated bridge directly connecting the two nitrogen-containing heterocyclic rings of a dye compound (e.g., a fluorescent compound of Formula I-VII). In a preferred embodiment, the polymethine has five or seven carbons directly connecting the heterocyclic rings (i.e., pentamethine or heptamethine).

"Phosphoramidityl" as used herein includes a trivalent phosphorous atom bonded to two alkoxy groups and an amino group.

As used herein, "reduced dye" includes a dye molecule in which one or more n-bonds have been reduced, disrupting the extended π-conjugation, resulting in a molecule that exhibits negligible or no fluorescence at near-IR frequencies or substantially non-fluorescent. For example, "reduced cyanine dye," "hydrocyanine," or "deuterocyanine" include a cyanine dye wherein the iminium cation has been reduced. "Deuterocyanine," as used herein, includes a cyanine dye that has been reduced by a deuterated reducing agent thus incorporating deuterium into the reduced molecule.

As used herein, "reactive oxygen species" and "ROS" refer interchangeably to molecules or ions that contain oxygen ions, free radicals, peroxides, or combinations thereof. Reactive oxygen species can be organic or inorganic. Examples of reactive oxygen species include, but are not limited to, super oxides; oxygen free radicals, such as hydroxyl radicals and peroxyl radicals; peroxides, singlet oxygen, ozone, nitrogen monoxide; anions, such as hydroxyl anions and superoxide anions; hypochlorus acid; and peroxynitrites, as well as combinations of any such reactive oxygen species.

"Sulfonato" as used herein includes an —SO$_3^-$ group, preferably balanced by a cation such as H$^+$, Na$^+$, K$^+$, and the like. Preferably, the cation is non-toxic (e.g., a cation commonly used in pharmaceuticals). Representative cations include an alkali metal ion (e.g., sodium, potassium) or a tetraalkylammonium (e.g., tetraethylammonium), "Sulfonatoalkyl" as used herein includes an sulfonatoalkylene- group wherein sulfonato and alkylene are as defined herein. A more preferred embodiment includes alkylene groups having from 2 to 6 carbon atoms, and a most preferred embodiment includes alkylene groups having 2, 3, or 4 carbons. Representative sulfonatoalkyls include sulfonatomethyl, 3-sulfonatopropyl, 4-sulfonatobutyl, 5-sulfonatopentyl, 6-sulfonatohexyl, and the like.

As used herein, the term "ionic group" includes a moiety comprising one or more charged substituents. The "charged substituent" is a functional group that is generally anionic or cationic when in substantially neutral aqueous conditions (e.g., a pH of about 6.5 to 8.0 or about physiological pH (7.4)). As recited above, examples of charged anionic substituents include anions of inorganic and organic acids, such as sulfonate (—SO$_3^{1-}$), sulfinate, carboxylate, phosphinate, phosphonate, phosphate, and esters (such as alkyl esters) thereof. In some embodiments, the charged substituent is sulfonate. Examples of charged cationic substituents include quaternary amines (—NR$_3^+$), where R is independently selected from C$_{1-6}$ alkyl, aryl, and arylalkyl. Other charged cationic substituents include protonated primary, secondary, and tertiary amines, and well as guanidinium. In some embodiments, the charged substituent is —N(CH$_3$)$_3^+$.

In some embodiments, the ionic group consists solely of a charged substituent. Examples of charged substituents include any of those mentioned above, such as sulfonate and —N(CH$_3$)$_3^+$.

In some embodiments, the ionic group corresponds to a C$_{1-20}$ alkyl group substituted with one or more charged substituents, wherein the C$_{1-20}$ alkyl group is optionally further substituted with 1, 2, 3, 4, 5, or 6 substituents independently selected from halo, cyano, nitro, and C$_{1-4}$ haloalkyl, wherein 0, 1, 2, 3, 4, 5, or 6 carbon atoms of the alkyl group are individually replaced with O, S, C(O), C(O)O, NR', C(O)NR', SO, SO$_2$, SO$_2$NR', wherein R' is H or C$_{1-6}$ alkyl, with the proviso that the replacement does not result in an unstable moiety (e.g., —O—O—, —O—S—, etc.).

Examples of ionic groups include a group selected from the following formulae:

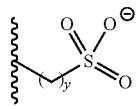 and 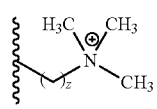

wherein y and z are independently selected from 0, 1, 2, 3, 4, 5, 6, 7, and 8. In some embodiments, y and z are independently selected from 1, 2, 3, 4, 5, 6, 7, and 8. In some embodiments, y and z are independently selected from 1, 2, 3, and 4. In some embodiments, y and z are 0.

Further examples of ionic groups include a group selected from the following formulae:

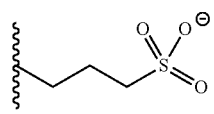 and 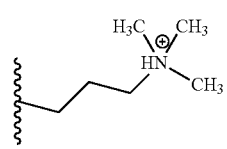

In some embodiments, the ionic group can contain two or more charged substituents. For example, the ionic group can include both an anionic and a cationic substituent, forming a "zwitterionic group" (or "zwitterion"). Zwitterionic groups can be particularly useful as substituents in the present invention because they incorporate additional formal charges in the conjugate yet do not impact net total charge, thereby facilitating charge-balance. In some embodiments, a zwitterionic group corresponds to a C$_{1-20}$ alkyl group substituted with at least one positively charged (cationic) substituent and at least one negatively charged (anionic) group, such that the overall charge of the zwitterionic group is zero, and wherein the C$_{1-20}$ alkyl group is optionally further substituted with 1, 2, 3, 4, 5, or 6 substituents independently selected from halo, cyano, nitro, and C$_{1-4}$ haloalkyl, wherein 0, 1, 2, 3, 4, 5, or 6 carbon atoms of the C$_{1-20}$ alkyl group are individually replaced with O, S, C(O), C(O)O, NR', C(O)NR', SO, SO$_2$, SO$_2$NR', wherein R' is H or C$_{1-6}$ alkyl, with the proviso that the replacement does not result in an unstable moiety (e.g., —O—O—, —O—S—, etc.).

In one embodiment, the zwitterionic group includes a sulfonate group and a quaternary amine of formula —NR$_3^+$, wherein R is independently selected from C$_{1-6}$ alkyl, aryl, and arylalkyl. In one aspect, the zwitterionic group has the formula:

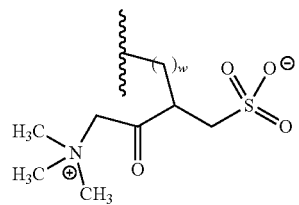

wherein w is 1, 2, 3, 4, 5, 6, 7, or 8. In some embodiments, the zwitterionic group has the formula:

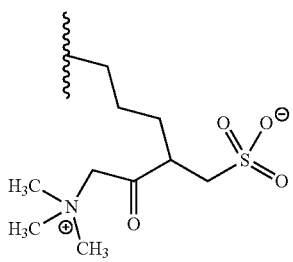 [SMILES: *CCCC(CS(=O)(=O)[O-])C(=O)C[N+](C)(C)C]

II. Reduced Cyanine Dye Compounds

Compounds of Formula I-VII are useful as reactive oxygen species (ROS) probes for biochemical in vivo and in vitro applications. In the presence of radicals (which may be present in inflamed tissues, tumor tissues, during reaction of horseradish peroxidase (HRP) enzyme with H$_2$O$_2$, and the like), non-fluorescent hydrocyanines oxidize to fluorescent cyanine dyes. This property of hydrocyanine dyes can be exploited for the development of highly sensitive assay platforms or in vitro and in vivo imaging probes. Tissues of interest, such as inflamed or tumor tissues, and processes of interest, such as the reaction of horseradish peroxidase (HRP) enzyme with H$_2$O$_2$, can produce higher concentration of radical oxidants, which react with the hydrocyanine or deuterocyanine compounds to produce fluorescent dyes.

Examples of ROS include, but are not limited to, oxygen, superoxide, peroxide, hydrogen peroxide, and hydroxyl radicals and ions. ROS are implicated in a number of physiological processes, including redox signaling, pathogen response, aging, and certain transcriptional processes. In tumor cells, for example, production of ROS as a result of hypoxia has been shown to activate transcription factors that promote tumor growth.

Advantages of the compounds of the present invention include, e.g., very high sensitivity, improved stability, and improved water solubility. The applications are novel and enable researchers to do experiments which are not possible with the existing technologies. Quantitative detection of ROS is also possible with a ratiometric probe (e.g., hydrocyanine attached with another always-on dye molecule a conjugate disclosed herein). The hydrocyanine dyes are used as a platform technology for detecting ROS in biological samples in the entire gamut of the spectrum from visible to the NIR region.

A. Compounds of Formula I

In one aspect, the present invention provides a compound of Formula I:

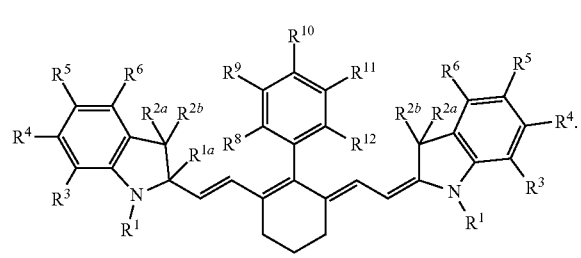

Each R$^1$ is an independently selected alkyl group that is additionally substituted with from 0 to 1 R$^{14}$ and from 0 to 1 -L-Y—Z; wherein the alkyl is optionally interrupted by at least one heteroatom or an ionic group.

In a preferred aspect, $R^1$ is not interrupted by a heteroatom. Alternatively, $R^1$ is interrupted by at least one ether, thioether, substituted amino, or amido group.

In a preferred aspect, $R^1$ is $C_1$-$C_{20}$ alkyl. In a more preferred aspect, $R^1$ is $C_1$-$C_{12}$ or $C_2$-$C_8$ alkyl. In a still more preferred aspect, $R^1$ is 2, 3, or 4.

In another preferred aspect, $R^1$ is $(CH_2)_rSO_3H$ or $(CH_2)_rSO_3^-$; and r is an integer from 1 to 20. In a more preferred aspect, r is 2, 3, or 4. Alternatively, $R^1$ is $(CH_2)_rOH$; and r is an integer from 2 to 6 (e.g., 6-hydroxyhexyl).

In still another preferred aspect, $R^1$ is an alkyl group that is additionally substituted with 1 $R^{14}$. In a more preferred aspect, the $R^{14}$ is carboxy or sulfonato. In a still more preferred aspect, $R^{14}$ is sulfonato. Alternatively, $R^{14}$ is hydroxy. In a yet still more preferred aspect, $R^{14}$ is 3-sulfonatopropyl or 4-sulfonatobutyl.

In yet another preferred aspect, $R^1$ is an unbranched alkyl group that is additionally substituted with 1 $R^{14}$. In a more preferred aspect, $R^1$ is an unbranched alkyl group that is substituted with $R^{14}$ at the end of the alkyl group opposite to its attachment point to the reduced cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl; more preferably, $R^1$ is 3-sulfonatopropyl.

$R^{1a}$ is either hydrogen or deuterium. Alternatively, $R^{1a}$ is tritium.

Each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 -L-Y—Z.

In a preferred aspect, all $R^{2a}$ are the same substituent. Alternatively, all $R^{2b}$ are the same substituent. More preferably, all $R^{2a}$ are the same substituent, and all $R^{2b}$ are the same substituent.

In another preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl. Yet still more preferably, $R^{2a}$ is methyl.

Each $R^3$, $R^4$, $R^5$, and $R^6$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 -L-Y—Z.

In a first aspect, each $R^3$, $R^4$, $R^5$, and $R^6$ is a member independently selected from the group consisting of hydrogen, alkyl, alkenyl, halo, alkoxy, cyano, carboxyl, alkoxycarbonyl, amido, sulfonato, alkoxyalkyl, carboxyalkyl, alkoxycarbonylalkyl, and sulfonatoalkyl. In a preferred aspect, each $R^3$, $R^4$, $R^5$, and $R^6$ is a member independently selected from the group of hydrogen, alkyl, carboxy, carboxyalkyl, sulfanato, and sulfanatoalkyl. In a more preferred embodiment, each $R^3$, $R^4$, $R^5$, and $R^6$ is a member independently selected from the group of hydrogen and sulfanato.

In one aspect, at least one pair of $R^3$, $R^4$, $R^5$, or $R^6$ is the same (i.e., the $R^n$ substituent is not independently selected, but is the same as the other $R^n$ substituent). This aspect can be combined with other aspects specifying the number or type of dye substituents (e.g., exactly two members of the groups $R^3$, $R^4$, $R^5$, and $R^6$ are hydrogen, and the two members are the pair of $R^4$s). Alternatively, at least two, at least three, or all four pairs of $R^3$, $R^4$, $R^5$, or $R^6$ are the same. More preferably, the dye is symmetric or pseudo-symmetric (i.e., $R^1$, $R^{2a}$, and $R^{2b}$ are also not independently selected, but are the same as the other $R^1$, $R^{2a}$, and $R^{2b}$ substituents).

In an alternative aspect, at least one member of the groups $R^3$, $R^4$, $R^5$, and $R^6$ is hydrogen. Alternatively, exactly one member of the groups $R^3$, $R^4$, $R^5$, and $R^6$ is hydrogen. In a preferred aspect, at least one pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ is hydrogen. Alternatively, exactly two, exactly three, exactly four, exactly five, or exactly six members of the groups $R^3$, $R^4$, $R^5$, and $R^6$ are hydrogen. In another aspect, exactly four members of the groups $R^3$, $R^4$, $R^5$, and $R^6$ are hydrogen. Alternatively, exactly five members of the groups $R^3$, $R^4$, $R^5$, and $R^6$ are hydrogen. In a still more preferred aspect, $R^3$, $R^4$, and $R^6$ are hydrogen.

In another alternative aspect, at least one member of the groups $R^3$, $R^4$, $R^5$, and $R^6$ is sulfonato or sulfonatoalkyl. Alternatively, exactly one substituent selected from the groups $R^3$, $R^4$, $R^5$, and $R^6$ is sulfonato or sulfonatoalkyl. In a preferred aspect, $R^5$ is sulfonato. In still another aspect, both members of a pair of substituents selected from the pairs $R^3$ and $R^4$; $R^3$ and $R^5$; $R^3$ and $R^6$; $R^4$ and $R^5$; $R^4$ and $R^6$; and $R^4$ and $R^6$ are each a member independently selected from the group of sulfonato or sulfonatoalkyl. Alternatively, exactly two, exactly three, exactly four, exactly five, or exactly six members of the groups $R^3$, $R^4$, $R^5$, and $R^6$ are each a member independently selected from the group of sulfonato or sulfonatoalkyl.

In another alternative aspect, at least one member of the group $R^3$, $R^4$, $R^5$, and $R^6$ is anionic at physiological pH (e.g., sulfonato $—SO_3^-$, carboxy $—CO_2^-$). Alternatively, exactly one member of the group $R^3$, $R^4$, $R^5$, and $R^6$ is anionic at physiological pH. In a preferred aspect, $R^5$ is anionic at physiological pH. In still another aspect, each member of a pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ is anionic at physiological pH. Alternatively, exactly two, exactly three, exactly four, exactly five, or exactly six members of the groups $R^3$, $R^4$, $R^5$, and $R^6$ are anionic at physiological pH. Alternatively, exactly two, exactly three, or exactly four members of the groups $R^3$, $R^4$, $R^5$, and $R^6$ are anionic at physiological pH.

In another alternative aspect, at least one member of the groups $R^3$, $R^4$, $R^5$, and $R^6$ is halo. Alternatively, exactly one substituent selected from the groups $R^3$, $R^4$, $R^5$, and $R^6$ is halo. Alternatively, exactly two, exactly three, or exactly four members of the groups $R^3$, $R^4$, $R^5$, and $R^6$ are halo.

$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z. In one preferred embodiment, at least one member selected from the group consisting of $R^8$, $R^9$, and $R^{10}$ is halo. More preferably, at least one member selected from the group consisting of $R^8$, $R^9$, and $R^{10}$ is fluoro or chloro.

In one aspect, $R^8$ is halo; more preferably, fluoro or chloro. Preferably, $R^9$, $R^{10}$, $R^{11}$, and $R^{12}$ are each a member independently selected from the group consisting of hydrogen, alkyl, alkoxy, halo, sulfonato, and -L-Y—Z.

In a second aspect, $R^8$ is hydrogen, alkyl, alkoxy, or halo. More preferably, $R^8$ is fluoro; alternatively, $R^8$ is chloro.

In an alternative preferred aspect, $R^8$ is hydrogen.

Alternatively, $R^8$ is a carboxyalkyl. Preferably, $R^8$ is a lower alkyl group with a carboxy-substituent. More preferably, $R^8$ is 5-carboxypentyl, 4-carboxybutyl, 3-carboxypropyl, 2-carboxyethyl, or carboxymethyl. Still more preferably, $R^8$ is 5-carboxypentyl or 2-carboxyethyl. In some aspects, the carboxyalkyl is optionally interrupted by at least one heteroatom (e.g., 4-carboxybutoxy; 2-((2-carboxy)ethyloxy)ethyl).

Alternatively, $R^8$ is carboxyl, alkoxycarbonyl, or amido; more preferably, $R^8$ is carboxyl. Alternatively, $R^8$ is -L-Y—Z.

In one aspect, $R^{10}$ is halo; more preferably, fluoro or chloro. Preferably, $R^8$, $R^9$, $R^{11}$, and $R^{12}$ are each a member independently selected from the group consisting of hydrogen, alkyl, alkoxy, halo, sulfonato, and -L-Y—Z.

In a second aspect, $R^{10}$ is hydrogen, alkyl, alkoxy, or halo. In another more preferred aspect, $R^{10}$ is fluoro; alternatively, $R^{10}$ is chloro.

In an alternative preferred aspect, $R^{10}$ is hydrogen.

Alternatively, $R^{10}$ is a carboxyalkyl. Preferably, $R^{10}$ is a lower alkyl group with a carboxy-substituent. More preferably, $R^{10}$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl. In some aspects, the carboxyalkyl is optionally interrupted by at least one heteroatom (e.g., 4-carboxybutoxy; 2-((2-carboxy)ethyloxy)ethyl).

Alternatively, $R^{10}$ is carboxyl, alkoxycarbonyl, or amido; more preferably, $R^{10}$ is carboxyl. Alternatively, $R^{10}$ is -L-Y—Z.

In one aspect, $R^9$ is -L-Y—Z. Preferably, $R^8$, $R^{10}$, $R^{11}$, and $R^{12}$ are each a member independently selected from the group consisting of hydrogen, alkyl, alkoxy, halo, sulfonato, and -L-Y—Z.

In a second aspect, $R^9$ is hydrogen, alkyl, alkoxy, or halo. In another more preferred aspect, $R^9$ is fluoro; alternatively, $R^9$ is chloro.

In an alternative preferred aspect, $R^9$ is hydrogen.

Alternatively, $R^9$ is a carboxyalkyl. Preferably, $R^9$ is a lower alkyl group with a carboxy-substituent. More preferably, $R^9$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl. In some aspects, the carboxyalkyl is optionally interrupted by at least one heteroatom (e.g., 4-carboxybutoxy; 2-((2-carboxy)ethyloxy)ethyl).

Alternatively, $R^9$ is carboxyl, alkoxycarbonyl, or amido; more preferably, $R^9$ is carboxyl.

In one aspect, $R^{11}$ and $R^{12}$ are each a member independently selected from the group of hydrogen, alkyl, alkenyl, halo, alkoxy, sulfonato, hydroxyl, amino, carboxyl, alkoxycarbonyl, cyano, amido, thioacetyl, and -L-Y—Z. Preferably, $R^{11}$ and $R^{12}$ are each a member independently selected from the group of hydrogen, alkyl, halo, and sulfonato. More preferably, $R^{11}$ and $R^{12}$ are each a member independently selected from the group of hydrogen, halo, and sulfonato.

In a second aspect, $R^{11}$ is hydrogen, alkyl, alkoxy, or halo. In a more preferred aspect, $R^{11}$ is halo; preferably, $R^{11}$ is fluoro or chloro. In an alternative aspect, $R^{11}$ is hydrogen. Alternatively, $R^{10}$ and $R^{11}$ are hydrogen.

In a third aspect, $R^{12}$ is hydrogen, alkyl, alkoxy, or halo. In a more preferred aspect, $R^{12}$ is halo; preferably, $R^{12}$ is fluoro or chloro. In a still more preferred aspect, $R^{10}$ and $R^{12}$ are halogen, preferably fluoro or chloro. Alternatively, $R^{11}$ and $R^{12}$ are halogen, preferably fluoro or chloro. In a yet still more preferred aspect, $R^{10}$, $R^{11}$, and $R^{12}$ are halogen, preferably fluoro or chloro.

In a fourth aspect, the phenyl ring substituted with $R^8$, $R^9$, $R^{10}$, $R^{11}$, and $R^{12}$ is 1,2,3-substituted with independently selected substituents other than hydrogen, wherein the 1-substituent is the polymethine bridge (e.g., $R^8$ and $R^9$ are the same halo group; $R^8$ and $R^9$ are different halo groups; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted. Preferably, at least two of the substituents are halo; more preferably, fluoro or chloro.

In a fifth aspect, the phenyl ring substituted with $R^8$, $R^9$, $R^{10}$, $R^{11}$, and $R^{12}$ is 1,2,3,4-substituted with independently selected substituents other than hydrogen, wherein the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted. Preferably, at least two of the substituents are halo; more preferably, fluoro or chloro. Alternatively and preferably, at least three of the substituents are halo; more preferably, fluoro or chloro.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, wherein the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

Preferably, at least two of the phenyl ring substituents are halo; more preferably. fluoro or chloro. Alternatively, at least three of the substituents are halo; more preferably. fluoro or chloro (e.g., $R^8$, $R^{10}$, and $R^{12}$ are halo). Alternatively, at least four of the substituents are halo; more preferably. fluoro or chloro (e.g., $R^8$, $R^9$, $R^{11}$, and $R^{12}$ are halo).

In a seventh aspect, $R^8$, $R^9$, $R^{10}$, $R^{11}$, and $R^{12}$ are each a member independently selected from the group of hydrogen, alkyl, alkoxy, halo, sulfonato, and sulfonatoalkyl.

Fluoro substitution has been shown to increase quantum yield and photostability in fluorescein dyes as well as lowering dye $pK_a$. See Sun, W.-C. et al. *J. Org. Chem.* 1997, 62, 6469-6475. In an eighth aspect, at least one member of the group $R^8$, $R^9$, $R^{10}$, $R^{11}$, and $R^{12}$ is a fluoro substituent. Alternatively, at least one member of the groups $R^3$, $R^3$, $R^4$, $R^5$, $R^6$, and $R^{14}$ is a fluoro substituent. In yet another aspect, at least two members of the groups $R^3$, $R^3$, $R^4$, $R^5$, $R^6$, $R^4$, R, $R^6$, $R^8$, $R^9$, $R^{10}$, $R^{11}$, $R^{12}$, and $R^{14}$ are fluoro substituents. In yet another aspect, at least three members of $R^3$, $R^4$, R, $R^6$, $R^8$, $R^9$, $R^{10}$, $R^{11}$, $R^{12}$, and $R^{14}$ are fluoro substituents. In yet another aspect, at least four or at least five members of the groups $R^3$, $R^4$, R, $R^6$, $R^8$, $R^9$, $R^{10}$, $R^{11}$, $R^{12}$, and $R^{14}$ are fluoro substituents.

As demonstrated in the examples, chloro substitution also has a favorable effect on the dye properties, much as the fluoro group does. In a ninth aspect, at least one member of the group $R^8$, $R^9$, $R^{10}$, $R^{11}$, and $R^{12}$ is a chloro substituent.

Alternatively, at least one member of the groups $R^3$, $R^4$, R, $R^6$, $R^8$, $R^9$, $R^{10}$, $R^{11}$, $R^{12}$, and $R^{14}$ is a chloro substituent. In yet another aspect, at least two members of the groups $R^3$, $R^4$, R, $R^6$, $R^8$, $R^9$, $R^{10}$, $R^{11}$, $R^{12}$, and $R^{14}$ are chloro substituents. In yet another aspect, at least three members of the groups $R^3$, $R^4$, R, $R^6$, $R^8$, $R^9$, $R^{10}$, $R^{11}$, $R^{12}$, and $R^{14}$ are chloro substituents. In yet another aspect, at least four or at least five members of the groups $R^3$, $R^4$, R, $R^6$, $R^8$, $R^9$, $R^{10}$, $R^{11}$, $R^{12}$, and $R^{14}$ are chloro substituents.

Each $R^{13}$ is a member independently selected from the group of hydroxyl, amino, carboxyl, and alkoxycarbonyl. In a preferred embodiment, $R^{13}$ is carboxyl or alkoxycarbonyl. In a more preferred embodiment, $R^{13}$ is carboxyl. Alternatively, $R^{13}$ is cyano. Alternatively, $R^{13}$ is hydroxyl.

Each $R^{14}$ is a member independently selected from the group consisting of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the alkyl or alkenyl is additionally substituted with from 0 to 1 $R^{13}$ and from 0 to 1 -L-Y—Z. In a preferred aspect, $R^{14}$ is alkyl, alkenyl, carboxyl, alkoxycarbonyl, amido, alkoxycarbonylalkyl, halo, sulfonato, or sulfonatoalkyl. Alternatively, $R^{14}$ is carboxyalkyl, hydroxyalkyl, halo, sulfonato, or sulfonatoalkyl. In an alternative aspect, $R^{14}$ is alkyl or alkyl substituted with 1 $R^{13}$. Alternatively, $R^{14}$ is halo or sulfonato. Alternatively, $R^{14}$ is sulfonato. Alternatively, $R^{14}$ is hydroxy.

In an alternative aspect, at least one $R^{14}$ substituent is zwitterionic at physiological pH (e.g., an alkyl group with anionic sulfonato —$SO_3^-$ and a cationic trialkylammonium group substituents). Alternatively, exactly one $R^{14}$ substituent is zwitterionic at physiological pH. In still another aspect, at least one pair of $R^{14}$ substituents is zwitterionic at physiological pH. Alternatively, exactly one, exactly two, exactly three, or exactly four $R^{14}$ substituents are zwitterionic at physiological pH.

Each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom. In a preferred aspect, L is a bond, with the proviso that L is not a bond when that would produce a highly unstable structure (e.g., N-L-$R^{13}$, if $R^{13}$ is —$CO_2H$). Alternatively, L is a $C_1$-$C_{14}$ alkylene; more preferably, L is a $C_1$-$C_{10}$ alkylene or a $C_1$-$C_6$ alkylene. Alternatively, L is a $C_1$-$C_{12}$ alkylene interrupted by ether linkages (e.g., a polyethylene glycol oligomer).

In a preferred aspect, the alkylene or alkenylene is not interrupted by a heteroatom.

Alternatively, L is interrupted by at least one ether, thioether, substituted amino, or amido group.

Each Y is an optional member independently selected from the group consisting of a bond, —O—, —S—, —NH—, —NHC(O)—, —C(O)NH—, —$NR^{15}$—, —$NR^{15}$C(O)—, —C(O)$NR^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is independently selected from the group consisting of $R^{13}$ and $R^{16}$. Alternatively, each Z is an $R^{14}$ substituent, wherein the $R^{14}$ substituent is not substituted with any -L-Y—Z group. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or alkyl with an activated acyl substituent. In a yet still more preferred aspect, Z is 5-carboxypentyl or 4-carboxybutyl.

In an alternative preferred aspect, Z is a carboxyalkyl. Preferably, Z is a lower alkyl group with a carboxy-substituent. More preferably, Z is 5-carboxypentyl, 4-carboxybutyl, 3-carboxypropyl, 2-carboxyethyl, or carboxymethyl. Still more preferably, Z is 5-carboxypentyl or 2-carboxyethyl.

In another alternative preferred aspect, -L-Y— is a bond; Z is $(CH_2)_tR^{13}$; $R^{13}$ is carboxyl or activated acyl; and t is an integer from 0 to 10, such as 0, 1, 2, 3, 4, 5, 6, 7, 8, 9, or 10. Alternatively, t is an integer from 1 to 10.

In still another alternative preferred aspect, the Z group's L group is a bond. Alternatively, Z is $R^{13}$ or $R^{16}$ that is directly bonded to the phenyl ring itself if L and Y are also bonds.

In yet still another alternative preferred aspect, -L-Y—Z has at least three carbons. Alternatively, Z has at least three carbons.

In yet still another alternative preferred aspect, -L-Y—Z has at least four carbons. Alternatively, Z has at least four carbons.

In an alternative embodiment, —Y—Z is a member selected from the group consisting of —$N(Z^1)_2$, —$N(Z^1)C(O)Z^1$, and —$C(O)N(Z^1)_2$, and the two $Z^1$ groups may optionally be linked to form a cycloalkynyl group.

In one embodiment, each $R^{15}$ is a member independently selected from the group consisting of alkyl and alkoxycarbonylalkyl; wherein the alkyl is optionally interrupted by at least one heteroatom or an ionic group (e.g., a charged alkylammonium group, such as that in —$CH_2(NMe_2)CH_2CH_2CH_2$—). Preferably, each $R^{15}$ is an independently selected alkyl.

In an alternative embodiment, $R^{15}$ is a member selected from the group of alkyl and alkoxycarbonylalkyl; wherein the alkyl is optionally interrupted by at least one heteroatom or an ionic group (e.g., a charged alkylammonium group, such as that in —$CH_2(NMe_2)CH_2CH_2CH_2$—). In a preferred aspect, $R^{15}$ is alkyl. In a more preferred aspect, $R^{15}$ is lower alkyl. In another aspect, $R^{15}$ is interrupted by ether linkages (e.g., a polyethylene glycol oligomer).

In one embodiment, each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

In an alternative embodiment, each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, cycloalkynyl, spirocycloalkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester. Preferably, "optionally substituted amino" is selected from the group consisting of —$NH_2$, —$NHR_{15}$, and —$N(R_{15})_2$. Alternatively, each $R^{16}$ is independently a member selected from the group consisting of activated acyl, azido, amino, alkylamino, diazo, hydrazinyl, imido ester, isocyanato, isothiocyanato, maleimidyl, phosphoramidityl, alkynyl, cycloalkynyl, cycloalkynylcarbonyl, spirocycloalkynyl, a pegylated azido, a pegylated alkynyl, a pegylated cycloalkynyl, and a pegylated spirocycloalkynyl. Alternatively, each $R^{16}$ is independently a member selected from the group consisting of activated acyl, amino, alkylamino, imido ester, isothiocyanato, and maleimidyl. Alternatively, each $R^{16}$ is independently a member selected from the group consisting of azido, alkynyl, cycloalkynyl, cycloalkynylcarbonyl, spirocycloalkynyl, a pegylated azido, a pegylated alkynyl, a pegylated cycloalkynyl, and a pegylated spirocycloalkynyl.

In a preferred embodiment, the compounds of Formula I have the structures:

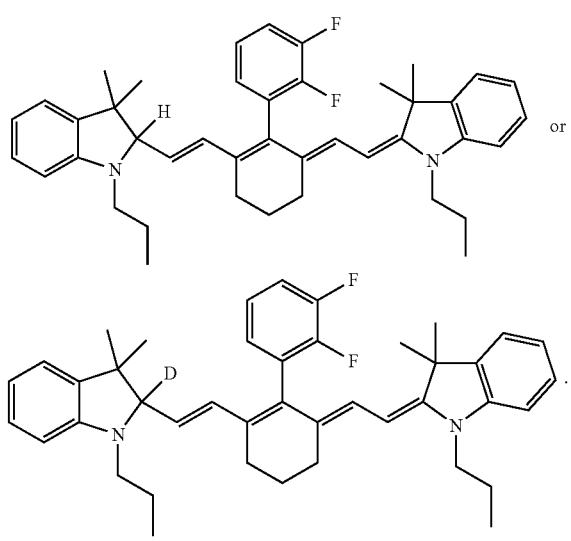

In one embodiment, the parent compound's oxidized form has a balanced charge. In a preferred aspect, the compound's net anionic charge in the oxidized state is balanced by alkali metal counterions (e.g., sodium or potassium). In a preferred aspect, in the parent compound's oxidized state, at least one of the counterions is sodium. Alternatively, all of the counterions are sodium.

In one embodiment, the compound's net cationic charge in the oxidized state is balanced by organic anions (e.g., acetate, chloride, sulfonate, or formate). In a preferred aspect, in the parent compound's oxidized state, at least one of the counterions is chloride or acetate. Alternatively, all of the counterions are chloride or acetate.

The compound may also incorporate covalent bonds to both cationic and anionic groups to produce a balanced charge. Embodiments of such compounds are set forth in U.S. Patent Publication No. 2012/0028291, which is incorporated by reference. In a preferred aspect, the compound's charge in the oxidized state is balanced by a combination of alkali metal counterions (e.g., sodium or potassium) and tetraalkylammonium substituents (e.g., a trimethylammonium substituent; a triethylammonium substituent; or a methyl diethylammonium substituent).

B. Compounds of Formula II

In another embodiment, the present invention provides a compound of Formula II:

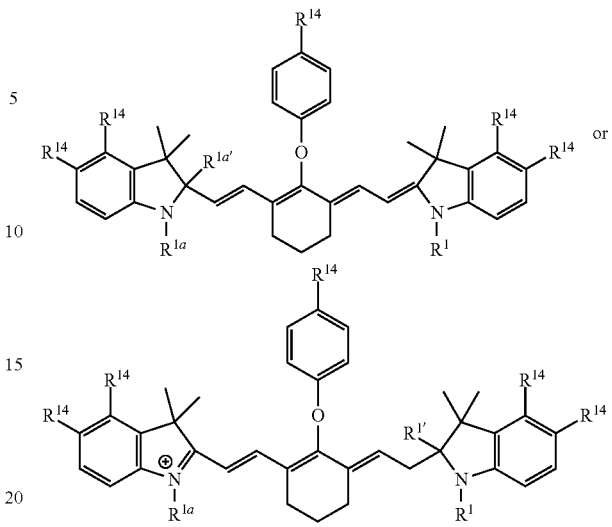

$R^1$ and $R^{1a}$ are independently selected from L-Y—Z and an alkyl group that is additionally substituted with from 0 to 1 $R^{13}$; wherein the alkyl is optionally interrupted by at least one heteroatom or an ionic group (e.g., a charged alkylammonium group, such as that in —$CH_2(NMe_2)$ $CH_2CH_2CH_2$—). In a preferred aspect, $R^1$ and $R^{1a}$ are independently a $C_2$-$C_{12}$ alkyl. In a more preferred aspect, $R^1$ and $R^{1a}$ are independently $C_2$-$C_8$ alkyl. In a still more preferred aspect, $R^1$ and $R^{1a}$ are independently $C_2$-$C_6$ alkyl. In a yet still more preferred aspect, $R^1$ and $R^{1a}$ are independently ethyl, propyl, butyl, or pentyl, and $R^1$ is additionally substituted with 1 $R^{13}$. In one aspect, this $R^{13}$ substituent is sulfonato; alternatively, $R^{13}$ is hydroxyl.

In a preferred aspect, $R^1$ and $R^{1a}$ are independently $(CH_2)_rSO_3H$ or $(CH_2)_rSO_3^-$; and r is an integer from 1 to 20. In a more preferred aspect, r is 2, 3, or 4. Alternatively, $R^1$ is $(CH_2)_rOH$; and r is an integer from 2 to 6 (e.g., 6-hydroxyhexyl).

In one aspect, $R^1$ and $R^{1a}$ are independently an alkyl group that is additionally substituted with 1 $R^{13}$, wherein $R^{13}$ is selected from the group of hydroxyl, amino, carboxy, and sulfonato. In a more preferred aspect, the $R^{13}$ substituent of $R^1$ and $R^{1a}$ are independently a carboxy or sulfonato. In a still more preferred aspect, the $R^{13}$ substituent of $R^1$ or $R^{1a}$ is sulfonato. In a yet still more preferred aspect, $R^1$ and $R^{1a}$ are independently a sulfonatoethyl, sulfonatopropyl, sulfonatobutyl, or sulfonatopentyl.

In another alternative preferred aspect, $R^1$ and $R^{1a}$ are independently an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the reduced cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl.

$R^{1a'}$ and $R^{1'}$ are independently either hydrogen or deuterium. Alternatively, $R^{1a'}$ or $R^{1'}$ is tritium.

Each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato.

Each $R^{14}$ is a member independently selected from the group of alkyl, alkenyl, halo, hydrogen, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 1 $R^{13}$; and wherein at least one $R^{14}$ is sulfonato. Alternatively, each $R^{14}$ is a member independently selected from the group of alkyl, alkenyl, halo, hydrogen, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 2 $R^{13}$.

In a preferred aspect, at least one $R^{14}$ is alkyl, alkenyl, carboxyl, alkoxycarbonyl, amido, or alkoxycarbonylalkyl. Alternatively, at least two $R^{14}$ are sulfonato. Alternatively, at least one $R^{14}$ is hydroxy. In a more preferred aspect, at least one $R^{14}$ is alkyl or alkyl substituted with 1 $R^{13}$. Alternatively, at least one $R^{14}$ is carboxyalkyl, hydroxyalkyl, or sulfonatoalkyl. In some aspects, the carboxyalkyl, hydroxyalkyl, or sulfonatoalkyl is optionally interrupted by at least one heteroatom (e.g., 4-carboxybutoxy; 2-(hydroxyethyloxy)ethyl).

In one aspect, at least two of the $R^{14}$ substituents are each independently carboxy, carboxyalkyl, sulfonato, or sulfonatoalkyl. In a still more preferred aspect, at least two of the $R^{14}$ substituents are each independently sulfonato or sulfonatoalkyl. In a yet more preferred aspect, each of the $R^{14}$ substituents is sulfonato.

In one aspect, at least one pair of the $R^{14}$ substituents is the same (i.e., the $R^n$ substituent is not independently selected, but is the same as the other $R^n$ substituent). Alternatively, at least two pairs of the $R^{14}$ substituents are the same. More preferably, the dye is symmetric or pseudo-symmetric (i.e., the $R^{14}$ substituents on the dye indoline rings are also not independently selected, but each $R^{14}$ substituent is the same as the analogous $R^{14}$ substituents on the other ring).

In an alternative aspect, at least one $R^{14}$ substituent is hydrogen. Alternatively, exactly $R^{14}$ substituent is hydrogen. In a preferred aspect, at least one pair of $R^{14}$ substituents is hydrogen. Alternatively, exactly two, exactly three, or exactly four $R^{14}$ substituents are hydrogen. In another aspect, exactly four $R^{14}$ substituents are hydrogen.

In another alternative aspect, at least one $R^{14}$ substituent is sulfonato or sulfonatoalkyl. Alternatively, exactly one $R^{14}$ substituent is sulfonato or sulfonatoalkyl. In still another aspect, at least one pair of $R^{14}$ substituents is each a member independently selected from the group of sulfonato or sulfonatoalkyl. Alternatively, exactly one, exactly two, exactly three, or exactly four $R^{14}$ substituents are each a member independently selected from the group of sulfonato or sulfonatoalkyl.

In another alternative aspect, at least one $R^{14}$ substituent is anionic at physiological pH (e.g., sulfonato —$SO_3^-$, carboxy —$CO_2^-$). Alternatively, exactly one $R^{14}$ substituent is anionic at physiological pH. In still another aspect, at least one pair of $R^{14}$ substituents is anionic at physiological pH. Alternatively, exactly one, exactly two, exactly three, or exactly four $R^{14}$ substituents are anionic at physiological pH.

In another alternative aspect, at least one $R^{14}$ substituent is zwitterionic at physiological pH (e.g., an alkyl group with anionic sulfonato —$SO_3^-$ and a cationic trialkylammonium group substituents). Alternatively, exactly one $R^{14}$ substituent is zwitterionic at physiological pH. In still another aspect, at least one pair of $R^{14}$ substituents is zwitterionic at physiological pH. Alternatively, exactly one, exactly two, exactly three, or exactly four $R^{14}$ substituents are zwitterionic at physiological pH.

In another alternative aspect, at least one $R^{14}$ substituent is halo. Alternatively, exactly one $R^{14}$ substituent is halo. Alternatively, exactly two, exactly three, or exactly four $R^{14}$ substituents are halo.

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom. In a preferred aspect, L is not present. Alternatively, L is a $C_1$-$C_{10}$ alkylene interrupted by one or more ether linkages (e.g., a polyethylene glycol oligomer).

Y is an optional member selected from the group of a bond, —O—, —S—, —NH—, —NHC(O)—, —C(O)NH—, —$NR^{15}$—, —$NR^{15}$C(O)—, —C(O)$NR^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is an independently selected $C_1$-$C_{10}$ alkyl that is additionally substituted with one member from the group of $R^{15}$ and $R^{16}$; wherein the alkyl is optionally interrupted by at least one heteroatom. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is a bond; Z is $(CH_2)_tR^{13}$; $R^{13}$ is carboxyl or activated acyl; and t is an integer from 1 to 10, such as 1, 2, 3, 4, 5, 6, 7, 8, 9, or 10. Alternatively, t is an integer from 0 to 10.

In still another alternative preferred aspect, the Z group's L group is a bond. Alternatively, Z is $R^{13}$ or $R^{16}$ that is directly bonded to the phenyl ring itself if L and Y are also bonds.

In yet still another alternative preferred aspect, -L-Y—Z has at least four carbons. Alternatively, Z has at least four carbons.

$R^{15}$ is a member selected from the group of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

Each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

In certain instances, the compounds of Formula II have the formula:

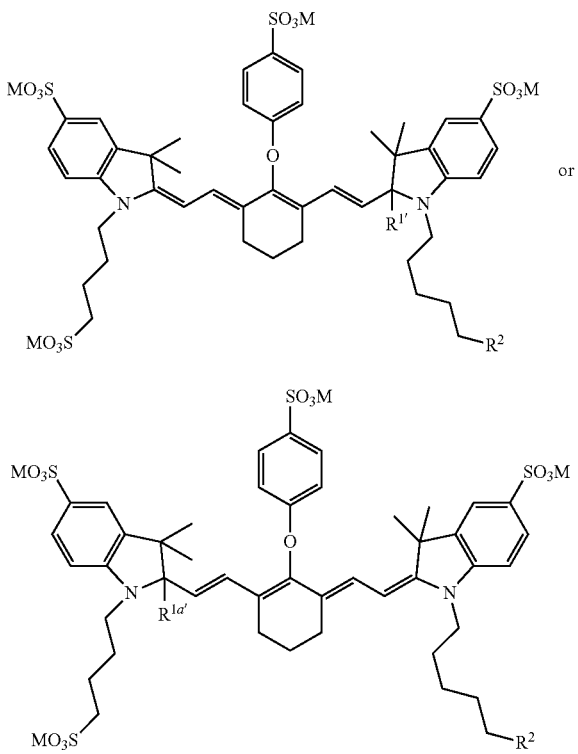

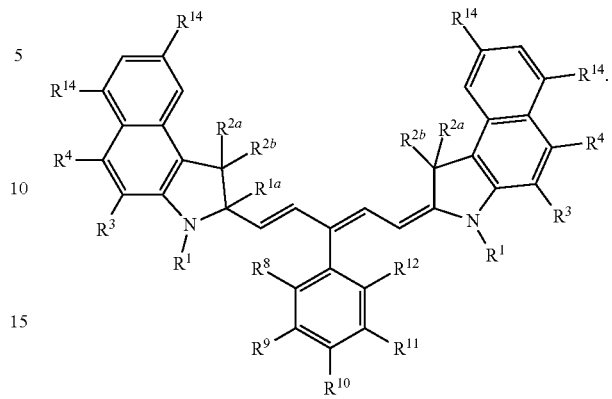

wherein $R^{1'}$ and $R^{1a'}$ are each independently hydrogen or deuterium, M is an alkali metal cation, and $R^2$ is $CO_2H$ or $CO_2M$. Preferably, M is $Na^+$.

In the oxidized state, the parent compound has a balanced charge. In a preferred aspect, the compound's net anionic charge in the oxidized state is balanced by alkali metal counterions (e.g., sodium or potassium). In a preferred aspect, in the oxidized state, at least one of the counterions is sodium. Alternatively, all of the counterions are sodium.

In one embodiment, the compound's net cationic charge in the oxidized state is balanced by organic anions (e.g., acetate, chloride, sulfonate, or formate). In a preferred aspect, in the oxidized state, at least one of the counterions is chloride or acetate. Alternatively, all of the counterions are chloride or acetate.

The compound may also incorporate covalent bonds to both cationic and anionic groups to produce a balanced charge. Embodiments of such compounds are set forth in U.S. Patent Publication No. 2012/0028291, which is incorporated by reference. In a preferred aspect, the compound's charge in the oxidized state is balanced by a combination of alkali metal counterions (e.g., sodium or potassium) and tetraalkylammonium substituents (e.g., a trimethylammonium substituent; a triethylammonium substituent; or a methyl diethylammonium substituent).

C. Compounds of Formula III

In one embodiment, the present invention provides a compound of Formula III:

$R^1$ is independently an alkyl group that is additionally substituted with from 0 to 1 $R^{13}$; wherein the alkyl group is optionally interrupted by at least one heteroatom (e.g., an ethyl, such as in a poly(ethylene glycol)) or an ionic group (e.g., a charged alkylammonium group, such as that in $-CH_2(NMe_2)CH_2CH_2CH_2-$). In a preferred aspect, $R^1$ is $C_2$-$C_{12}$ alkyl. In a alternative aspect, $R^1$ is $C_1$-$C_6$ alkyl (e.g., methyl). In a more preferred aspect, $R^1$ is $C_2$-$C_8$ alkyl. In a still more preferred aspect, $R^1$ is $C_2$-$C_6$ alkyl. In a yet still more preferred aspect, $R^1$ is ethyl, propyl, butyl, pentyl, or hexyl, and $R^1$ is additionally substituted with 1 $R^{13}$ (e.g., 3-sulfonylpropyl; 6-hydroxyhexyl).

In a preferred aspect, $R^1$ is $(CH_2)_rSO_3H$ or $(CH_2)_rSO_3^-$; and r is an integer from 1 to 20. In a more preferred aspect, r is 2, 3, or 4. Alternatively, $R^1$ is $(CH_2)_rOH$; and r is an integer from 2 to 6 (e.g., 6-hydroxyhexyl).

In one aspect, $R^1$ is an alkyl group that is additionally substituted with 1 $R^{13}$, wherein $R^{13}$ is selected from the group of hydroxyl, amino, carboxy, and sulfonato. In a more preferred aspect, the $R^{13}$ substituent of $R^1$ is carboxy or sulfonato. In a still more preferred aspect, the $R^{13}$ substituent of $R^1$ is sulfonato. In a yet still more preferred aspect, $R^1$ is sulfonatoethyl, sulfonatopropyl, sulfonatobutyl, or sulfonatopentyl.

In another alternative preferred aspect, $R^1$ is an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the reduced cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl.

$R^{1a}$ is either hydrogen or deuterium. Alternatively, $R^{1a'}$ is tritium.

$R^{2a}$ and $R^{2b}$ are each a member independently selected from the group of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl.

In a preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative preferred aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl.

$R^3$ and $R^4$ are each a member independently selected from the group of hydrogen, alkyl, alkenyl, halo, hydroxyl, alkoxy, cyano, carboxyl, alkoxycarbonyl, amido, amino, sulfonato, alkoxyalkyl, carboxyalkyl, alkoxycarbonylalkyl, and sulfonatoalkyl.

In a first aspect, $R^3$ and $R^4$ are each a member independently selected from the group of hydrogen, alkyl, alkenyl, halo, alkoxy, cyano, carboxyl, alkoxycarbonyl, amido, amino, sulfonato, alkoxyalkyl, carboxyalkyl, alkoxycarbonylalkyl, and sulfonatoalkyl. In a preferred aspect, $R^3$ and $R^4$ are each a member independently selected from the group of hydrogen, alkyl, carboxy, carboxyalkyl, sulfanato, and sulfanatoalkyl. In a more preferred embodiment, $R^3$, and $R^4$ are each a member independently selected from the group of hydrogen and sulfanato.

In another alternative aspect, at least one member of the group $R^3$ and $R^4$ is sulfonato or sulfonatoalkyl. Alternatively, exactly one substituent selected from the group $R^3$ and $R^4$ is sulfonato or sulfonatoalkyl. In a preferred aspect, $R^3$ is sulfonato. In still another aspect, $R^3$ and $R^4$ is selected independently from the group of sulfonato or sulfonatoalkyl. Alternatively, exactly two members of the group $R^3$ and $R^4$ are sulfonato or sulfonatoalkyl.

In another alternative aspect, at least one member of the group $R^3$ and $R^4$ is anionic at physiological pH (e.g., sulfonato $—SO_3^-$, carboxy $—CO_2^-$). Alternatively, exactly two members of the group $R^3$ and $R^4$ are anionic at physiological pH.

$R^8$ and $R^9$ are each a member independently selected from the group of hydrogen, alkyl, alkenyl, halo, alkoxy, sulfonato, and -L-Y—Z; wherein exactly one member selected from the group of $R^8$ and $R^9$ is -L-Y—Z.

In one aspect, $R^8$ is -L-Y—Z. Alternatively, $R^9$ is -L-Y—Z.

In a second aspect, $R^8$ is hydrogen, alkyl, alkoxy, or halo. In a preferred aspect, $R^8$ is hydrogen. In another preferred aspect, $R^8$ is fluoro.

Alternatively, $R^9$ is hydrogen, alkyl, alkoxy, or halo. In a more preferred aspect, $R^9$ is 5-carboxypentyl. Alternatively, $R^9$ is 4-carboxybutyl.

$R^{10}$, $R^{11}$, and $R^{12}$ are each a member independently selected from the group of hydrogen, alkyl, alkenyl, halo, alkoxy, and sulfonato.

In a first aspect, $R^{10}$ is hydrogen, alkyl, alkoxy, or halo. In a more preferred aspect, $R^{10}$ is hydrogen. Alternatively, $R^{10}$ is fluoro.

In a second aspect, $R^{11}$ is hydrogen, alkyl, alkoxy, or halo. In a more preferred aspect, $R^{11}$ is hydrogen. Alternatively, $R^{11}$ is fluoro. In a still more preferred aspect, $R^{10}$ and $R^{11}$ are hydrogen.

In a third aspect, $R^{12}$ is hydrogen, alkyl, alkoxy, or halo. In a more preferred aspect, $R^{12}$ is hydrogen. Alternatively, $R^{12}$ is fluoro. In a still more preferred aspect, $R^{10}$ and $R^{12}$ are hydrogen. Alternatively, $R^{11}$ and $R^{12}$ are hydrogen. In a yet still more preferred aspect, $R^{10}$, $R^{11}$, and $R^{12}$ are hydrogen.

In a fourth aspect, the phenyl ring substituted with $R^8$, $R^9$, $R^{10}$, $R^{11}$, and $R^{12}$ is 1,2,3-substituted with independently selected substituents other than hydrogen, and the 1-substituent is the polymethine bridge (e.g., $R^8$ is -L-Y—Z and $R^9$ is alkyl; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted.

In a fifth aspect, the phenyl ring substituted with $R^8$, $R^9$, $R^{10}$, $R^{11}$, and $R^{12}$ is 1,2,3,4-substituted with independently selected substituents other than hydrogen, and the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, and the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

In a seventh aspect, $R^8$, $R^{10}$, $R^{11}$, and $R^{12}$ are each a member independently selected from the group of hydrogen, alkyl, halo, and sulfonato.

In an eighth aspect, the combination of the phenyl ring and its substituents $R^8$, $R^9$, $R^{10}$, $R^{11}$, and $R^{12}$ has at least ten carbons.

Fluoro substitution has been shown to increase quantum yield and photostability in fluorescein dyes as well as lowering dye $pK_a$ (see Sun, W.-C. et al. *J. Org. Chem.* 1997, 62, 6469-6475). In an eighth aspect, at least one member of the group $R^8$, $R^9$, $R^{10}$, $R^{11}$, and $R^{12}$ is a fluoro substituent. Alternatively, at least one member of the group $R^3$, $R^4$, $R^5$, $R^6$, and $R^{14}$ is a fluoro substituent. In yet another aspect, at least two members of $R^3$, $R^4$, $R^5$, $R^6$, $R^8$, $R^9$, $R^{10}$, $R^{11}$, $R^{12}$, and $R^{14}$ are fluoro substituents. In yet another aspect, at least three members of $R^3$, $R^4$, $R^5$, $R^6$, $R^8$, $R^9$, $R^{10}$, $R^{11}$, $R^{12}$, and $R^{14}$ are fluoro substituents.

Each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato. Alternatively, $R^{13}$ is hydrogen.

Each $R^{14}$ is a member independently selected from the group of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 1 $R^{13}$. Alternatively, each $R^{14}$ is a member independently selected from the group of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 2 $R^{13}$. Alternatively, each $R^{14}$ is a member independently selected from the group of alkyl, alkenyl, halo, hydrogen, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 2 $R^{13}$.

In a preferred aspect, $R^{14}$ is alkyl, alkenyl, carboxyl, alkoxycarbonyl, amido, or alkoxycarbonylalkyl. Alternatively, $R^{14}$ is sulfonato. Alternatively, $R^{14}$ is hydroxy. In a more preferred aspect, $R^{14}$ is alkyl or alkyl substituted with 1 $R^{13}$. Alternatively, $R^{14}$ is carboxyalkyl, hydroxyalkyl, or sulfonatoalkyl.

In one aspect, the $R^{14}$ substituents are each independently, carboxy, carboxyalkyl, sulfonato, or sulfonatoalkyl. In a still more preferred aspect, the $R^{14}$ substituents are each independently sulfonato or sulfonatoalkyl. In a yet more preferred aspect, each of the $R^{14}$ substituents is sulfonato.

Alternatively, each $R^{14}$ is a member independently selected from the group of alkyl, alkenyl, halo, hydrogen, hydroxyl, alkoxy, amino, cyano, carboxyl, alkoxycarbonyl, amido, sulfonato, alkoxycarbonylalkyl, and alkoxyalkyl; wherein the $R^{14}$ alkyl is additionally substituted with from 0 to 1 $R^{13}$.

In one aspect, at least one pair of the $R^{14}$ substituents is the same (i.e., the $R''$ substituent is not independently selected, but is the same as the other $R''$ substituent). Alternatively, at least two pairs of the $R^{14}$ substituents are the same. More preferably, the dye is symmetric or pseudo-symmetric (i.e., the $R^{14}$ substituents on the dye indoline rings are also not independently selected, but each $R^{14}$ substituent is the same as the analogous $R^{14}$ substituents on the other ring).

In an alternative aspect, at least one $R^{14}$ substituent is hydrogen. Alternatively, exactly $R^{14}$ substituent is hydrogen. In a preferred aspect, at least one pair of $R^{14}$ substituents is hydrogen. Alternatively, exactly two, exactly three, or exactly four $R^{14}$ substituents are hydrogen. In another aspect, exactly four $R^{14}$ substituents are hydrogen.

In another alternative aspect, at least one $R^{14}$ substituent is sulfonato or sulfonatoalkyl. Alternatively, exactly one $R^{14}$ substituent is sulfonato or sulfonatoalkyl. In still another aspect, at least one pair of $R^{14}$ substituents is each a member independently selected from the group of sulfonato or sulfonatoalkyl. Alternatively, exactly one, exactly two, exactly three, or exactly four $R^{14}$ substituents are each a member independently selected from the group of sulfonato or sulfonatoalkyl.

In another alternative aspect, at least one $R^{14}$ substituent is anionic at physiological pH (e.g., sulfonato —$SO_3^-$, carboxy —$CO_2^-$). Alternatively, exactly one $R^{14}$ substituent is anionic at physiological pH. In still another aspect, at least one pair of $R^{14}$ substituents is anionic at physiological pH. Alternatively, exactly one, exactly two, exactly three, or exactly four $R^{14}$ substituents are anionic at physiological pH.

In an alternative aspect, at least one $R^{14}$ substituent is zwitterionic at physiological pH (e.g., an alkyl group with anionic sulfonato —$SO_3^-$ and a cationic trialkylammonium group substituents). Alternatively, exactly one $R^{14}$ substituent is zwitterionic at physiological pH. In still another aspect, at least one pair of $R^{14}$ substituents is zwitterionic at physiological pH. Alternatively, exactly one, exactly two, exactly three, or exactly four $R^{14}$ substituents are zwitterionic at physiological pH.

In another alternative aspect, at least one $R^{14}$ substituent is halo. Alternatively, exactly one $R^{14}$ substituent is halo. Alternatively, exactly two, exactly three, or exactly four $R^{14}$ substituents are halo.

In one aspect, at least one pair of $R^1$, $R^{2a}$, $R^{2b}$, $R^3$, $R^4$, or $R^{14}$ is the same (i.e., the $R''$ substituent is not independently selected, but is the same as the other $R''$ substituent). This aspect can be combined with other aspects specifying the number or type of dye substituents (e.g., exactly two members of the groups $R^3$, $R^4$, and $R^{14}$ are hydrogen, and the two members are the pair of $R^4$s). Alternatively, at least two, at least three, or all four pairs of $R^1$, $R^{2a}$, $R^{2b}$, $R^3$, $R^4$, or $R^{14}$ are the same. More preferably, the dye is symmetric or pseudo-symmetric (i.e., $R^1$, $R^{2a}$, and $R^{2b}$ are also not independently selected, but are the same as the other $R^1$, $R^{2a}$, and $R^{2b}$ substituents).

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom. In a preferred aspect, L is not present. Alternatively, L is a $C_1$-$C_{10}$ alkylene interrupted by ether linkages (e.g., a polyethylene glycol oligomer).

Y is an optional member selected from the group of a bond, —O—, —S—, —NH—, —NHC(O)—, —C(O)NH—, —$NR^{15}$—, —$NR^{15}$C(O)—, —C(O)$NR^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is an independently selected $C_1$-$C_{10}$ alkyl that is additionally substituted with one member from the group of $R^{13}$ and $R^{16}$; wherein the alkyl is optionally interrupted by at least one heteroatom. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is a bond; Z is $(CH_2)_tR^{13}$; $R^{13}$ is carboxyl or activated acyl; and t is an integer from 1 to 10, such as 1, 2, 3, 4, 5, 6, 7, 8, 9, or 10. Alternatively, t is an integer from 0 to 10.

In still another alternative preferred aspect, the Z group's L group is a bond. Alternatively, Z is $R^{13}$ or $R^{16}$ that is directly bonded to the phenyl ring itself if L and Y are also bonds.

In yet still another alternative preferred aspect, -L-Y—Z has at least four carbons. Alternatively, Z has at least four carbons.

$R^{15}$ is a member selected from the group of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

Each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

In an alternative embodiment that may incorporate one or more of the aspects described, the present invention provides a compound of Formula III':

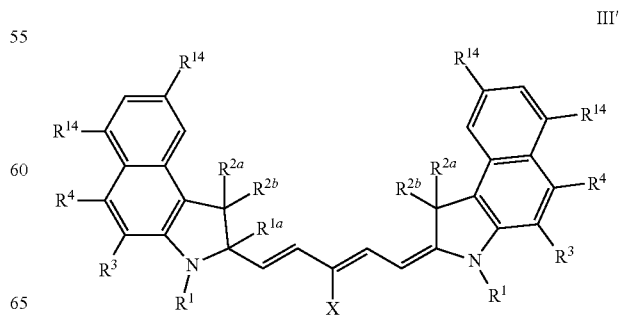

III'

X is hydrogen, halo, alkyl, cycloalkyl, heterocycloalkyl, aryl, heteroaryl, alkenyl, or alkynyl. Preferably, X is hydrogen, halo, alkyl, or aryl. Preferably, X is or comprises an -L-Y—Z moiety. Alternatively, X is or comprises an $R^L$ moiety.

In one embodiment of the oxidized state, the compound has a balanced charge. In a preferred aspect, the compound's net anionic charge in the oxidized state is balanced by alkali metal counterions (e.g., sodium or potassium). In a preferred aspect, in the oxidized state, at least one of the counterions is sodium. Alternatively, all of the counterions are sodium.

In one embodiment, the compound's net cationic charge in the oxidized state is balanced by organic anions (e.g., acetate, chloride, sulfonate, or formate). In a preferred aspect, in the oxidized state, at least one of the counterions is chloride or acetate. Alternatively, all of the counterions are chloride or acetate.

The compound may also incorporate covalent bonds to both cationic and anionic groups to produce a balanced charge. Embodiments of such compounds are set forth in U.S. Patent Publication No. 2012/0028291, which is incorporated by reference. In a preferred aspect, the compound's charge in the oxidized state is balanced by a combination of alkali metal counterions (e.g., sodium or potassium) and tetraalkylammonium substituents (e.g., a trimethylammonium substituent; a triethylammonium substituent; or a methyl diethylammonium substituent).

In a preferred aspect, the compound of Formula III has the formula:

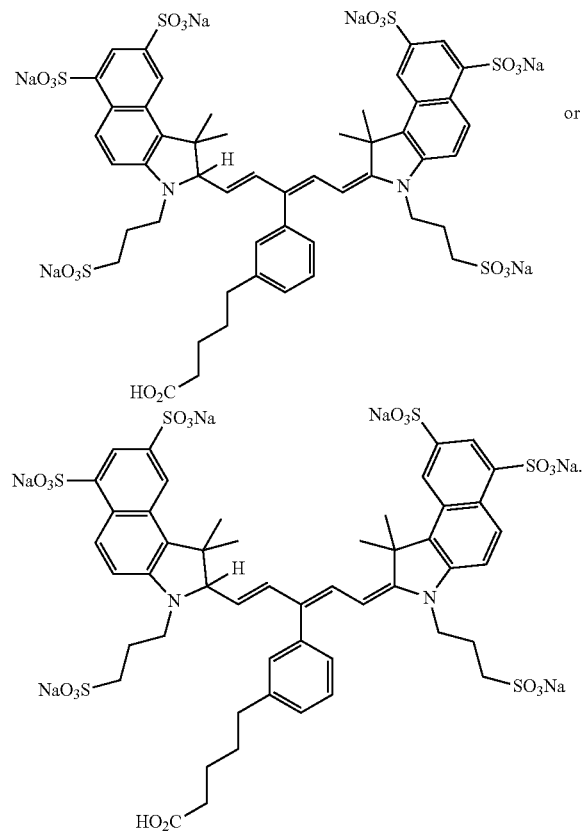

Alternatively, in certain aspects, an activated acyl group is present in place of the carboxy group. In a still more preferred aspect, the activated acyl group is an activated ester. In a still yet more preferred aspect, the activated ester is a succinimidyloxy-ester.

The compound of Formula III is substantially non-fluorescent, but upon oxidation fluoresces at a wavelength within the range of about 550 nm to about 1000 nm. Preferably, the compound upon oxidation fluoresces at a wavelength within the range of about 600 nm to about 850 nm. More preferably, the compound upon oxidation fluoresces at a wavelength within the range of about 600 nm to about 725 nm. Alternatively, the compound upon oxidation fluoresces at a wavelength within the range of about 725 nm to about 850 nm.

D. Compounds of Formula IV

In another embodiment, the present invention provides a compound of Formula IVa or IVb:

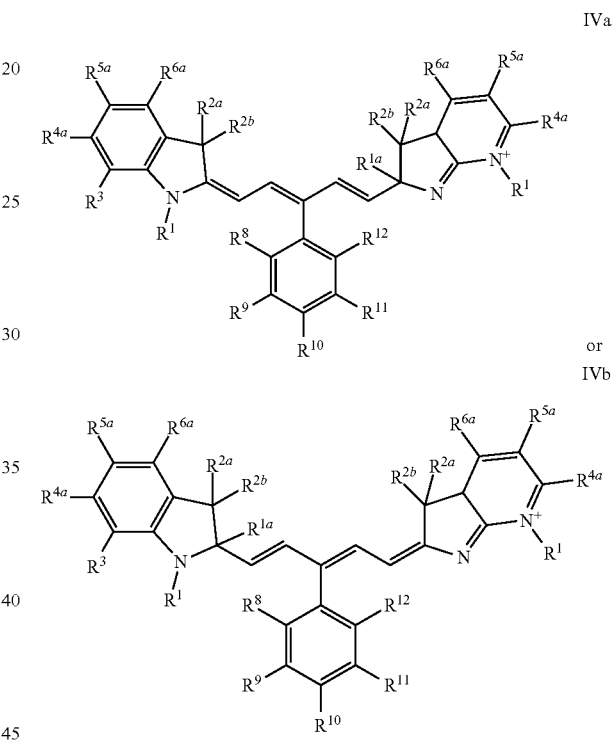

Each $R^1$ is independently a member selected from the group consisting of L-Y—Z and an alkyl group that is additionally substituted with from 0 to 1 $R^{13}$ and/or from 0 to 1 $R^{16}$; wherein the alkyl is optionally interrupted by at least one heteroatom (e.g., an ethyl, such as in a poly(ethylene glycol)) or an ionic group (e.g., a charged alkylammonium group, such as that in —$CH_2(NMe_2)$$CH_2CH_2CH_2$—).

In a preferred aspect, $R^1$ is $C_1$-$C_{20}$ alkyl. In a more preferred aspect, $R^1$ is $C_1$-$C_{12}$ or $C_2$-$C_8$ alkyl. In a still more preferred aspect, $R^1$ is $C_2$-$C_6$ alkyl. In a yet still more preferred aspect, $R^1$ is ethyl, propyl, butyl, or pentyl, and $R^1$ is additionally substituted with 1 $R^{13}$.

In a preferred aspect, $R^1$ is not interrupted by a heteroatom. Alternatively, $R^1$ is interrupted by at least one ether, thioether, substituted amino, or amido group.

In another preferred aspect, $R^1$ is $(CH_2)_rSO_3H$ or $(CH_2)_rSO_3^-$; and r is an integer from 1 to 20. In a more preferred aspect, r is 2, 3, or 4. Alternatively, $R^1$ is $(CH_2)_rOH$; and r is an integer from 2 to 6 (e.g., 6-hydroxyhexyl).

In still another preferred aspect, $R^1$ is an alkyl group that is additionally substituted with 1 $R^{13}$ that is selected from the group of hydroxyl, amino, carboxy, and sulfonato. In a more preferred aspect, the $R^{13}$ substituent of $R^1$ is carboxy or sulfonato. In a still more preferred aspect, the $R^{13}$ substituent of $R^1$ is sulfonato. In a yet still more preferred aspect, $R^1$ is sulfonatoethyl, sulfonatopropyl, sulfonatobutyl, or sulfonatopentyl.

In yet another preferred aspect, $R^1$ is an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the reduced cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl; more preferably, $R^1$ is 3-sulfonatopropyl.

$R^{1a}$ is either hydrogen or deuterium. Alternatively, $R^{1a'}$ is tritium.

In still another preferred aspect, $R^1$ is L—Y—Z. For example, L is a $C_1$-$C_{20}$ alkylene group such as $C_2$-$C_8$ alkylene; Y is a C(O)NH group; and Z is L-$R^{16}$, wherein L is a $C_1$-$C_{20}$ alkylene group such as $C_2$-$C_8$ alkylene and $R^{16}$ is a cycloalkynylcarbonyl like C(O)DBCO (see for example, compound 66). In another aspect, $R^1$ is L-Y—Z, wherein L is a $C_1$-$C_{20}$ alkylene group such as $C_2$-$C_8$ alkylene; Y is a C(O)NH group; and Z is L-$R^{16}$, wherein L is a $C_1$-$C_{20}$ alkylene group such as $C_2$-$C_8$ alkylene optionally interrupted by a heteroatom (e.g., ((CH$_2$CH$_2$O)$_3$—CH$_2$CH$_2$—) and $R^{16}$ is an azido group).

Each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 $R^{16}$.

In a preferred aspect, all $R^{2a}$ are the same substituent. Alternatively, all $R^{2b}$ are the same substituent. More preferably, all $R^{2a}$ are the same substituent, and all $R^{2b}$ are the same substituent.

In another preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl. Yet still more preferably, $R^{2a}$ is methyl.

Each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 $R^{16}$.

In a first aspect, each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, alkoxy, cyano, carboxyl, alkoxycarbonyl, amido, sulfonato, alkoxyalkyl, carboxyalkyl, alkoxycarbonylalkyl, and sulfonatoalkyl. In a preferred aspect, each $R^3$, $R^{4a}$, $R^{4b}$, $R^{5a}$, $R^{5b}$, $R^{6a}$, and $R^{6b}$ is a member independently selected from the group of hydrogen, alkyl, carboxy, carboxyalkyl, halo, sulfanato, and sulfanatoalkyl. In a more preferred embodiment, each $R^3$, $R^{4a}$, $R^{4b}$, $R^{5a}$, $R^{5b}$, $R^{6a}$, and $R^{6b}$ is a member independently selected from the group of hydrogen, halo, and sulfanato.

In an alternative aspect, at least one member of the group $R^3$, $R^{4a}$, $R^{4b}$, $R^{5a}$, $R^{5b}$, $R^{6a}$, and $R^{6b}$ is hydrogen. Alternatively, exactly one member of the group $R^3$, $R^{4a}$, $R^{4b}$, $R^{5a}$, $R^{5b}$, $R^{6a}$, and $R^{6b}$ is hydrogen. In a preferred aspect, at least one pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ is hydrogen. Alternatively, exactly two, exactly three, exactly four, exactly five, or exactly six members of the group $R^3$, $R^{4a}$, $R^{4b}$, $R^{5a}$, $R^{5b}$, $R^{6a}$, and $R^{6b}$ are hydrogen. In a more preferred aspect, exactly four members of the group $R^1$, $R^{4a}$, $R^{4b}$, $R^{5a}$, $R^{5b}$, $R^{6a}$, and $R^{6b}$ are hydrogen. Alternatively, exactly five members of the group $R^3$, $R^{4a}$, $R^{4b}$, $R^{5a}$, $R^{5b}$, $R^{6a}$, and $R^{6b}$ are hydrogen. In a still more preferred aspect, $R^3$, $R^{4a}$, $R^{6a}$, $R^{4b}$, and $R^{6b}$ are hydrogen.

In another alternative aspect, at least one member of the group $R^3$, $R^{4a}$, $R^{4b}$, $R^{5a}$, $R^{5b}$, $R^{6a}$, and $R^{6b}$ is sulfonato or sulfonatoalkyl. Alternatively, exactly one substituent selected from the group $R^3$, $R^{4a}$, $R^{4b}$, $R^{5a}$, $R^{5b}$, $R^{6a}$, and $R^{6b}$ is sulfonato or sulfonatoalkyl. In a preferred aspect, $R^{5a}$ is sulfonato. In still another aspect, both members of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ are each a member independently selected from the group of sulfonato or sulfonatoalkyl. Alternatively, exactly two, exactly three, exactly four, exactly five, or exactly six members of the group $R^3$, $R^{4a}$, $R^{4b}$, $R^{5a}$, $R^{5b}$, $R^{6a}$, and $R^{6b}$ are each a member independently selected from the group of sulfonato or sulfonatoalkyl.

In another alternative aspect, at least one member of the group $R^3$, $R^{4a}$, $R^{4b}$, $R^{5a}$, $R^{5b}$, $R^{6a}$, and $R^{6b}$ is anionic at physiological pH (e.g., sulfonato —SO$_3^-$, carboxyl —CO$_2^-$). Alternatively, exactly one member of the group $R^3$, $R^{4a}$, $R^{4b}$, $R^{5a}$, $R^{5b}$, $R^{6a}$, and, and $R^{6b}$ is anionic at physiological pH. In a preferred aspect, $R^{5a}$ is anionic at physiological pH. In still another aspect, each member of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ is anionic at physiological pH. Alternatively, exactly two, exactly three, exactly four, exactly five, or exactly six members of the group $R^3$, $R^{4a}$, $R^{4b}$, $R^{5a}$, $R^{5b}$, $R^{6a}$, and, and $R^{6b}$ are anionic at physiological pH. exactly two, exactly three, or exactly four members of the group $R^3$, $R^{4a}$, $R^{4b}$, $R^{5a}$, $R^{5b}$, $R^{6a}$, and, and $R^{6b}$ are anionic at physiological pH.

In another alternative aspect, at least one member of the group $R^3$, $R^{4a}$, $R^{4b}$, $R^{5a}$, $R^{5b}$, $R^{6a}$, and, and $R^{6b}$ is halo. Alternatively, exactly one substituent selected from the group $R^3$, $R^{4a}$, $R^{4b}$, $R^{5a}$, $R^{5b}$, $R^{6a}$, and, and $R^{6b}$ is halo. In a preferred aspect, $R^{5b}$ is halo; more preferably, $R^{5b}$ is chloro. In still another aspect, both members of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ are each an independently selected halo. Alternatively, exactly two, exactly three, exactly four, exactly five, or exactly six members of the group $R^3$, $R^{4a}$, $R^{4b}$, $R^{5a}$, $R^{5b}$, $R^{6a}$, and, and $R^{6b}$ are each an independently selected halo.

$R^8$, $R^9$, $R^{10}$, $R^{11}$ and $R^{12}$ are each a member independently selected from the group consisting of hydrogen, alkyl, alkenyl, halo, alkoxy, sulfonato, sulfonatoalkyl, hydroxyl, amino, carboxyl, alkoxycarbonyl, cyano, amido, thioacetyl, and -L-Y—Z; wherein, if present, at least one member selected from the group consisting of $R^8$, $R^9$, and $R^{10}$ is -L-Y—Z.

In one aspect, $R^8$ is -L-Y—Z. Preferably, $R^9$, $R^{10}$, $R^{11}$, and $R^{12}$ are each a member independently selected from the group consisting of hydrogen, alkyl, halo, sulfonato, and sulfonatoalkyl.

In a second aspect, $R^8$ is hydrogen, alkyl, alkoxy, or halo. In a more preferred aspect, $R^8$ is hydrogen.

Alternatively, $R^8$ is a carboxyalkyl. Preferably, $R^8$ is a lower alkyl group with a carboxyl substituent. More preferably, $R^8$ is 5-carboxypentyl, 4-carboxybutyl, 3-carboxypropyl, 2-carboxyethyl, or carboxymethyl. Still more preferably, $R^8$ is 5-carboxypentyl or 2-carboxyethyl.

Alternatively, $R^8$ is carboxyl, alkoxycarbonyl, or amido; more preferably, $R^8$ is carboxyl.

In one aspect, $R^{10}$ is -L-Y—Z. Preferably, $R^8$, $R^9$, $R^{11}$, and $R^{12}$ are each a member independently selected from the group consisting of hydrogen, alkyl, halo, sulfonato, and sulfonatoalkyl.

In a second aspect, $R^{10}$ is hydrogen, alkyl, alkoxy, or halo. In a more preferred aspect, $R^{10}$ is hydrogen.

Alternatively, $R^{10}$ is a carboxyalkyl. Preferably, $R^{10}$ is a lower alkyl group with a carboxyl substituent. More preferably, $R^{10}$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl.

Alternatively, $R^{10}$ is carboxyl, alkoxycarbonyl, or amido; more preferably, $R^{10}$ is carboxyl.

In one aspect, $R^9$ is -L-Y—Z. Preferably, $R_8$, $R^{10}$, $R^{11}$, and $R^{12}$ are each a member independently selected from the group consisting of hydrogen, alkyl, halo, sulfonato, and sulfonatoalkyl.

In a second aspect, $R^9$ is hydrogen, alkyl, alkoxy, or halo. In a more preferred aspect, $R^9$ is hydrogen.

Alternatively, $R^9$ is a carboxyalkyl. Preferably, $R^9$ is a lower alkyl group with a carboxyl substituent. More preferably, $R^9$ is 5-carboxypentyl, 4-carboxybutyl, 3-carboxypropyl, 2-carboxyethyl, or carboxymethyl. Still more preferably, $R^9$ is 5-carboxypentyl or 2-carboxyethyl.

Alternatively, $R^9$ is carboxyl, alkoxycarbonyl, or amido; more preferably, $R^9$ is carboxyl.

In one aspect, $R^{11}$ and $R^{12}$ are each a member independently selected from the group of hydrogen, alkyl, alkenyl, halo, alkoxy, sulfonato, hydroxyl, amino, carboxyl, alkoxycarbonyl, cyano, amido, thioacetyl, and -L-Y—Z. Preferably, $R^{11}$ and $R^{12}$ are each a member independently selected from the group of hydrogen, alkyl, halo, sulfonato, and sulfonatoalkyl. More preferably, $R^{11}$ and $R^{12}$ are each a member independently selected from the group of hydrogen, halo, and sulfonato.

In a second aspect, $R^{11}$ is hydrogen, alkyl, alkoxy, or halo. In a more preferred aspect, $R^{11}$ is hydrogen. In a still more preferred aspect, $R^{10}$ and $R^{11}$ are hydrogen.

In a third aspect, $R^{12}$ is hydrogen, alkyl, alkoxy, or halo. In a more preferred aspect, $R^{12}$ is hydrogen. In a still more preferred aspect, $R^{10}$ and $R^{12}$ are hydrogen. Alternatively, $R^{11}$ and $R^{12}$ are hydrogen. In a yet still more preferred aspect, $R^{10}$, $R^{11}$, and $R^{12}$ are hydrogen.

In a fourth aspect, the phenyl ring substituted with $R^8$, $R^9$, $R^{10}$, $R^{11}$, and $R^{12}$ is 1,2,3-substituted with independently selected substituents other than hydrogen, and the 1-substituent is the polymethine bridge (e.g., $R^8$ is -L-Y—Z and $R^9$ is alkyl; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted.

In a fifth aspect, the phenyl ring substituted with $R^8$, $R^9$, $R^{10}$, $R^{11}$, and $R^{12}$ is 1,2,3,4-substituted with independently selected substituents other than hydrogen, and the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, and the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

In a seventh aspect, $R^8$, $R^{10}$, $R^{11}$, and $R^{12}$ are each a member independently selected from the group of hydrogen, alkyl, halo, sulfonato, and sulfonatoalkyl.

In an eighth aspect, the combination of the phenyl ring and its substituents $R^8$, $R^9$, $R^{10}$, $R^{11}$, and $R^{12}$ has at least ten carbons.

Each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato.

Each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom. In a preferred aspect, L is a bond. Alternatively, L is a $C_1$-$C_{14}$ alkylene; more preferably, L is a $C_1$-$C_{10}$ alkylene or a $C_1$-$C_6$ alkylene. Alternatively, L is a $C_1$-$C_{12}$ alkylene interrupted by ether linkages (e.g., a polyethylene glycol oligomer).

In a preferred aspect, the alkylene or alkenylene is not interrupted by a heteroatom. Alternatively, L is interrupted by at least one ether, thioether, substituted amino, or amido group.

Each Y is an optional member independently selected from the group consisting of a bond, —O—, —S—, —NH—, —NHC(O)—, —C(O)NH—, —$NR^{15}$—, —$NR^{15}$C(O)—, —C(O)$NR^{15}$—, —N(Z)—, —N(Z)C(O)—, and —C(O)N(Z)—. In a preferred aspect, Y is a bond. Alternatively, Y is —O—. Alternatively, Y is an amido group optionally substituted with $R^{15}$ at the amido nitrogen.

Each Z is independently selected from the group consisting of -L-$R^{13}$ and -L-$R^{16}$. In a preferred aspect, the -L- is a $C_1$-$C_{20}$ alkylene; more preferably, a $C_1$-$C_{12}$ alkylene; and still more preferably, a $C_1$-$C_{10}$ alkylene. Alternatively, the -L- is a bond. Yet still more preferably, the -L- is $C_1$-$C_6$ alkyl. Alternatively, the -L- is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In an alternative preferred aspect, Z is a carboxyalkyl. Preferably, Z is a lower alkyl group with a carboxy-substituent. More preferably, Z is 5-carboxypentyl, 4-carboxybutyl, 3-carboxypropyl, 2-carboxyethyl, or carboxymethyl. Still more preferably, Z is 5-carboxypentyl or 2-carboxyethyl.

In another alternative preferred aspect, -L-Y— is a bond; Z is $(CH_2)_tR^{13}$, $R^{13}$ is carboxyl or activated acyl; and t is an integer from 0 to 10, such as 0, 1, 2, 3, 4, 5, 6, 7, 8, 9, or 10. Alternatively, t is an integer from 1 to 10.

In still another alternative preferred aspect, -L-Y— is a bond. More preferably, Z is directly bonded to the phenyl ring or the polymethylene bridge.

In still another alternative preferred aspect, the Z group's L group is a bond. Alternatively, Z is $R^{13}$ or $R^{16}$ that is directly bonded to the phenyl ring itself if L and Y are also bonds.

In yet still another alternative preferred aspect, -L-Y—Z has at least three carbons. Alternatively, Z has at least three carbons.

In an alternative embodiment, —Y—Z is a member selected from the group consisting of —$N(Z)_2$, —N(Z)C(O)Z, and —$C(O)N(Z)_2$, and the two Z groups may optionally be linked to form a cycloalkynyl group Each $R^{15}$ is a member independently selected from the group consisting of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

In a preferred aspect, the alkyl is not interrupted by a heteroatom. In a preferred aspect, $R^{15}$ is alkyl. In a more preferred aspect, $R^{15}$ is lower alkyl.

Alternatively, L is interrupted by at least one ether, thioether, substituted amino, or amido group. Preferably, $R^{15}$ is interrupted by at least one ether group (e.g., a polyethylene glycol oligomer).

Each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido, a pegylated alkynyl, a pegylated cycloalkynyl, an ortho substituted phosphinyl aryl ester (e.g., TPPME), a spirocycloalkynyl, and an ortho substituted phosphine oxide aryl ester.

The oxidized form of the compound has a balanced charge. In a preferred aspect, the oxidized compound's net anionic charge is balanced by alkali metal counterions (e.g., sodium or potassium). In a more preferred aspect, at least one of the counterions is sodium. Alternatively, all of the counterions are sodium.

In a more preferred aspect, the compound of Formula IVa or IVb has the formula:

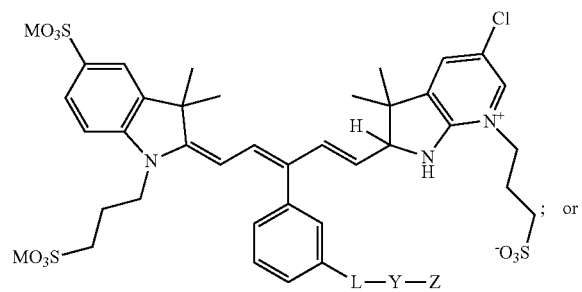

or

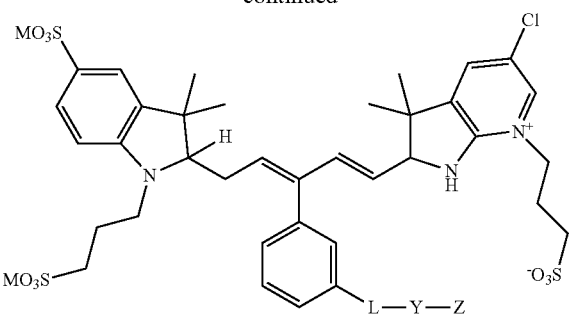

wherein M is a cationic counterion. More preferably, M is an alkali metal ion.

In certain aspects, an activated acyl group is present in place of the carboxy group. In a still more preferred aspect, the activated acyl group is an activated ester. In a still yet more preferred aspect, the activated ester is a succinimidyloxy-ester.

In a first aspect, the oxidized state of the compound of Formula IVa or IVb has a fluorescence absorption maximum at a wavelength within the range of about 550 nm to about 1000 nm. Preferably, the oxidized state of the compound has a fluorescence absorption maximum at a wavelength within the range of about 600 nm to about 1000 nm. More preferably, the oxidized state of the compound has a fluorescence absorption maximum at a wavelength within the range of about 600 nm to about 850 nm. Still more preferably, the oxidized state of the compound has a fluorescence absorption maximum at a wavelength within the range of about 600 nm to about 725 nm. Alternatively, the oxidized state of the compound has a fluorescence absorption maximum at a wavelength within the range of about 725 nm to about 850 nm.

In some embodiments, the parent compound's oxidized form has a balanced charge. In a preferred aspect, the compound's net anionic charge in the oxidized state is balanced by alkali metal counterions (e.g., sodium or potassium). In a preferred aspect, in the parent compound's oxidized state, at least one of the counterions is sodium. Alternatively, all of the counterions are sodium.

In one embodiment, the compound's net cationic charge in the oxidized state is balanced by organic anions (e.g., acetate, chloride, sulfonate, or formate). In a preferred aspect, in the parent compound's oxidized state, at least one of the counterions is chloride or acetate. Alternatively, all of the counterions are chloride or acetate.

The compound may also incorporate covalent bonds to both cationic and anionic groups to produce a balanced charge. Embodiments of such compounds are set forth in U.S. Patent Publication No. 2012/0028291, which is incorporated by reference. In a preferred aspect, the compound's charge in the oxidized state is balanced by a combination of alkali metal counterions (e.g., sodium or potassium) and tetraalkylammonium substituents (e.g., a trimethylammonium substituent; a triethylammonium substituent; or a methyl diethylammonium substituent).

E. Compounds of Formula V

In another embodiment, the present invention provides a compound of Formula V:

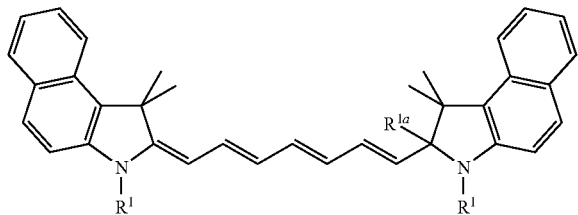

V

Each $R^1$ is independently a member selected from the group consisting of L-Y—Z and an alkyl group that is additionally substituted with from 0 to 1 $R^{13}$ and from 0 to 1 $R^{16}$; wherein the alkyl is optionally interrupted by at least one heteroatom (e.g., an ethyl, such as in a poly(ethylene glycol)) or an ionic group (e.g., a charged alkylammonium group, such as that in —CH$_2$(NMe$_2$)CH$_2$CH$_2$CH$_2$—).

In a preferred aspect, $R^1$ is $C_1$-$C_{20}$ alkyl. In a more preferred aspect, $R^1$ is $C_1$-$C_{12}$ or $C_2$-$C_8$ alkyl. In a still more preferred aspect, $R^1$ is $C_2$-$C_6$ alkyl. In a yet still more preferred aspect, $R^1$ is ethyl, propyl, butyl, or pentyl, and $R^1$ is additionally substituted with 1 $R^{13}$.

In a preferred aspect, $R^1$ is not interrupted by a heteroatom. Alternatively, $R^1$ is interrupted by at least one ether, thioether, substituted amino, or amido group.

In another preferred aspect, $R^1$ is (CH$_2$)$_r$SO$_3$H or (CH$_2$)$_r$SO$_3^-$; and r is an integer from 1 to 20. In a more preferred aspect, r is 2, 3, or 4. Alternatively, $R^1$ is (CH$_2$)$_r$OH; and r is an integer from 2 to 6 (e.g., 6-hydroxyhexyl).

In still another preferred aspect, $R^1$ is an alkyl group that is additionally substituted with 1 $R^{13}$ that is selected from the group of hydroxyl, amino, carboxy, and sulfonato. In a more preferred aspect, the $R^{13}$ substituent of $R^1$ is carboxy or sulfonato. In a still more preferred aspect, the $R^{13}$ substituent of $R^1$ is sulfonato. In a yet still more preferred aspect, $R^1$ is sulfonatoethyl, sulfonatopropyl, sulfonatobutyl, or sulfonatopentyl.

In yet another preferred aspect, $R^1$ is an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the reduced cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl; more preferably, $R^1$ is 3-sulfonatopropyl.

$R^{1a}$ is either hydrogen or deuterium. Alternatively, $R^{1a'}$ is tritium.

Each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato.

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom. In a preferred aspect, L is not present. Alternatively, L is a $C_1$-$C_{10}$ alkylene interrupted by ether linkages (e.g., a polyethylene glycol oligomer).

Y is an optional member selected from the group of a bond, —O—, —S—, —NH—, —NHC(O)—, —C(O)NH—, —NR$^{15}$—, —NR$^{15}$C(O)—, —C(O)NR$^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is an independently selected $C_1$-$C_{10}$ alkyl that is additionally substituted with one member from the group of $R^1$ and $R^{16}$; wherein the alkyl is optionally interrupted by at least one heteroatom. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is a bond; Z is (CH$_2$)$_t$R$^{13}$; $R^{13}$ is carboxyl or activated acyl; and t is an integer from 1 to 10 such as 1, 2, 3, 4, 5, 6, 7, 8, 9, or 10. Alternatively, t is an integer from 0 to 10.

In still another alternative preferred aspect, the Z group's L group is a bond. Alternatively, Z is $R^{13}$ or $R^{16}$ that is directly bonded to the phenyl ring itself if L and Y are also bonds.

In yet still another alternative preferred aspect, -L-Y—Z has at least four carbons. Alternatively, Z has at least four carbons.

$R^{15}$ is a member selected from the group of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

Each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

In one embodiment, the compound of Formula V has the formula:

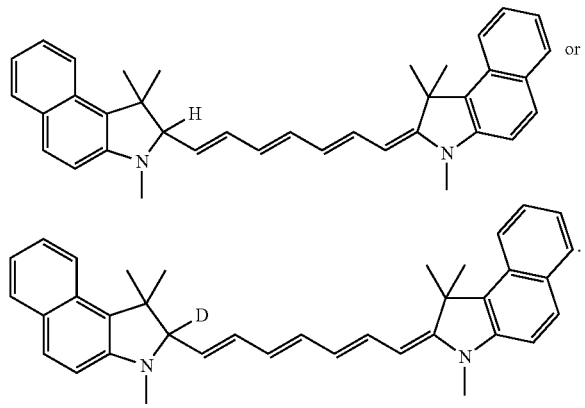

In still other embodiments, the present invention provides the following compounds:

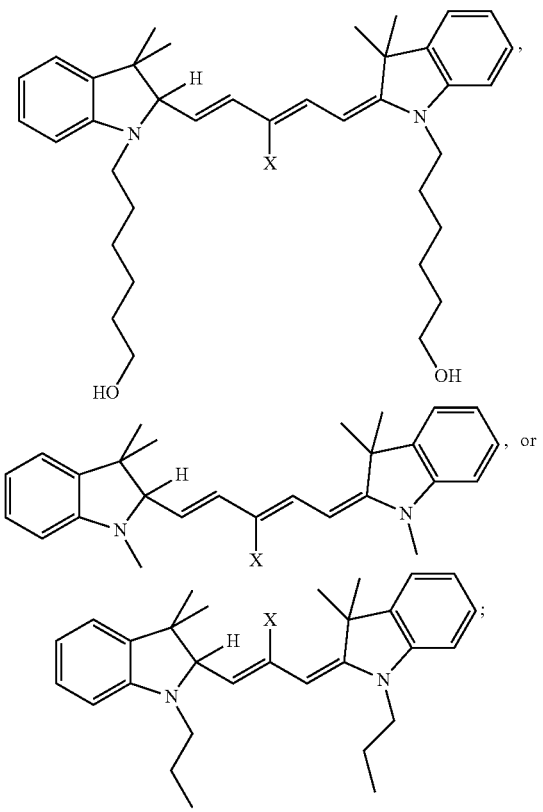

wherein X is hydrogen, halo, alkyl, cycloalkyl, heterocycloalkyl, aryl, heteroaryl, alkenyl, or alkynyl. Preferably, X is hydrogen, halo, alkyl, or aryl. Preferably, X is or comprises an -L-Y—Z moiety. Alternatively, X is or comprises an $R^L$ moiety. Alternatively, X is or comprises an ionic group (e.g., a charged alkylammonium group, such as that in —CH$_2$(NMe$_3$)).

F. Compounds of Formula VI

Hydrocyanine and deuterocyanine dyes as described in U.S. Patent Application Publication No. 2011/0070166 can be used in the methods of the invention. In some embodiments, for example, the hydro/deteurocyanine dye is a compound according to Formula VI (a):

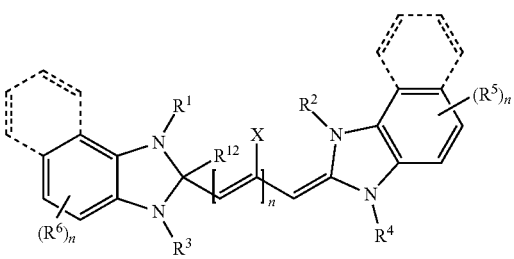

wherein X is hydrogen; halogen; $C_{1-20}$ alkyl; aryl; —OR, where R is $C_{1-20}$ alkyl or aryl; hydroxyl; —NR$^5$R$^6$, where $R^5$ and $R^6$ are independently hydrogen, $C_{1-20}$ alkyl or aryl; —CN, —SH; —NO$_2$; —S—$C_{1-20}$ alkyl; —S-aryl; aryl, —COOH; —COH; —COR or —COOR, where R is as defined above; or —CONR$^{13}$R$^{14}$, wherein $R^{13}$ and $R^{14}$ are independently hydrogen or R as defined above;

$R^1$-$R^4$ are independently hydrogen, $C_{1-20}$ alkyl, $C_{1-20}$ alkyl sulfate, $C_{1-20}$ alkyl carboxylate; $C_{1-20}$ alkyl amino; aryl, benzyl, oligoethylene glycol, L-Y—Z, an ionic group, or polyethylene glycol;

$R^5$ and $R^6$ are independently hydrogen; hydroxyl; —OR$^8$; —NH$_2$; —NHR$^9$; —NR$^{10}$R$^{11}$, $C_{1-20}$ alkyl, $C_{1-20}$ alkyl sulfonate, $C_{1-20}$ alkyl carboxylic acid or carboxylate; $C_{1-20}$ alkyl amino or quaternized amino; —COOH; —CO$_2^-$ or —SO$_3^-$; wherein $R^8$-$R^{11}$ are independently R as defined above; oligoethylene glycol, or polyethylene glycol;

n is an integer from 1-5;

$R^{12}$ is H or D;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —NR$^{15'}$—, —NR$^{15'}$C(O)—, —C(O)NR$^{15'}$—, —NZ—, —NZC(O)—, and —C(O)NZ—;

each Z is an independently selected $C_1$-$C_{10}$ alkyl that is additionally substituted with one member from the group of $R^{13'}$ and $R^{16'}$; wherein the alkyl is optionally interrupted by at least one heteroatom;

each $R^{13'}$ is a member independently selected from the group of hydroxyl, amino, carboxyl, alkoxycarbonyl, amido, sulfonato, and thioacetyl each $R^{15'}$ is a member independently selected from the group of alkyl and alkoxycarbonylalkyl; wherein the alkyl is optionally interrupted by at least one heteroatom; and each $R^{16'}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl.

In some embodiments, L is an optional member selected from the group of a bond, a $C_1$-$C_{10}$ alkylene, and a $C_1$-$C_{10}$ alkenylene; wherein the alkylene or alkenylene is optionally interrupted by at least one heteroatom or ionic group. In a preferred aspect, L is not present. Alternatively, L is a $C_1$-$C_{10}$ alkylene interrupted by ether linkages (e.g., a polyethylene glycol oligomer).

In some embodiments, Y is an optional member selected from the group of a bond, —O—, —S—, —NH—, —NHC(O)—, —C(O)NH—, —NR$^{15'}$—, —NR$^{15'}$C(O)—, —C(O)NR$^{15'}$—, —NZ—, —NZC(O)—, and —C(O)NZ—. In a preferred aspect, Y is a bond. Alternatively, Y is —O—. Alternatively, Y is an amido group optionally substituted with $R^{15'}$ at the amido nitrogen.

In some embodiments, each Z is an independently selected $C_1$-$C_{10}$ alkyl that is additionally substituted with one member from the group of $R^{13'}$ and $R^{16'}$; wherein the alkyl is optionally interrupted by at least one heteroatom or ionic group. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is a bond; Z is (CH$_2$)$_t$R$^{13'}$; $R^{13'}$ is carboxyl or activated acyl; and t is an integer from 1 to 10 such as 1, 2, 3, 4, 5, 6, 7, 8, 9, or 10. Alternatively, t is an integer from 0 to 10.

In still another alternative preferred aspect, the Z group's L group is a bond. Alternatively, Z is $R^{13'}$ or $R^{16'}$ that is directly bonded to the phenyl ring itself if L and Y are also bonds.

In yet still another alternative preferred aspect, -L—Y—Z has at least four carbons. Alternatively, Z has at least four carbons.

Each $R^{13'}$ is a member independently selected from the group of hydroxyl, amino, carboxyl, alkoxycarbonyl, amido, sulfonato, and thioacetyl. In a preferred embodiment, $R^{13'}$ is carboxyl, amido, or alkoxycarbonyl. In a more preferred embodiment, $R^{13'}$ is carboxyl. Alternatively, $R^{13'}$ is sulfonato.

In some embodiments, each $R^{15'}$ is a member independently selected from the group of alkyl and alkoxycarbonylalkyl; wherein the alkyl is optionally interrupted by at least one heteroatom or ionic group. In a preferred aspect, $R^{15'}$ is alkyl. In a more preferred aspect, $R^{15'}$ is lower alkyl. Alternatively, $R^{15'}$ is interrupted by ether linkages (e.g., a polyethylene glycol oligomer).

Each $R^{16'}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16'}$ is activated acyl, maleimidyl, phosphoramidityl, or glycidyl. In a more preferred embodiment, $R^{16'}$ is activated acyl. Alternatively, $R^{16'}$ is an activated ester. In a still more preferred embodiment, $R^{16'}$ is succinimidyloxy-ester or sulfosuccinimidyloxy-ester; and the benzene ring represented by dotted lines is optional.

In some embodiments, the hydro/deteurocyanine dye used in the methods of the invention is a compound according to Formula VI (b):

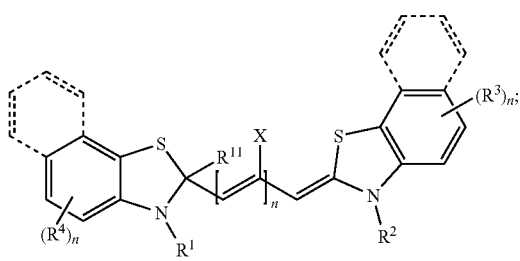

wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —NO2; —S—$C_{1-20}$ alkyl; —S-aryl; aryl, —COOH; —COH; —COR or —COOR, where R is as defined above; or —$CONR^{12}R^{13}$, wherein $R^{12}$ and $R^{13}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^1$ and $R^4$ are independently hydrogen; hydroxyl; —$OR^7$; —NH2; —$NHR^8$; —$NR^9R^{10}$, $C_{1-20}$ alkyl, $C_{1-20}$ alkyl sulfate, $C_{1-20}$ alkyl carboxylate; $C_{1-20}$ alkyl amino; —COOH; —CO2− or —SO3.−; wherein $R^7$-$R^{10}$ are independently R as defined above; oligoethylene glycol, or polyethylene glycol;

n is an integer from 1-5;

$R^{11}$ is H or D, and the benzene ring represented by dotted lines is optional.

In some embodiments, the hydro/deteurocyanine dye used in the methods of the invention is a compound according to Formula VI (c):

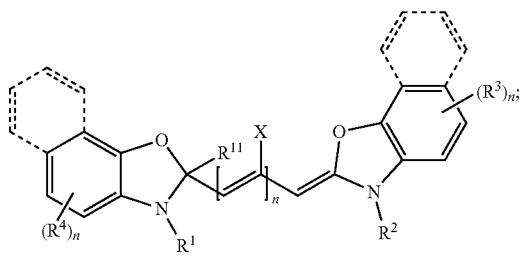

wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR^{12}R^{13}$, wherein $R^{12}$ and $R^{13}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^3$ and $R^4$ are independently hydrogen; hydroxyl; —$OR^7$; —$NH_2$; —$NHR^8$; —$NR^9R^{10}$, $C_{1-20}$ alkyl, $C_{1-20}$ alkyl sulfate, $C_{1-20}$ alkyl carboxylate; $C_{1-20}$ alkyl amino; —COOH; —$CO_2.^-$ or —$SO_3^-$; wherein $R^7$-$R^{10}$ are independently R as defined above; oligoethylene glycol, or polyethylene glycol;

n is an integer from 1-5;

$R^{11}$ is H or D; and the fused phenyl ring represented by dotted lines is optional.

In some embodiments, the hydro/deteurocyanine dye used in the methods of the invention is a compound according to Formula VI (d):

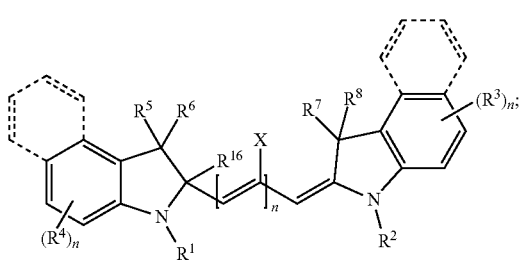

wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$, —S—$C_{1-20}$ alkyl; —S-aryl; aryl, —COOH; —COH; —COR or —COOR, where R is defined above; or —$CONR^{17}R^{18}$, wherein $R^{17}$ and $R^{18}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^3$ and $R^4$ are independently hydrogen; hydroxyl; —$OR^{12}$; —$NHR^{13}$; —$NR^{14}R^{15}$, $C_{1-20}$ alkyl, $C_{1-20}$ alkyl sulfate, $C_{1-20}$ alkyl carboxylate; $C_{1-20}$ alkyl amino; —COOH; —$CO_2^-$ or —$SO_3^-$; wherein $R^{12}$-$R^{15}$ are independently R as defined above; oligoethylene glycol, or polyethylene glycol;

$R^5$-$R^8$ are independently hydrogen or $C_{1-20}$ alkyl;

n is an integer from 1-5;

$R^{16}$ is H or D; and the benzene ring represented by dotted lines is optional, wherein if the benzene ring is not present, $R^{16}$ is D.

In some embodiments, the hydro/deteurocyanine dye used in the methods of the invention is a compound according to Formula VI (e):

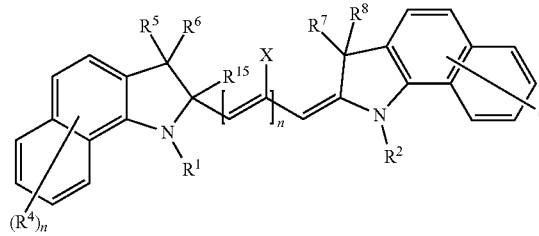

e wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$, —S—$C_{1-20}$ alkyl; —S-aryl; aryl, —COOH; —COH; —COR or —COOR, where R is defined above; or —$CONR^{16}R^{17}$, wherein $R^{16}$ and $R^{17}$ are independently hydrogen or R as defined above;

$R^1$ and $R^2$ are independently hydrogen, $C_{1-20}$ alkyl, $C_{1-20}$alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^3$ and $R^4$ are independently hydrogen; hydroxyl; —$OR^{11}$; —$NHR^{12}$; —$NR^{13}R^{14}$, $C_{1-20}$ alkyl, $C_{1-20}$ alkyl sulfate, $C_{1-20}$ alkyl carboxylate; $C_{1-20}$ alkyl amino; —COOH; —$CO_2^-$ or —$SO_3^-$; wherein $R^{11}$-$R^{14}$ are independently R as defined above; oligoethylene glycol, or polyethylene glycol;

$R^5$-$R^8$ are independently hydrogen or $C_{1-20}$ alkyl;

$R^{15}$ is H or D; and n is an integer from 1-5.

In some embodiments, the hydro/deteurocyanine dye used in the methods of the invention is a compound according to Formula VI (f):

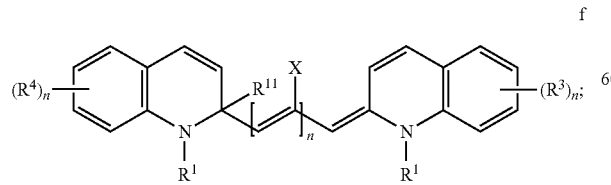

f wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR^{12}R^{13}$, wherein $R^{12}$ and $R^{13}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^3$ and $R^4$ are independently hydrogen; hydroxyl; —$OR^7$; —$NHR^8$; —$NR^9R^{10}$, $C_{1-20}$ alkyl, $C_{1-20}$ alkyl sulfate, $C_{1-20}$ alkyl carboxylate; $C_{1-20}$ alkyl amino; oligoethylene glycol, or polyethylene glycol; —COOH; —$CO_2^-$ or —$SO_3^-$; wherein $R^7$-$R^{10}$ are independently R as defined above;

$R^{11}$ is H or D; and n is an integer from 1-5.

In some embodiments, the hydro/deteurocyanine dye used in the methods of the invention is a compound according to Formula VI (g):

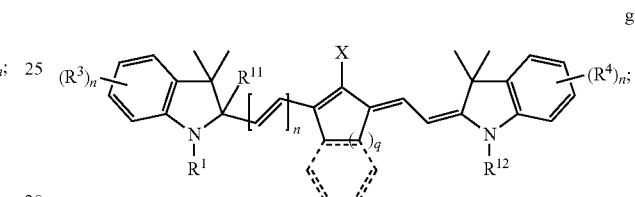

g wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR^{12}R^{13}$, wherein $R^{12}$ and $R^{13}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol; and $R^3$ and $R^4$ are independently hydrogen; hydroxyl; —$OR^7$; —$NHR^8$; —$NR^9R^{10}$, $C_{1-20}$ alkyl, $C_{1-20}$ alkyl sulfate, $C_{1-20}$ alkyl carboxylate; $C_{1-20}$ alkyl amino; —COOH; —$CO_2^-$ or —$SO_3^-$; wherein $R^7$-$R^{10}$ are independently R as defined above; oligoethylene glycol, or polyethylene glycol;

n is an integer from 1-5; and q is 0, 1, or 2.

In some embodiments, the hydro/deteurocyanine dye used in the methods of the invention is a compound according to formula VI (h):

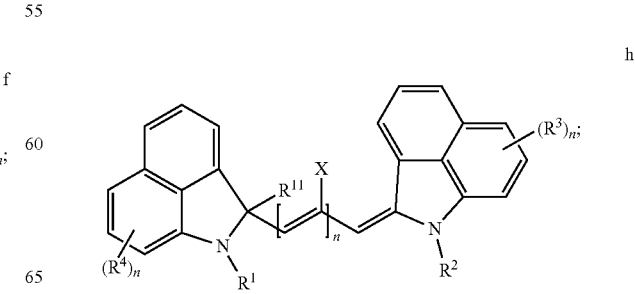

h wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR^{12}R^{13}$, wherein $R^{12}$ and $R^{13}$ are independently hydrogen or R as defined above;

$R^1$ and $R^2$ are independently hydrogen, $C_{1-20}$ alkyl, $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol; and $R^3$ and $R^4$ are independently hydrogen; hydroxyl; —$OR^7$; —$NHR^8$; —$NR^9R^{10}$, $C_{1-20}$ alkyl, $C_{1-20}$ alkyl sulfate, $C_{1-20}$ alkyl carboxylate; $C_{1-20}$ alkyl amino; —COOH; —$CO_2^-$ or —$SO_3^-$; wherein $R^7$-$R^{10}$ are independently R as defined above; oligoethylene glycol, or polyethylene glycol;

$R^{11}$ is D; and n is an integer from 1-5.

In some embodiments, the hydro/deteurocyanine dye used in the methods of the invention is a compound according to Formula VI (i):

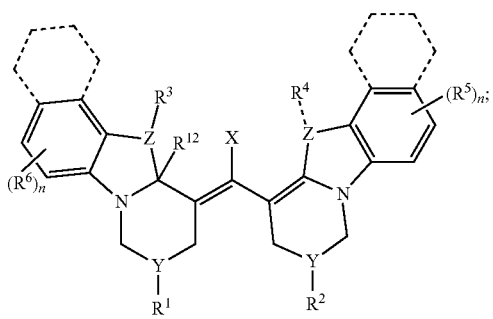

wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR^{13}R^{14}$, wherein $R^{13}$ and $R^{14}$ are independently hydrogen or R as defined above;

$R^1$-$R^4$ are independently hydrogen, $C_{1-20}$ alkyl; $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^5$ and $R^6$ are independently hydrogen; hydroxyl; —$OR^5$; —$NH_2$; —$NHR^6$; —$NR^7R^8$, $C_{1-20}$ alkyl; $C_{1-20}$ alkyl sulfate; $C_{1-20}$ alkyl carboxylate; $C_{1-20}$ alkyl amino; —COOH; —$CO_2^-$; or —$SO_3^-$; wherein $R^5$-$R^8$ are independently R as defined above; oligoethylene glycol, or polyethylene glycol;

Y and Z are independently carbon, nitrogen or sulfur, wherein if Y and/or Z is carbon, the carbon is tetravalent having two substituents as defined above; if Y and/or Z is sulfur; the sulfur is divalent; and if Y and/or Z is nitrogen, the nitrogen is trivalent, having one substituent as defined above;

$R^{12}$ is H or D; and the benzene ring represented by dotted lines is optional.

In some embodiments, the hydro/deteurocyanine dye used in the methods of the invention is a compound according to formula VI (j):

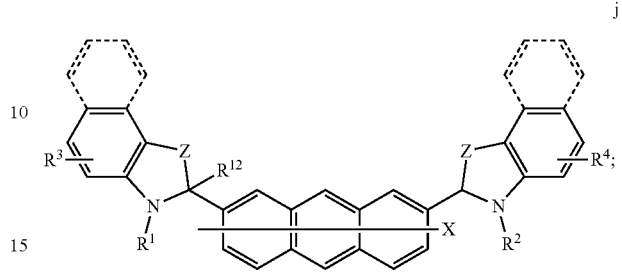

wherein X is hydrogen; halogen; $C_{1-20}$ alkyl; aryl; —OR, where R is $C_{1-20}$ alkyl or aryl; hydroxyl; —$NR^5R^6$, where $R^5$ and $R^6$ are independently hydrogen, $C_{1-20}$ alkyl or aryl; —CN, —SH; —$NO_2$; —S—$C_{1-20}$ alkyl; —S-aryl; —COOH; —COH; —COR or —COOR, where R is defined above; or —$CONR^{13}R^{14}$, wherein $R^{13}$ and $R^{14}$ are independently hydrogen or R as defined above;

$R^1$ and $R^2$ are independently hydrogen, $C_{1-20}$ alkyl; $C_{1-20}$ alkyl sulfonate, $C_{1-20}$ alkyl carboxylic acid or carboxylate; $C_{1-20}$ alkyl amino or quaternized amino; aryl, benzyl, oligoethylene glycol, L-Y—Z (as defined in VIa), an ionic group, or polyethylene glycol;

$R^3$ and $R^4$ are independently hydrogen; hydroxyl; —$OR^5$; —$NH_2$; —$NHR^6$; —$NR^7R^8$, $C_{1-20}$ alkyl; $C_{1-20}$ alkyl sulfonate, $C_{1-20}$ alkyl carboxylic acid or carboxylate; $C_{1-20}$ alkyl amino or quaternized amino; —COOH; —$CO_2^-$; or —$SO_3^-$; wherein $R^5$-$R^8$ are independent selected from the group consisting of $C_{1-20}$ alkyl or aryl; oligoethylene glycol, or polyethylene glycol;

Z is carbon, nitrogen, sulfur, or oxygen, wherein if Y and/or Z is carbon, the carbon is tetravalent having two substituents as defined above; if Y and/or Z is sulfur and/or oxygen; the sulfur and/or oxygen is divalent; and if Y and/or Z is nitrogen, the nitrogen is trivalent, having one substituent as defined above;

$R^{12}$ is H or D; and the benzene ring represented by dotted lines is optional.

G. Compounds of Formula VII

Hydrocyanine and deuterocyanine dyes as described in International Patent Publication No. WO 2012/061403 can be used in the methods of the invention. In some embodiments, for example, the hydro/deteurocyanine dye is a compound according to formula VII:

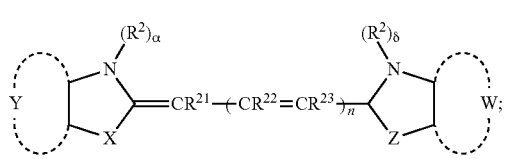

wherein Y represents the atoms necessary to form one to two fused aromatic rings having 6 atoms in each ring, wherein the Y atoms are selected from the group consisting of —CH, —C, —$CR^1$, and —$N(R^2)_\beta$, where β is 0 or 1, but no more than one of the atoms in Y is —$N(R^2)_\beta$, and each $R^1$ is independently amino, sulfo, trifluoromethyl, hydroxyl, halogen, carboxy, $C_1$-$C_6$ alkyl, $C_1$-$C_6$ alkoxy, $C_1$-$C_6$ alkylamino, or $C_2$-$C_{12}$ dialkylamino, wherein each alkyl portion of which is optionally substituted with substituents selected from the group consisting of carboxy, sulfo, amino, and hydroxy;

α is 1, and α+β=1 or 2;

W represents the atoms necessary to form one to two fused aromatic rings having 6 atoms in each ring, wherein the W atoms are selected from the group consisting of —CH, —C, —CR$^{1'}$, and —N(R$^{12}$)$_{β'}$, where β' is 0 or 1, but no more than one of the atoms in W is —N(R$^{12}$)$_{β'}$, and each R$^{1'}$ is independently amino, sulfo, trifluoromethyl, hydroxyl, halogen, carboxy, $C_1$-$C_6$ alkyl, $C_1$-$C_6$ alkoxy, $C_1$-$C_6$ alkylamino, or $C_2$-$C_{12}$ dialkylamino, wherein each alkyl portion of which is optionally substituted with substituents selected from the group consisting of carboxy, sulfo, amino, and hydroxy;

δ is 1, and δ+β'=1 or 2;

R$^2$ and R$^{12}$ are independently L-Y—Z, an ionic group, alkoxycarbonylalkyl, alkoxythiocarbonylalkyl, thioalkoxycarbonylalkyl, alkenoxycarbonylalkyl, alkenoxythiocarbonylalkyl, thioalkenoxycarbonylalkyl, alkoxycarbonylalkenyl, alkoxycarbonylalkenyl, thioalkoxycarbonylalkenyl, each alkyl or alkenyl portion of which is $C_1$-$C_{22}$ alkyl or alkenyl that optionally incorporates up to six hetero atoms, selected from N, O and S, and each alkyl portion of which is optionally substituted one or more times with F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, or $C_3$-$C_{18}$ trialkylammonium;

X is O, S, Se, —CR$^3$R$^4$, or —NR$^5$, wherein

R$^3$ and R$^4$ are independently $C_1$-$C_2$ alkyl or $C_7$-$C_{22}$ arylalkyl, each alkyl portion of which optionally incorporates up to six hetero atoms, selected from N, O and S, and each alkyl portion of which is optionally substituted one or more times with F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium; or R$^3$ and R$^4$ taken in combination complete a five- or six-membered saturated or unsaturated ring that is optionally substituted with F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium; and R$^5$ is H or $C_1$-$C_{22}$ alkyl that is optionally substituted one or more times with hydroxy, carboxy, sulfo, amino, $C_1$-$C_6$ alkylamino or $C_2$-$C_{12}$ dialkylamino;

Z is O, S, Se, —CR$^{13}$R$^{14}$, or —NR$^{15}$, wherein

R$^3$ and R$^{14}$ are independently $C_1$-$C_{22}$ alkyl or $C_7$-$C_{22}$ arylalkyl, each alkyl portion of which optionally incorporates up to six hetero atoms, selected from N, O and S, and each alkyl portion of which is optionally substituted one or more times with F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium; or R$^1$ and R$^{14}$ taken in combination complete a five- or six-membered saturated or unsaturated ring that is optionally substituted with F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium; and R$^{15}$ is H or $C_1$-$C_{22}$ alkyl that is optionally substituted one or more times with hydroxy, carboxy, sulfo, amino, $C_1$-$C_6$ alkylamino or $C_2$-$C_{12}$ dialkylamino;

each of R$^{21}$, R$^{22}$, R$^{23}$ is independently H, F, Cl, $C_1$-$C_6$ alkyl, $C_1$-$C_6$ alkoxy, aryl, aryloxy, a nitrogen heterocycle, an iminium ion; or any two adjacent substituents of R$^{21}$, R$^{22}$, R$^{23}$, when taken in combination, forms an aryl group or a 4-, 5-, or 6-membered saturated or unsaturated hydrocarbon ring that is optionally substituted one or more times with $C_1$-$C_6$ alkyl, halogen, or a carbonyl oxygen; or R$^{21}$ taken in combination with one of R$^3$ and R$^4$ forms a six-membered ring that is optionally substituted with $C_1$-$C_6$ alkyl; or R$^{23}$ adjacent to Z, taken in combination with one of R$^{13}$ and R$^{14}$ forms a six-membered ring that is optionally substituted by a $C_1$-$C_6$ alkyl;

R$^{24}$ is H or D in either R or S configuration;

n is 0, 1, 2, or 3;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —NR$^{15'}$—, —NR$^{15'}$C(O)—, —C(O)NR$^{15'}$—, —NZ—, —NZC(O)—, and —C(O)NZ—;

each Z is an independently selected $C_1$-$C_{10}$ alkyl that is additionally substituted with one member from the group of R$^{3'}$ and R$^{16'}$;

each R$^{13'}$ is a member independently selected from the group of hydroxyl, amino, carboxyl, alkoxycarbonyl, amido, sulfonato, and thioacetyl;

R$^{15'}$ is a member selected from the group of alkyl and alkoxycarbonylalkyl; wherein the alkyl is optionally interrupted by at least one heteroatom; and each R$^{16'}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, R$^{16'}$ is activated acyl, maleimidyl, phosphoramidityl, or glycidyl.

In a preferred aspect, L is not present. Alternatively, L is a $C_1$-$C_{10}$ alkylene interrupted by ether linkages (e.g., a polyethylene glycol oligomer).

In a preferred aspect, Y is a bond. Alternatively, Y is —O—. Alternatively, Y is an amido group optionally substituted with R$^{15'}$ at the amido nitrogen.

In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is a bond; Z is (CH$_2$)$_t$R$^{13'}$; R$^{13'}$ is carboxyl or activated acyl; and t is an integer from 1 to 10 such as 1, 2, 3, 4, 5, 6, 7, 8, 9, or 10. Alternatively, t is an integer from 0 to 10.

In still another alternative preferred aspect, the Z group's L group is a bond. Alternatively, Z is R$^{13'}$ or R$^{16'}$ that is directly bonded to the phenyl ring itself if L and Y are also bonds.

In yet still another alternative preferred aspect, -L-Y—Z has at least four carbons. Alternatively, Z has at least four carbons.

In a preferred embodiment, R$^{13'}$ is carboxyl, amido, or alkoxycarbonyl. In a more preferred embodiment, R$^{13'}$ is carboxyl. Alternatively, R$^{13'}$ is sulfonato.

In a preferred aspect, $R^{15'}$ is alkyl. In a more preferred aspect, $R^{15'}$ is lower alkyl. Alternatively, $R^{15'}$ is interrupted by ether linkages (e.g., a polyethylene glycol oligomer).

In a preferred aspect, $R^{16'}$ is activated acyl, maleimidyl, phosphoramidityl, or glycidyl. In a more preferred embodiment, $R^{16'}$ is activated acyl. Alternatively, $R^{16'}$ is activated ester. In a still more preferred embodiment, $R^{16'}$ is succinimidyloxy-ester or sulfosuccinimidyloxy-ester.

Some embodiments of the invention provide methods where in the hydro/deteurocyanine dye is selected from the compounds in Table 1.

TABLE 1

Hydrocyanine and Deuterocyanine Dyes for ROS Imaging and Immunoassays

| Compound No. | Compound Name | Compound Structure |
|---|---|---|
| 1 | H-IR650DIOL | 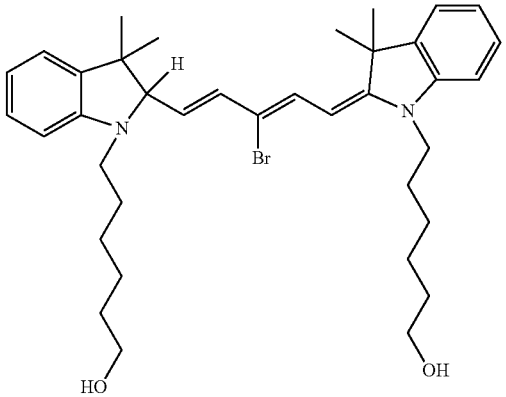 [SMILES: CC1(C)\C(=C/C=C(Br)/C=C/C2N(CCCCCCO)c3ccccc3C2(C)C)N(CCCCCCO)c2ccccc21] |
| 2 | H-IR680DIOL | 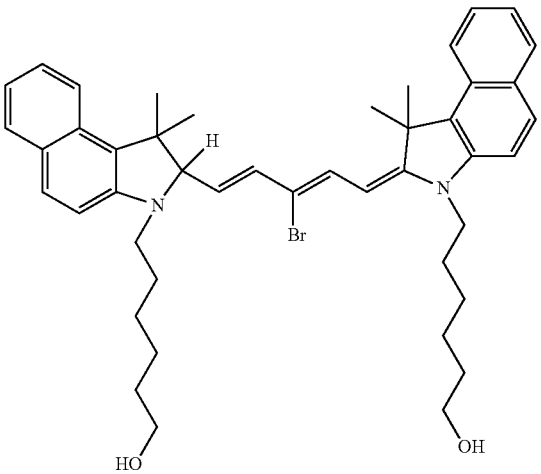 [SMILES: CC1(C)\C(=C/C=C(Br)/C=C/C2N(CCCCCCO)c3ccc4ccccc4c3C2(C)C)N(CCCCCCO)c2ccc3ccccc3c21] |
| 3 | H-IR675 | 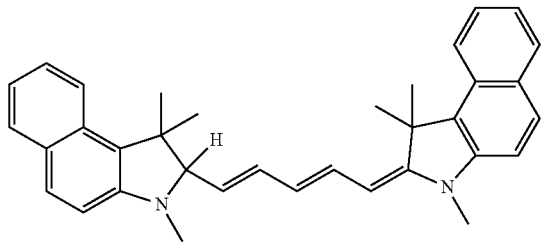 [SMILES: CN1/C(=C/C=C/C=C/C2N(C)c3ccc4ccccc4c3C2(C)C)C(C)(C)c2c1ccc1ccccc21] |

TABLE 1-continued

Hydrocyanine and Deuterocyanine Dyes for ROS Imaging and Immunoassays

| Compound No. | Compound Name | Compound Structure |
|---|---|---|
| 4 | H-IR780F2 | 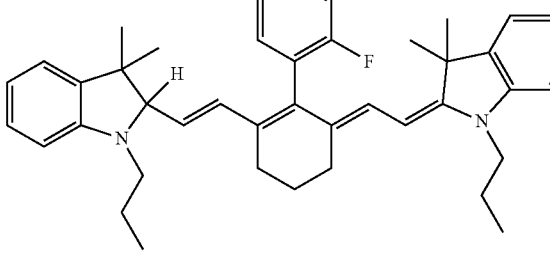 |
| 5 | H-IRDye® 800CW | 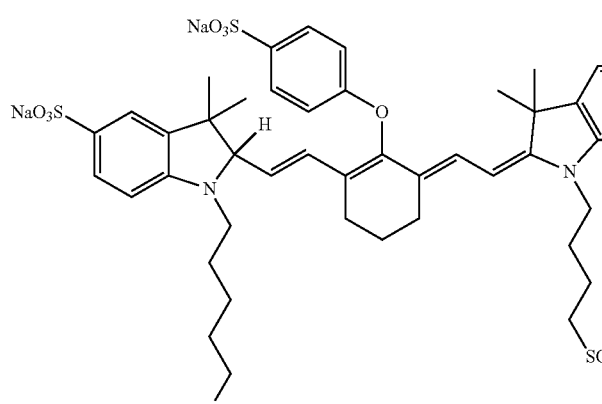 |
| 6 | H-Cy5 | 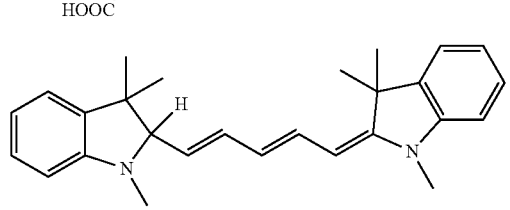 |
| 7 | H-Cy3 | 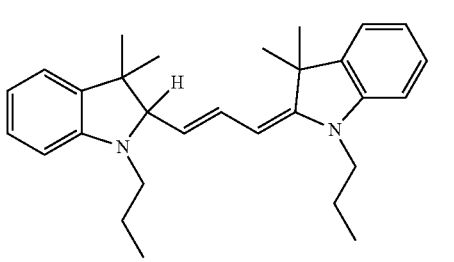 [SMILES: CCCN1/C(=C/C=C/C2N(CCC)c3ccccc3C2(C)C)C(C)(C)c2ccccc21] |

III. Methods of Making

Many of the cyanine dyes (oxidized form) used to make the compounds of Formula I-VII (reduced dye) are commercially available from LI-COR Biosciences, Lincoln Nebr. As used herein, "reduced dye" includes a dye molecule in which one or more π-bonds have been reduced, disrupting the extended π-conjugation, resulting in a molecule that exhibits negligible or no fluorescence. For example, "reduced cyanine dye," "hydrocyanine," or "deuterocyanine" include a cyanine dye wherein the iminium cation has been reduced to make a compound of the present invention. "Deuterocyanine," as used herein, includes a cyanine dye that has been reduced by a deuterated reducing agent thus incorporating deuterium into the reduced molecule.

Figure 7:
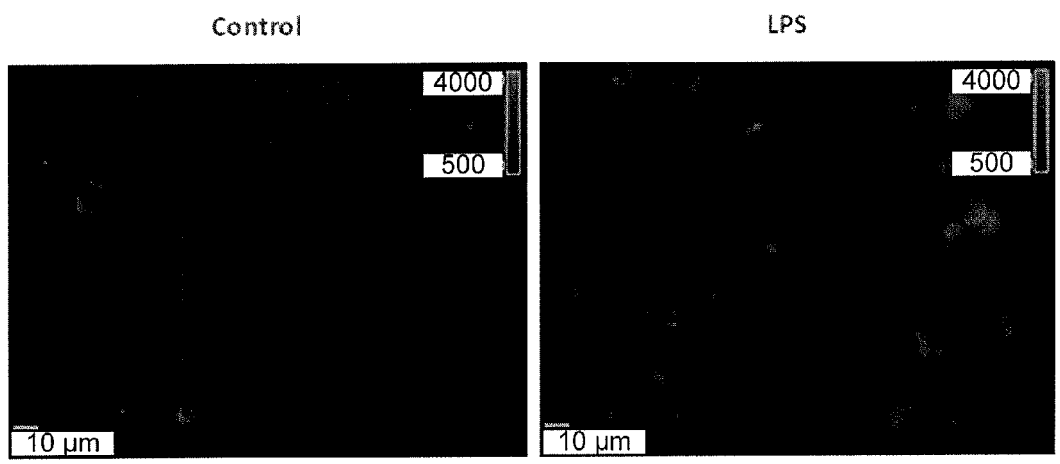
FIG. 7 shows detection of oxygen species (ROS) in untreated mouse macrophage cells (RAW 264.7; left panel) and RAW 264.7 cells treated with lipopolysaccharide endotoxin (LPS; right panel). After LPS treatment, cells were loaded with H-IR650DIOL and imaged via fluorescence microscopy.

For example, with reference to FIG. 7, to a solution of IRDye® 800CW carboxylate, commercially available from LI-COR Biosciences, sodium borohydride was added. The reaction mixture was stirred at room temperature for 15 minutes. After chromatography, the reduced dye was isolated.

Certain of the compounds of Formula I in their oxidized form are disclosed in WO 2012/054784, the teachings of which are hereby incorporated by reference in its entirety for all purposes. In one aspect, the oxidized form of the cyanine compounds scan be prepared using a procedure for a Schiff base such as the one included in U.S. Pat. No. 6,747,159 (Ar=Ph; pyridine/Ac$_2$O, Δ). The substituent can optionally be modified after the synthesis of the polymethine bridge (e.g., deprotected, activated for reaction with a biomolecule, or reacted to form a linking group).

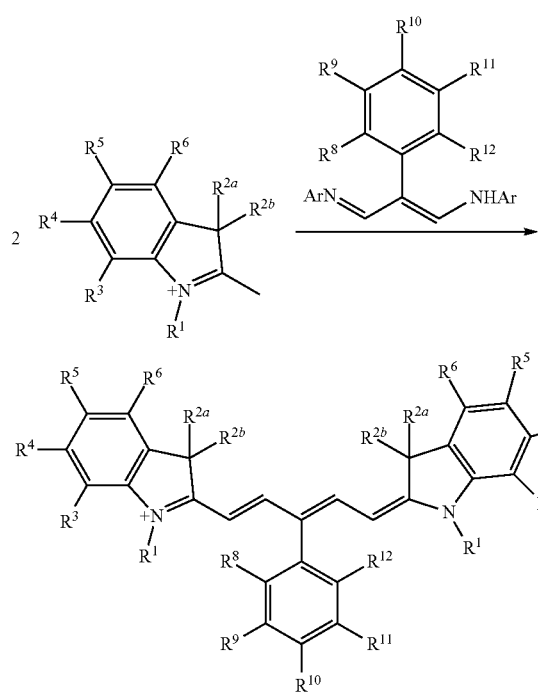
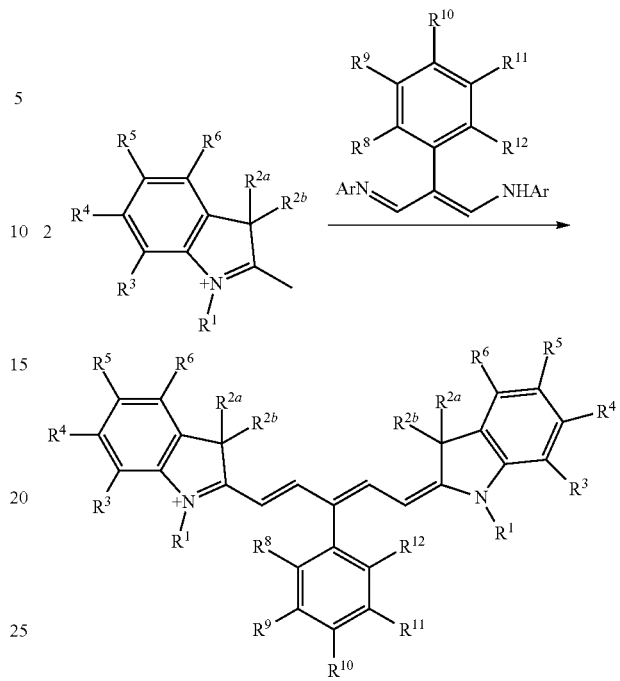

In another aspect, the oxidized cyanine compounds of Formula I are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group). Subsequent reduction yields the compounds of Formula I.

Certain of the compounds of Formula II in their oxidized form are disclosed in U.S. Pat. No. 6,995,274, the teachings of which are hereby incorporated by reference in its entirety for all purposes. In general, substituted or unsubstituted indolesulfonate quaternary salts are reacted with a commercially available Schiffs base such as N-[(3-(anilinomethylene)-2-chloro-1-cyclohexen-1-yl) methylene]aniline monohydrochloride using techniques and reaction conditions that are well known in the art. The product is then reacted with a hydroxybenzene sulfonic acid to give an oxidized dye. Subsequent reduction yields a compound of Formula II.

With respect to the compounds of Formula III, the oxidized form of the cyanine dyes are disclosed in WO 2010/121163, the disclosure of which is hereby incorporated by reference in its entirety for all purposes. In brief, the oxidized compounds of Formula I are prepared by reaction with a dialdehyde or dialdehyde equivalent (e.g., a Schiff base) that already incorporates the substituent for the polymethine bridge. A representative procedure for a dialdehyde is included in pending U.S. patent application Ser. No. 12/065,391 (US 2008/0267883 A1). A representative procedure for a Schiff base is included in U.S. Pat. No. 6,747,159 (Ar=Ph; pyridine/Ac$_2$O, Δ). The substituent can optionally be modified after the synthesis of the polymethine bridge (e.g., deprotected, activated for reaction with a biomolecule, or reacted to form a linking group).

In another aspect, the oxidized cyanine compounds of Formula III are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group). Subsequent reduction yields the compounds of Formula III.

With respect to the compounds of Formula IV, the oxidized form of the cyanine dyes are disclosed in WO 2012/054749, the disclosure of which is hereby incorporated by reference in its entirety for all purposes. In brief, the cyanine compounds set forth in Formula II are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group). In certain instances, the polymethine substrate for the Suzuki coupling is a 3-halopentamethine. In a preferred embodiment, the halo-substituent is a chloride or a bromide.

Certain of the compounds of Formula V are prepared using a procedure as set forth in Example 13.

Hydrocyanine and deuterocyanine dyes of Formula VI are as described in U.S. Patent Application Publication No. 2011/0070166, incorporated herein by reference in its entirety. Hydrocyanine and deuterocyanine dyes of Formula VII are as described in WO 2012/061403, incorporated herein by reference in its entirety.

IV. Methods of Labeling Biomolecules or Conjugates

The compounds of Formula I-VII can be attached to biomolecules or other dyes.

Methods of linking dyes to various types of biomolecules are well-known in the art. For a thorough review of, e.g., oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

"Click" chemistry provides one possible way for linking the inventive dyes to biomolecules. Click chemistry uses simple, robust reactions, such as the copper-catalyzed cycloaddition of azides and alkynes, to create intermolecular linkages. For a review of click chemistry, see Kolb, H. C.; Finn, M. G.; Sharpless, K. B. Angew. Chem. 2001, 40, 2004.

Connection (or ligation) of two fragments to make a larger molecule or structure is often achieved with the help of so-called "click chemistry" described by Sharpless et al. Angew. Chem. Int. Ed. 40: 2004 (2001). This term is used to describe a set of bimolecular reactions between two different reactants such as azides and acetylenes. The formation of 1,2,3-triazoles in 1,3-dipolar cycloaddition of azides to a triple bond is known, but because the activation energy of acetylene-azide cycloaddition is relatively high, the reaction is slow under ambient conditions.

The utility of the reaction of azides with alkynes was expanded by the discovery of Cu (I) catalysis. 1,3-cycloaddition of azides to terminal acetylenes in the presence of catalytic amounts of cuprous salts is facile at room temperature in organic or aqueous solutions.

U.S. Pat. No. 7,807,619 to Bertozzi et al. teaches modified cycloalkyne compounds and method of use of such compounds in modifying biomolecules. Bertozzi et al. teach a cycloaddition reaction that can be carried out under physiological conditions. As disclosed therein, a modified cycloalkyne is reacted with an azide moiety on a target biomolecule, generating a covalently modified biomolecule.

The present invention provides reduced cyanine dyes with click chemistry functionalities useful for labeling biomolecules. As such, in one aspect, the present invention provides compounds of Formula I-VII, in which in one embodiment, each $R^{16}$ is independently a member selected from the group consisting of activated acyl, acrylamido, optionally substituted alkylsulfonate ester, azido, optionally substituted arylsulfonate ester, amino, azido, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido group, and a pegylated alkynyl group; and in which at least one $R^{16}$ is independently a member selected from the group azido, alkynyl, a pegylated azido and a pegylated alkynyl.

In yet other aspects, the present invention relates to two components that interact with each other to form a stable covalent bio-orthogonal bond. Bio-orthogonal reactions are reactions of materials with each other, wherein each material has limited or essentially no reactivity with functional groups found in vivo. These components are of use in chemical and biological assays, as chemical reagents, medical imaging and therapy, and more particularly, in nucleic acid modification techniques. According to a particular embodiment of the invention, the covalent bio-orthogonal bond is obtained by the [3+2]cycloaddition of azides and alkynes.

In still other aspects, one of the two components that interact with each other to form a stable covalent bio-orthogonal bond is a near infrared dye, such as a reduced cyanine dye. In a preferred aspect, the reduced cyanine dyes of the present invention comprise either an azide or an alkyne group for use as a reactant in a click chemistry reaction and the other reactant is a biomolecule such as a nucleotide comprising either an alkyne or azide group.

Azide reactive groups such as an alkyne compounds can react with at least one 1,3-dipole-functional compound such as an alkyne reactive group (e.g., a azido group) in a cyclization reaction to form a heterocyclic compound. In certain embodiments, the reaction can be carried out in the presence of an added catalyst (e.g., Cu(I)). In other embodiments, the reaction is carried out in the absence of such catalysts. Exemplary 1,3-dipole-functional compounds include, but are not limited to, azide-functional compounds, nitrile oxide-functional compounds, nitrone-functional compounds, azoxy-functional compounds, and/or acyl diazofunctional compounds. Preferably, azide-functional compounds are used.

Suitable biomolecule moieties for click reaction include, for example, monomeric and polymeric derivatives of nucleotides, carbohydrates, amino acids, lipids, glycols, alkanes, alkenes, arene, silicates, as well as biologically active and inactive compounds obtained from nature or from artificial synthesis.

Other suitable biological molecules include those having a azido or alkynyl functionality, which include, but are not limited to, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like. These biological molecules will in turn be reacted with the dye compounds of the present invention comprising either an azide or an alkyne group for use in click chemistry reactions.

In one aspect, the reduced cyanine compounds of Formula I-VII have sufficient solubility in aqueous solutions that once they are conjugated to a soluble ligand or biomolecule, the ligand or biomolecule retains its solubility. In certain instances, the bioconjugates also have good solubility in organic media (e.g., DMSO or DMF), which provides considerable versatility in synthetic approaches to the labeling of desired materials.

In another aspect, the present invention provides a method or process for labeling a ligand or biomolecule with a compound of Formula I-VII, the method comprising: contacting a ligand or biomolecule with a compound having Formula I-VII to generate the corresponding bioconjugate.

In one preferred embodiment, the $R^{16}$ group or the $R^{13}$ group reacts with a thiol, a hydroxyl, a carboxyl, or an amino group on a biomolecule, forming a linking group between the dye and the biomolecule. In a more preferred embodiment, this reaction is carried out in mixtures of aqueous buffer and an organic solvent such as DMF at pH 8 to 9. Alternatively, this reaction is carried out in distilled water or in an aqueous buffer solution. For thiols or for acidic groups, a pH of 7 or lower is preferred for the reaction solvent, especially if a substrate also contains a reactive amino group.

Selected examples of reactive functionalities useful for attaching a compound of Formula I-VII to a ligand or biomolecule are shown in Table 2, wherein the bond results from the reaction of a dye with a ligand or biomolecule. Column A of Table 2 is a list of the reactive functionalities, which can be on the compound of Formula I-VII or the biomolecule. Column B is a list of the complementary reactive groups (preferably, a carboxyl, hydroxyl, thiol, or amino functionality), which can be on the biomolecule or the compound of Formula I-VII, and which react with the indicated functionality of Column A to form the bond of Column C. Those of skill in the art will know of other bonds suitable for use in the present invention.

TABLE 2

Exemplary Bonds for Linking Groups

| A<br>Reactive Functionality<br>(Compound of Formula<br>I-VII or Biomolecule) | B<br>Complementary<br>Group<br>(Biomolecule or<br>Compound of<br>Formula I-VII) | C<br>Resulting Linking Group |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | amides/imides |
| aryl halides | thiols | thiophenols |
| aryl halides | amines | aryl amines |
| azides | alkynes | 1,2,3-triazoles |
| azides | ester with phosphine reagent (e.g., o-diphenyl-phosphino group) | amide (and phosphine oxide) |
| aziridines | thiols | thioethers |
| boronates | glycols | boronate esters |
| boronates/boronic acids | aryl halides | C—C bond to aryl ring |
| boronates/boronic acids | alkenyl halides | C—C bond to alkenyl group |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| electron-rich diene | dienophile (e.g., electron-poor alkene) | cyclohexene (Diels-Alder cycloaddition) |
| epoxides | thiols | thioethers |
| epoxides | amines | alkyl amines |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| photoactivatable group | varies; see definition | varies; see definition |
| quadricyclanes | π-electrophile (e.g., Ni bis(dithiolene)) | norbornene cycloaddition product |
| silyl halides | alcohols | silyl ethers |
| sulfonyl azides | thiocarboxylic acids | N-acyl sulfonamides |
| sulfonate esters | amines/anilines | alkyl amines |
| sulfonate esters | carboxylic acids | esters |
| sulfonate esters | thiols | thioethers |
| sulfonate esters | alcohols/phenols | ethers |
| sulfonyl halides | amines/anilines | sulfonamides |
| 1,2,4,5-tetrazine | alkene | dihydropyradazine |

TABLE 2-continued

Exemplary Bonds for Linking Groups

| A<br>Reactive Functionality<br>(Compound of Formula<br>I-VII or Biomolecule) | B<br>Complementary<br>Group<br>(Biomolecule or<br>Compound of<br>Formula I-VII) | C<br>Resulting Linking Group |
|---|---|---|
| vinyl sulfonyl | thiols | thioethers |
| vinyl sulfonyl | activated diene | cyclohexenyl (Diels-Alder) |

*Activated esters, as understood in the art, generally have the formula —C(O)OM, where —OM is a leaving group (e.g. succinimidyloxy (—OC$_4$H$_4$NO$_2$), sulfosuccinimidyloxy (—OC$_4$H$_3$NO$_2$SO$_3$H), -1-oxybenzotriazolyl (-OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)R$^a$ or —C(O)OC(NR$^a$)NHR$^b$, wherein R$^a$ and R$^b$ are members independently selected from the group consisting of C$_1$-C$_6$ alkyl, C$_1$-C$_6$ perfluoroalkyl, C$_1$-C$_6$ alkoxy, cyclohexyl, 3-dimethylaminopropyl, or N-morpholinoethyl).
**Acyl azides can also rearrange to isocyanates.

Some methods of forming linking groups include those taught in Sletten and Bertozzi, *J. Am. Chem. Soc.* electronic publication at dx.doi.org/10.1021/ja2072934; Devaraj and Weissleder, *Acc. Chem. Res.* electronic publication at dx.doi.org/10.1021/ar200037t; Krishnamoorthy and Begley, *J. Am. Chem. Soc.* electronic publication at dx.doi.org/10.1021/ja1034107; and the like.

When linking a compound of Formula I-VII having a carboxylic acid with an amine-containing ligand or biomolecule, the carboxylic acid can first be converted to a more reactive form, e.g, a N-hydroxy succinimide (NHS) ester or a mixed anhydride, by means of an activating reagent. The amine-containing ligand or biomolecule is treated with the resulting activated acyl to form an amide linkage. In a more preferred embodiment, this reaction is carried out in aqueous buffer at pH 8 to 9 with DMSO or DMF as an optional co-solvent. Alternatively, this reaction is carried out in distilled water or in an aqueous buffer solution.

Similarly, the attachment of an isocyanate- or isothiocyanate-containing compound of Formula I-VII is analogous to the procedure for the carboxy dye, but no activation step is required. The amine-containing ligand or biomolecule is treated directly with the activated acyl compound to form a urea or a thiourea linkage. In a more preferred embodiment, the reaction is carried out in aqueous buffer at pH 9 to 10 with DMSO or DMF as an optional co-solvent. Alternatively, this reaction is carried out in distilled water or in an aqueous buffer solution.

If the compound of Formula I-VII or biomolecule has a reactive hydroxyl group, it can be linked to a ligand or biomolecule by means of phosphoramidite chemistry, which ultimately forms a phosphate linkage between the dye and the biomolecule. For examples of such labeling methods, see U.S. Pat. No. 6,027,709, which discloses many preferred linking groups, linking methods, and biomolecules that can be readily labeled. In one embodiment, solid-phase synthesis is preferred, as disclosed in U.S. Pat. No. 6,027,709.

In a preferred embodiment, the biomolecule is DNA or RNA. Use of phosphoramidite chemistry allows labeling of a DNA or an RNA during the synthesis process. The protected nucleotide is labeled while attached to a solid-phase support. The free 5'-OH group is reacted with the phosphoramidite and a tetrazole activator to form a phosphite linkage which subsequently is oxidized to phosphate. The labeled DNA or RNA is then cleaved from the solid phase by means of ammonia or by another standard procedure.

It is generally preferred to prepare a phosphoramidite of a reduced cyanine dye to label DNA molecules in a DNA synthesizer. It is also preferred to attach the dye to the 5' end of a protected, support-bonded oligonucleotide through standard phosphoramidite chemistry. For a list of preferred label terminators for use in DNA sequencing, see U.S. Pat. No. 5,332,666.

In another preferred embodiment, the biomolecule is an antibody. It is preferred that antibody labeling is carried out in a buffer optionally including an organic co-solvent, under basic pH conditions, and at room temperature. It is also preferred that the labeled antibody be purified by dialysis or by gel permeation chromatography using equipment such as a SEPHADEX® G-50 column to remove any unconjugated compound of Formula I-VII. Those of skill in the art will know of other ways and means for purification.

In still another preferred embodiment, the biomolecule contains a thiol group that forms the linking group by reaction with a maleimidyl substituent at $R^{16}$. In a more preferred embodiment, the biomolecule is a protein, a peptide, an antibody, a thiolated nucleotide, or a thiolated deoxynucleotide.

In yet other aspects, the linking group or biomolecule comprises a polymer. In a preferred embodiment, the polymer is a member selected from the group of a PEG, a copolymer of PEG-polyurethane, and a copolymer of PEG-polypropylene. In still yet other aspects, the linking group is a member selected from the group of a polysaccharide, a polypeptide, an oligosaccharide, a polymer, a co-polymer and an oligonucleotide.

In one aspect, biomolecules can be labeled according to the present invention by means of a kit. In certain instances, the kit comprises a buffer and a dye as disclosed in the instant application (e.g., a compound of Formula I). Preferably, the kit contains a coupling buffer such as 1 M $KH_2PO_4$ (pH 5), optionally with added acid or base to modify the pH (e.g., pH 8.5 is preferred for reactions with succinimide esters and pH 7 is preferred for reactions with maleimides). Preferably, the buffer has a qualified low fluorescence background.

Optionally, the kit can contain a purification sub-kit. After labeling a biomolecule with a preferred dye, the labeled biomolecule may be separated from any side reaction products and any free hydrolyzed product resulting from normal hydrolysis. For biomolecules containing 13 or fewer amino acids, preparative thin layer chromatography (TLC) can remove impurities. In certain instances, preparative TLC, optionally performed with commercially available TLC kits, can be used to purify dye-labeled peptides or proteins.

For larger biomolecules such as larger peptides or proteins, a SEPHADEX® G-15, G-25, or G-50 resin may remove unwanted derivatives. In certain instances, a Gel Filtration of Proteins Kit, which is commercially available from Life Sciences, can be used to separate dye-labeled peptides and proteins from free dye. The labeled biomolecules that remain after desalting can often be used successfully without further purification. In some cases, it may be necessary to resolve and assess the activity of the different products by means of HPLC or other chromatographic techniques.

V. Conjugate Compounds

A. Bioconjugates

In another embodiment of the invention, bioconjugates are provided wherein a compound of Formula I, II, III, IV, V, VI, or VII is reacted with a biomolecule to generate a conjugate of Formula $I^L$, $II^L$, $III^L$, $IV^L$, $V^L$, $VI^L$ or $VII^L$, respectively.

Each Z of Formula I, II, III, IV, V, VI, or VII becomes $Z^L$ in Formula $I^L$, $II^L$, $III^L$, $IV^L$, $V^L$, $VI^L$ or $VII^L$, wherein $Z^L$ is an independently selected $C_1$-$C_{10}$ alkyl that is additionally substituted with one member from the group of $R^{13}$ or $R^L$. In a more preferred aspect, $Z^L$ is $C_1$-$C_6$ alkyl. Alternatively, $Z^L$ is interrupted by ether linkages (e.g., a polyethylene glycol oligomer). In a yet still more preferred aspect, at least one $Z^L$ is -propylene-C(O)—$R^L$ or -butylene-C(O)—$R^L$. Alternatively, exactly one $Z^L$ is -propylene-C(O)—$R^L$ or -butylene-C(O)—$R^L$.

In an alternative aspect, $Z^L$ is optional, and $R^L$ is connected directly to -L-Y— or even directly bonded to a portion of the reduced dye itself if L and Y are absent.

Each $R^L$ (e.g., $R^L$ as disclosed previously in the specification) comprises 1) a linking group that connects the reduced cyanine dye compound to a biomolecule; and 2) the biomolecule to which it is connected (i.e., the linking group and the biomolecule connected thereby). In a preferred embodiment, a bioconjugate compound comprises at least one $R^L$. Preferred linking groups are indicated in Table 2 (column C). In a particularly preferred aspect, the linking group is an amide or an ester. In a more particularly preferred aspect, the linking group is an amide.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In another preferred embodiment of the bioconjugate, any preferred embodiments or aspects of the inventive compound of Formula I-VII can included in the embodiment of a bioconjugate of Formula $I^L$, $II^L$, $III^L$, $IV^L$, $V^L$, $VI^L$ or $VII^L$.

In certain aspects, preferred biomolecules for the instant invention include an acyclo terminator triphosphate, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like.

In still other instances, suitable nucleotides include nucleoside polyphosphates, including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Nucleotides containing 3, 4, 5, 6, or more phosphate groups, in the polyphosphate chain, where the phosphate (e.g., α, β, γ, ε, or terminal phosphate), sugar, base, or combination thereof is labeled with a compound of Formula I-VII. The polyphosphate nucleotides include, but are not limited to, tetraphosphates, pentaphosphates, hexaphosphates, heptaphosphates, and the like. The bases include for example, purines, (adenine and guanine) pyrimidines, (thymine, uracil and cytosine) and derivatives thereof.

In certain instances, the dye of Formula I is attached to the phosphate (e.g. α, β, γ, ε-phosphate or terminal phosphate) through a phosphorothioate linkage (see, for example, U.S. Pat. No. 6,323,186, incorporated herein by reference), heteroatom, or functional group A, or B, resulting in linkage C of Table I. See also U.S. Pat. No. 6,399,335 (incorporated herein by reference) entitled "γ-phosphoester nucleoside triphosphates," which provides methods and compositions for polymerizing particular nucleotides with a polymerase using γ-phosphoester linked nucleoside triphosphates. Other ways of linking the compounds of Formula I to a nucleotide are known to those of skill in the art. Using these nucleotides with a DNA polymerase can lead to identification of specific nucleotides in a DNA or RNA sequence by identification of the labeled pyrophosphate or polyphosphate released upon incorporation of the nucleotide base into RNA or DNA. (See for example, U.S. Pat. No. 6,232,075, U.S. Pat. Publ. No. 2004/0241716 and U.S. Pat. No. 7,452,698 each of which is incorporated herein by reference).

More preferred aspects include an antibody, an avidin, and a streptavidin. Even more preferred aspects include a goat anti-mouse (GAM) antibody, a goat anti-rabbit (GAR) antibody, and streptavidin.

In certain other aspects, preferred biomolecules for the instant invention include somatostatin, endostatin, a carbohydrate, an oligosaccharide, an aptamer, a liposome, PEG, an angiopoietin, angiostatin, angiotensin II, $\alpha_2$-antiplasmin, annexin V, β-cyclodextrin tetradecasulfate, endoglin, endosialin, endostatin, epidermal growth factor, fibrin, fibrinopeptide β, fibroblast growth factor, FGF-3, basic fibronectin, fumagillin, heparin, hepatocycte growth factor, hyaluronan, aninsulin-like growth factor, an interferon-α, β inhibitor, IL inhibitor, laminin, leukemia inhibitory factor, linomide, a metalloproteinase, a metalloproteinase inhibitor, an antibody, an antibody fragment, an acyclic RGD peptide, a cyclic RGD peptide, placental growth factor, placental proliferin-related protein, plasminogen, plasminogen activator, plasminogen activator inhibitor-1, a platelet activating factor antagonist, platelet-derived growth factor, a platelet-derived growth factor receptor, a platelet-derived growth factor receptor, platelet-derived endothelial cell growth factor, pleiotropin, proliferin, proliferin-related protein, a selectin, SPARC, a snake venom, substance P, suramin, a tissue inhibitor of a metalloproteinase, thalidomide, thrombin, thrombin-receptor-activating tetradecapeptide, transformin growth factor-α, β, transforming growth factor receptor, tumor growth factor-α, tumor necrosis factor, vitronectin, and the like.

In still other aspects, preferred biomolecules include a carbohydrate and a carbohydrate derivative. Representative examples include glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof. Even more preferred biomolecules include 2-deoxy-D-glucose, 2-deoxy-L-glucose, and racemic 2-deoxyglucose.

In yet still other aspects, the biomolecule can be a ligand that has affinity for a receptor selected from the group of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocorticosteroid receptor, Retinoid-X receptor, RHAMM, high affinity folate receptors, Met receptor, estrogen receptor and Ki67.

Alternatively, the biomolecule is selected from the group of somatostatin, endostatin, a carbohydrate, a monosaccaride, a disaccharide, a trisaccharide, an oligosaccharide, aptamer, liposome and polyethylene glycol.

In yet another aspect, the biomolecule is a small-molecule drug or drug-like molecule such as a tetracycline antibiotic, a tetracycline derivative, and calcein. Other conjugates include pluonic nanocarriers for example, see Ja-Young Kim et al., *Journal of Controlled Release* 156 (2011) 398-405, incorporated herein by reference.

B. Ratiometric Probes

In yet another embodiment, the present invention provides ratiometric probes. In this aspect, the reduced dyes of Formula I-VII can be conjugated using the techniques of Table 2 to another dye, preferably, an always on dye. Each $R^L$ comprises 1) a linking group that connects the reduced cyanine dye compound to a dye; and 2) the dye to which it is connected (i.e., the linking group and the dye connected thereby), wherein the compound comprises at least one $R^L$. Preferred linking groups are indicated in Table 2 (column C). In a particularly preferred aspect, the linking group is an amide or an ester. In a more particularly preferred aspect, the linking group is an amide.

The ratiometric hydrocyanines are synthesized and tested in vitro by verifying that they possess sufficient cell permeability and ROS sensitivity to detect a quantitative increase of stimulated cells by excitation of for example a BODIPY dye, and a hydrocyanine-660 dye at 501 nm and 635 nm respectively. The intensity ratio of hydrocyanine-660 emission at 660 nm upon reacting with ROS, to BODIPY Dye's emission at 517 nm, 1660/1517, will show a ratiometric response toward ROS. In the cell culture studies, it is anticipated that a ratiometric response toward ROS from the Hydrocyanine-660 moiety with the BODIPY dye in stimulated groups.

Exemplary fluorophores suitable for use in the present invention as ratiometric probes include IRDye® 700DX, IRDye® 700, IRDye® 800RS, IRDye® 800CW, IRDye® 800, Cy5, Cy5.5, Cy7, DY 676, DY680, DY682, DY780, and mixtures thereof. Additional suitable fluorophores include enzyme-cofactors; lanthanide, green fluorescent protein, yellow fluorescent protein, red fluorescent protein, or mutants and derivates thereof. In one embodiment of the invention, the second member of the specific binding pair has a detectable group attached thereto. Other suitable dyes include those listed in the Molecular Probes Catalogue, which is herein incorporated by reference (see R. Haugland, *The Handbook—A Guide to Fluorescent Probes and Labeling Technologies*, 10$^{th}$ Edition, Molecular probes, Inc. (2005)). Such exemplary fluorophores include, but are not limited to, Alexa Fluor® dyes such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790, as well as other fluorophores such as, for example, Dansyl Chloride (DNS-Cl), 5-(iodoacetamida)fluoroscein (5-IAF), fluoroscein 5-isothiocyanate (FITC), tetramethylrhodamine 5- (and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids (e.g., 1-anilinonaphthalene-8-sulfonic acid (ANS), 6-(p-toluidinyl)naphthalen-e-2-sulfonic acid (TNS), and the like), Anthroyl fatty acid, DPH, Parinaric acid, TMA-DPH, Fluorenyl fatty acid, fluorescein-phosphatidylethanolamine, Texas Red-phosphatidylethanolamine, Pyrenyl-phophatidylcholine, Fluorenyl-phosphotidylcholine, Merocyanine 540, 1-(3-sulfonatopropyl)-4-[β-[2[(di-n-butylamino)-6 naphthyl]vinyl]pyridinium betaine (Naphthyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, Typically, the fluorescent group is a fluorophore selected from the category of dyes comprising polymethines, pthalocyanines, cyanines, xanthenes, fluorenes, rhodamines, coumarins, fluoresceins and BODIPY™.

Given the importance of ROS in physiology and pathology, the ratiometric probes herein are useful for quantitative determination of ROS in cells, tissue and in vivo biomedical research. The ratiometric indicators disclosed herein have significant advantages over single-emission probes. Measurements of ROS concentrations using fluorescence microscopy are sensitive to the effects of uneven dye loading, photobleaching, leakage of dye, and unequal cell thickness. The inventive ratiometric probes afford simultaneous recording of two measurable signals in the presence and absence of an analyte allow for accurate and quantitative readouts.

VI. Methods of Imaging

In another embodiment, the compounds of Formula I-VII or their bioconjugates can be used as in vitro or in vivo optical imaging agents of tissues and organs in various biomedical applications. In one embodiment, the present invention provides a method for imaging, the method comprising administering a compound of Formula I-VII.

In certain preferred aspects of the invention, any of the embodiments or aspects of the inventive compound of Formula I-VII that are described herein can be used in the method of imaging. Representative examples of preferred compounds for use in the method are described in the specification and the dependent claims of the instant application.

In another embodiment, the present invention provides a method for imaging, the method comprising administering a compound described herein.

In certain preferred aspects of the invention, any of the embodiments or aspects of the inventive compound of Formula I-VII that are described herein can be used in the method of imaging. Representative examples of preferred compounds for use in the method are described in the specification and the dependent claims of the instant application.

In certain preferred aspects, the compounds of the present invention are used as in vivo imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. In one aspect, the compounds of the invention are useful for the detection of the presence of tumors and other abnormalities by monitoring the blood clearance profile of the dyes. In another aspect of the invention, the compounds are useful for laser assisted guided surgery for the detection of micro-metastases of tumors upon laparoscopy. In yet another aspect, the compounds are useful in the diagnosis of atherosclerotic plaques and blood clots.

In further aspects, the compounds of the present invention are used in the imaging of: (1) ocular diseases in ophthalmology, for example, to enhance visualization of chorioretinal diseases, such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; (5) breast tumors via 2D- or 3D-image reconstruction; and (6) brain tumors, perfusion, and stroke via 2D- or 3D-image reconstruction.

In certain aspects, the compounds of the invention that are bioconjugates are particularly useful for imaging tumors, tissues, and organs in a subject. For example, the existence of cancer cells or cancer tissues can be verified by labeling an anti-tumor antibody with a compound of Formula I-VII and then administering the bioconjugated antibody to the subject for detection and imaging of the tumor. Conjugates between the dye compound and other antibodies, peptides, polypeptides, proteins, ligands for cell surface receptors, small molecules, and the like are also useful agents for the in vivo imaging of tumors, tissues, and organs in a subject.

In certain aspects, the compounds of the invention may be administered either systemically or locally to the organ or tissue to be imaged, prior to the imaging procedure. In one aspect, the compounds are administered intravenously. In another aspect, the compounds are administered parenterally. In yet another aspect, the compounds are administered enterally. The compositions used for administration of the compound typically contain an effective amount of the compound or conjugate along with conventional pharmaceutical carriers and excipients appropriate for the type of administration contemplated. For example, parenteral formulations advantageously contain a sterile aqueous solution or suspension of a compound of Formula I-VII or a bioconjugate thereof. Compositions for enteral administration typically contain an effective amount of the compound or bioconjugate in aqueous solution or suspension that may optionally include buffers, surfactants, thixotropic agents, flavoring agents, and the like.

In certain aspects, the compositions are administered in doses effective to achieve the desired optical image of a tumor, tissue, or organ. Such doses may vary widely, depending upon the particular compound or bioconjugate employed, the tumor, tissue, or organ subjected to the imaging procedure, the imaging equipment being used, and the like.

In an alternative aspect, the method of the present invention provides for administering to the subject a therapeutically effective amount of a compound; a targeting agent, such as a bioconjugate; or mixtures thereof. In one aspect, the targeting agent selectively binds to the target tissue. Light at a wavelength or waveband corresponding to that which is absorbed by the photosensitizing agent is then administered. In another aspect, the compounds of the present invention act agents capable of binding to one or more types of target cells or tissues, when exposed to light of an appropriate waveband, absorb the light, causing substances to be produced that illuminate, impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

In yet another aspect, the compounds of the present invention are administered by any means known in the art, including, but not limited to, ingestion, injection, transcutaneous administration, transdermal administration, intravenously, subcutaneously and the like. Preferably, the compounds are administered transcutaneously, intravenously, subcutaneously, or intramuscularly to a subject.

In certain aspects, during imaging, the light passes through unbroken tissue. Where the tissue layer is skin or dermis, such transcutaneous imaging includes transdermal imaging, and it will be understood that the light source is external to the outer skin layer. In some aspects (i.e., transillumination), the light passes through a tissue layer, such as the outer surface layer of an organ (e.g., the liver). In such cases, the light source is preferably external to the organ, but internal or implanted within the subject or patient.

In further aspects of the invention, the target tumor, tissue, or organ for treatment is selected from the group of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, neuronal tissue or diseased neuronal tissue, and diseased cells in which the disease is one of an autoimmune and an inflammatory disease. In yet a further aspect, the target tissue is a lesion in the vascular system of a type selected from the group of atherosclerotic lesions, arteriovenous malformations, aneurysms, and venous lesions.

In certain embodiments, the compounds of Formula I-VII can be used in the detection of reactive oxygen species. In certain instances, the methods herein can be used to diagnose a disease or disorder such as carotid artery injuries, atherosclerosis, hypertension, cancers, diseases and disorders characterized by inflammation, radiation-induced late normal tissue damage; tissue damages due to chemotherapy, reperfusion after ischemia, or transplantation; diabetes, such as type 1 diabetes (TID), neurodegenerative diseases, such as Alzheimer's disease, Parkinson's disease, ALA, and Huntington's disease; cerebrovascular disease, cystic fibrosis, chronic kidney disease, cardiovascular disease, preeclampsia, diseases of the eye, and combinations thereof.

In one embodiment, the present invention provides a method for detecting a reactive oxygen species, the method comprising: contacting a cell with one or more compounds of Formula I-VII to form an oxidized form of the compound; and exciting the oxidized form of the compound to emit light.

In still further aspects, the forms of energy include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Compounds of the instant invention typically have one or more absorption wavebands that excite them to produce the substances which illuminate, damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins. More preferably, the radiation wavelength or waveband is within the NIR range of about 600 nm to about 1000 nm or a related range thereof (e.g., the ranges that are described in the instant claims).

In certain aspects, the compounds of the present invention are used to directly stain or label a sample so that the sample can be identified or quantitated. For instance, such compounds can be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable optical response as used herein includes a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some compounds of the invention may exhibit little fluorescence emission, but are still useful as quenchers or chromophoric dyes. Such chromophores are useful as energy acceptors in FRET applications, or to simply impart the desired color to a sample or portion of a sample.

FRET is a process by which a donor molecule (e.g., a dye) absorbs light, entering an excited state. Rather than emitting light, the first molecule transfers its excited state to a acceptor molecule with other properties (e.g., a dye fluorescing at a different wavelength or a quencher), and the acceptor fluoresces or quenches the excitation. Because the efficiency of the transfer is dependant on the two molecules' proximity, it can indicate information about molecular complex formation or biomolecular structure. It can also indicate where a particular complex is located within a cell or organism (e.g., FRET optical microscopy). For ways to use similar dyes as acceptors (quenchers) in FRET processes, see X. Peng, H. Chen, D. R. Draney, W. Volcheck, A. Schultz-Geschwender, and D. M. Olive, "A nonfluorescent, broad-range quencher dye for Förster resonance energy transfer assays," *Anal. Biochem* 2009, 388(2): 220-228.

In certain aspects, for biological applications, the compounds of the invention are typically used in an aqueous, mostly aqueous, or aqueous-miscible solution prepared according to methods generally known in the art. The exact concentration of compound is dependent upon the experimental conditions and the desired results, but ranges of 0.00001 mM up to 0.1 mM, such as about 0.001 mM to about 0.01 mM, are possible. The optimal concentration is determined by systematic variation until satisfactory results with minimal background fluorescence is accomplished.

In certain aspects, the method may involve treatment of an animal or sample with a dose comprising a compound of Formula I-VII, or a bioconjugate thereof, or any of the aspects or embodiments thereof. The exact concentration of compound is dependent upon the subject and the desired results. In certain embodiments, a dose of at least about 0.001, 0.005, 0.01, 0.025, 0.05, or 0.075 mg/kg is used. Alternatively, a dose of at most about 0.001, 0.005, 0.01, 0.025, 0.05, or 0.075 mg/kg is used. In certain other embodiments, a dose of at least about 0.1, 0.25, 0.5, or 0.75 mg/kg is used. Alternatively, a dose of at most about 0.1, 0.25, 0.5, or 0.75 mg/kg is used. In still other embodiments, a dose of at least about 0.1, 0.25, 0.5, or 0.75 mg/kg is used. Alternatively, a dose of at most about 0.1, 0.25, 0.5, or 0.75 mg/kg is used. In yet still other embodiments, a dose of at least about 1, 2.5, 5, or 7.5 mg/kg is used. Alternatively, a dose of at most about 1, 2.5, 5, or 7.5 mg/kg is used. In additional other embodiments, a dose of at least about 10, 25, 50, or 75 mg/kg is used. Alternatively, a dose of at most about 10, 25, 50, or 75 mg/kg is used. In additional still other embodiments, a dose of at least about 100, 250, 500, or 750 mg/kg is used. Alternatively, a dose of at most about 100, 250, 500, or 750 mg/kg is used. Other amounts for administration of an effective dose may be readily determined by one of skill in the art.

In certain aspects, in vitro, the compounds are advantageously used to stain samples with biological components. The sample can comprise heterogeneous mixtures of components (e.g., mixtures including intact cells, fixed cells, cell extracts, bacteria, viruses, organelles, and combinations thereof), or a single component or homogeneous group of components (e.g. natural or synthetic amino acid, nucleic acid or carbohydrate polymers, or lipid membrane complexes). Within the concentrations of use, these compounds are generally non-toxic to living cells and other biological components.

The compound is combined with the sample in any way that facilitates contact between the compound and the sample components of interest. Typically, the compound or a solution containing the compound is simply added to the sample. Certain compounds of the invention, particularly those that are substituted by one or more sulfonic acid moieties, tend to be impermeant to membranes of biological cells, and once inside viable cells, they are typically well-retained. Treatments that permeabilize the plasma membrane, such as electroporation, shock treatments or high extracellular ATP, can be used to introduce selected compounds into cells. Alternatively, selected dye compounds can be physically inserted into cells, e.g., by pressure microinjection, scrape loading, patch clamp methods, or phagocytosis.

Alternatively, dye compounds can be conjugated to a biomolecule that increases their uptake into cells (e.g., cell-penetrating peptides such as Tat, penetratin, transportin, derivatives thereof (e.g., Tat derivatives incorporating β- and γ-amino acids), and the like). This general approach is usable in vitro or in vivo.

In certain aspects, at any time after or during staining, the sample is illuminated with a wavelength of light selected to give a detectable optical response, and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred aspects of the invention are compounds that are excitable at or near the wavelengths 633-636 nm, 647 nm, 649 nm, 651 nm, 647-651 nm, 660 nm, 674 nm, 675 nm, 678 nm, 680 nm, 674-680 nm, 685 nm, 674-685 nm, 680-685 nm, 685-690 nm, 690-695 nm, 690-700 nm, and beyond 700 nm, such as 780 nm, 810 nm and 850 nm, as these regions closely match the output of exemplary compounds or of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined by means of a flow cytometer, examination of the sample optionally includes sorting portions of the sample according to their fluorescence response.

VII. Immunoassay Methods

In certain embodiments, the present invention concerns immunodetection methods for binding, purifying, removing, quantifying and/or otherwise generally detecting biological antigens. Commonly employed immunodetection methods include enzyme linked immunosorbent assay (ELISA), Western blotting, radioimmunoassay (RIA), immunoradiometric assay, fluoroimmunoassay, chemiluminescent assay, and bioluminescent assay. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

Chemiluminescence based detection has been the method of choice for the immunodetection methods such as Western blotting and ELISA, but the sensitivity of the analysis is compromised as the accumulation of signal intensity is not possible in chemiluminescence. The present invention provides novel near infrared (near-IR) chemifluorescent substrates that generate fluorescence signals upon activation by enzyme-antibody conjugates. The signal accumulates with each turnover by the enzyme and leads to advantageously high assay sensitivity.

Hydro/deuterocyanines are hydrophobic molecules and will stick to a blotting membrane (e.g., a nitrocellulose membrane), but they are non-fluorescent and will not emit light. Secondary antibody-HRP conjugates bound to protein bands on the membrane oxidize the hydrocyanine or deuterocyanines to their parent fluorescent cyanine dye structure, however, and consequently the bands will emit fluorescent signals. See FIG. 14. Because of the transient nature of the hydroxyl radical formed by the reaction of hydrogen peroxide and the antibody HRP conjugates, the radicals oxidize only the hydro/deuterocyanines present in the close proximity to the protein bands on the membrane and, therefore, the fluorescence signals are compact. Furthermore, the oxidized fluorescent molecules accumulate with each turn over by the HRP enzyme. The oxidized molecule is also hydrophobic and therefore, sticks to the hydrophobic membrane and hence, the sensitivity is better than chemiluminescence or secondary antibody detection methods.

The group of antigens which can be used for carrying out immunological assays is extensive and includes human biopsy material, mammalian tissue or cells, bodily fluids, mycoplasma, metazoan parasites, fungi, bacterial, protozoa, viruses, or preparations derived from any of these. Apart from the antigens described in the Examples, the following are also suitable: viruses (or antigens prepared from viruses) such as influenza strains, including A, $A_1$, $A_2$, B, C, parainfluenza strains, including 1, 2 or 3, lymphocytic choriomeningitis virus, mumps, Q fever rickettsia, rabies, respiratory syncytial virus, Rotavirus, Rubella, Adenovirus, Epstein-Barr virus, Brucella, Hepatitis B, Cocksackie B1-B6, A9, Polio 1, 2 or 3, Reo, Echo 1-33; fungal antigens, such as *Histoplasmosa capsulatumn, Coccidioides immitis, Blastomyces dermatitidis, Aspergillus fumigatus, Aspergillus flavus* and *Aspergillus carneus*; parasitic antigens, such as *Entemeba histolytica, Trypanosoma cruzi, Echinococcus granulosis, Schistosoma mansoni*; bacterial antigens, such as *Spirochete reiter, Treponema pallidum, Escherichia coli, Leptospira, Listeria, Salmonella, Shigella, Staphylococci, Streptococci,* and *Legionella pneumophila*; auto-antigens, such as nuclear ribonucleic protein, complement fractions, human serum proteins, rheumatoid factor, insulin, insulin receptor, thyroid stimulating hormone receptor, acetylcholine receptor and other hormones, receptors or allergens.

The present invention can also be used in the detection and monitoring of antigens of other kinds, such as drugs and hormones. Such tests apply specific antibodies to a support, and detect and quantitate specific antigens by the inverse of the immunoassay procedures described above. The property of complement proteins to bind specifically to antigen-antibody complexes may then be used directly or indirectly to visualize and quantitate the specific antigens, such as drugs or other pharmacological reagents, or hormones, or any desired combination of such antigens.

Immunoassay formats useful in the present invention include Western blots, enzyme-linked immunosorbent assays (ELISAs), and dot-blots. In general, the methods involve binding of an antigen of interest directly or indirectly to a solid support. The solid support may be any material with sufficient surface porosity to allow access by detection antibodies and a suitable surface affinity to bid antigens. Microporous structures are generally preferred, but materials with gel structure in the hydrated state may be used as well. Useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatin; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylates, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, magnesium carbonate, silicates of alkali and alkaline earth metals, aluminum and magnesium; and aluminum or silicon oxides or hydrates, such as clays, alumina, talc, kaolin, zeolite, silica gel, or glass (These materials may be used as fillers with the above polymeric materials); and mixtures or copolymers of the above classes, such as graft copolymers obtained by initiating polymerization of synthetic polymers on a pre-existing natural polymer.

These materials can be used in suitable shapes, such as films, sheets, plates, and wellplates, or they may be coated onto or bonded or laminated to appropriate inert carriers, such as paper, glass, plastic films, or fabrics. The porous structure of nitrocellulose, in particular, has excellent absorption and adsorption qualities for a wide variety of reagents which may be used in the methods of the invention. Nylon also possess similar characteristics and is a suitable support material.

Once the selected antigens have been bound onto the solid support, the support can be processed to block excess binding sites of the porous material before proceeding. This can be done by incubation of the support containing the antigens with non-specific proteins or with a mixture of such proteins, or with total serum, or any combination of these ingredients alone or together. Proteins or other agents used for blocking should not interfere or cross-react with any of the antibodies or antigens in the immunoassays, and they should be different from those mounted on the support.

A. Western Blotting

Western blotting is an accurate method of assaying for the presence of a particular protein antigen within a biological sample. The general methodology of the Western blot includes applying the sample to a polyacrylamide gel and separating the proteins through the technique of gel electrophoresis. The proteins, having been separated into discrete bands, are subsequently transferred to a sheet (e.g., nitrocellulose) using an electrophoretic blotting chamber. Once the protein bands have been transferred, the blot is treated with a primary antibody specific to the particular antigen of interest; if the antigen is present, the primary antibody will bind to the antigen. The primary antibody can be an enzyme-antibody conjugate, wherein the enzyme is capable of oxidizing the hydro/deuterocyanine probes of the present invention. Free antibody is washed away, and the enzyme linked to the antibody can then in turn react with the hydro/deuterocyanine probe applied to the blot which then generates a fluorescent signal. Alternatively, the primary antibody can be bound by secondary antibody-enzyme conjugate. The blot is rinsed again to remove excess secondary antibody-enzyme conjugate, and the enzyme linked to the secondary antibody may then in turn react with the hydro/deuterocyanine probe applied to the blot. The presence of very small quantities of antigen may thus be detected due to the highly sensitive nature of the Western blotting technique.

Alternatively, in another embodiment, the present invention provides a multiplex detection immunoassay utilizing, for example, H-IR780F2 to detect the presence of HRP, and an alkaline phosphatase at different wavelengths by utilizing on the one hand HRP labeled proteins and on the other hand alkaline phosphatase labeled proteins. In yet another embodiment, a fluorescently labeled protein and an HRP labeled protein could be simultaneously detected at different wavelengths.

A Western blot membrane is prepared by denaturing and solubilizing a sample in a sample buffer containing sodium dodecyl sulfate, Tris buffer and other components, and electrophoresed in a polyacrylamide gel following established procedures (e.g., Laemmli gel procedure). The resolved proteins are electrophoretically transferred from the gel to a nitrocellulose membrane by established procedures (Towbin, H. et al., PNAS (USA) 76: 4350-4354 (1979)) and the membrane is saturated with non-specific protein (e.g., solubilized nonfat milk powder). The membrane can then be cut into individual strips for incubation with serum samples, or incubated without cutting. Upon following the typical Western blot processing as described above, bands appear on membranes which have been exposed to serum containing antibodies to the antigen of interest. Reactive non-specific bands without diagnostic significance may also be observed in sera from normal, healthy individuals in certain instances; known bands correlating with seropositivity for the antigen of interest can be determined by other assays so as to properly distinguish them from the non-specific bands if necessary.

A dot-blot procedure can also be used for the immunoassays of the present invention. The dot-blot procedure generally includes applying antibody, which is specific to the antigen of interest, directly to a membrane. The membrane is then washed to remove unbound antibody. The sample containing the antigen of interest is then applied to the membrane, and the antigen subsequently binds to the antibody attached to the membrane. The membrane is again washed to remove unbound molecules, treated with a second antibody specific to a different site on the antigen of interest, and washed to remove unbound enzyme conjugate. This antibody is linked to an enzyme which reacts with a hydro/deuterocyanine substrate to generate a fluorescent signal. The signals appear as dots, rather than bands as in the Western blot, since antigen is applied to the support in a single drop rather than as electrophoretically resolved bands of protein.

The membrane is processed with a serum sample in the same manner as a conventional Western blot membrane as known to those skilled in the art. In a preferred embodiment, the following steps are performed: 1) incubation of the membrane with diluted serum; 2) buffer wash to remove unbound antibody; 3) incubation with enzyme-conjugated anti-immunoglobulin; 4) buffer wash to remove unbound enzyme conjugate; and 5) incubation with enzyme substrate.

B. Enzyme-Linked Immunosorbent Assay

Enzyme-linked immunosorbent assays (ELISAs), can be performed by fixing a reference antigen to a solid phase support. A biological sample suspected of containing the antigen (and primary antibodies to the antigen), can be mixed with a labeled reagent (such as secondary antibody-enzyme conjugate that bind the primary antibodies), and incubated with the fixed antigen. Alternatively, the binding of the primary antibodies to the fixed antigen to form a fixed-antigen/primary antibody duplex can be conducted in a first step. Binding of the duplex by the secondary antibody-enzyme conjugate can then be conducted separately in a second step. In either case, the biological samples and solid support undergo a series of dilution, incubation, and washing steps in order to separate bound and free antibodies. The process is generally concluded with a detection step to indirectly measure the amount of antibody (or antigen) in the test sera. Determining the presence of an antigen in a biological sample by detecting antibodies to the antigen has been characterized as an "indirect" ELISA. In the case of ELISAs conducted with a secondary antibody-peroxidase conjugate, for example, the detection step can include reaction of a bound conjugate with a hydro/deuterocyanine substrate and hydrogen peroxide to produce a detectable fluorescent signal.

The ELISA assay can also be a "sandwich" ELISA. In this assay, an antibody specific to an antigen of interest is fixed to a solid phase or support, and the fixed antibody is then contacted with a sample being tested for the antigen. If the antigen is present in the sample, at least a portion of the antigen will be extracted from the sample via binding by the fixed antibody to form a fixed-antibody/antigen duplex. After a suitable incubation period, the solid support can be washed to remove the residue of the fluid sample and contacted with a solution containing a known quantity of a primary antibody that binds to the fixed-antibody/antigen duplex. The primary antibody can be an antibody-peroxidase conjugate, and detection sing a hydro/deuterocyanine substrate can be detected as described above.

Alternatively, detection of fixed-antibody/antigen complexes can be conducted using a multi-step approach. A fixed-antibody/antigen/primary antibody complex can be detected, for example, using a secondary antibody-enzyme conjugate that has binding affinity for the primary antibody. After processing as described above, detection of the secondary antibody can be conducted using a hydro/deuterocyanine substrate. Alternatively, an unlabeled secondary antibody can be used and detected using a third binding ligand or antibody that is linked to a detectable enzyme. Multi-step procedure can provide high selectivity and low background for sensitive applications. Still other reagents capable of selectively binding or detecting antibody/antigen complexes can also be used in the ELISA assays. Such reagents include, but are not limited to, antibodies or other ligands that can be labeled using a variety of markers, e.g., a biotin/avidin binding pair, as is known in the art. Suitably labeled second and third antibodies can also be used.

The ELISA can also be a "competitive" ELISA. In this assay, a known quantity of a primary antibody to a particular antigen is added to a biological sample suspected of containing the antigen. The biological mixture is incubated under conditions sufficient to form primary antibody/antigen complexes; the biological mixture will generally contain a certain amount of free primary antibody. Meanwhile, a known quantity of the antigen is fixed to a solid support. The support with the fixed-antigen is contacted with the biological mixture containing the primary antibody/antigen complexes and the free primary antibody. Different levels of free primary antibodies will be available for binding to the fixed-antigen on the solid support, depending on the quantity of the antigen in the original biological sample. Detection of fixed-antigen/primary antibody complexes can be conducted with second and third antibodies as described above. The quantity of the antigen in the original biological sample can be determined based on the amount of the primary antibodies detected using the competitive ELISA.

In terms of antigen, antibody or antibody/antigen complex detection, the biological sample analyzed may be any sample that is suspected of containing an antigen or antigen/antibody complex, such as, for example, a tissue section or specimen, a homogenized tissue extract, a cell, an organelle, separated and/or purified forms of any of the above antigen-containing compositions, or any biological fluid that comes into contact with the cell or tissue, including blood and/or serum.

Irrespective of the format employed, ELISAs have certain features in common, such as coating, incubating and binding, washing to remove non-specifically bound species, and detecting the bound immune complexes. A fixed antigen or antibody is generally contacted with a chosen biological sample under effective conditions and for a period of time sufficient to allow the formation of immune complexes. After this time, the ELISA plate can be washed to remove any non-specifically bound species, allowing only specifically-bound immune complexes to be detected. One of skill in the art will recognize that such techniques can also be applied to tissue sections, dot blots, or Western blots as they are to ELISA plates.

In coating a plate with either antigen or antibody, wells of the plate can be incubated with a solution of the antigen or antibody, either overnight or for a specified period of hours.

The wells of the plate can then be washed to remove incompletely adsorbed material. Any remaining available surfaces of the wells can then be "blocked" with a nonspecific protein that is antigenically neutral with regard to the test antisera. Blocking agents include, but are not limited to, bovine serum albumin (BSA), casein, or solutions of milk powder. Blocking can prevent nonspecific adsorption sites on the immobilizing surface and reduce the background caused by nonspecific binding of antisera onto the surface.

After binding of a protein or antibody to the well, blocking, and washing to remove unbound material, the immobilizing surface is generally contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

Biological samples and antibody/antigen compositions can be diluted with solutions such as BSA, bovine gamma globulin (BGG), or phosphate buffered saline (PBS)/Tween. These added agents can assist in the reduction of nonspecific background. Incubation is generally conducted at a temperature or for a period of time sufficient to allow effective binding. For example, incubation can be conducted for about 1 to 4 hours at temperatures around 25° C., or for overnight at around 4° C.

Following all incubation steps in an ELISA, the contacted surface is washed so as to remove non-complexed material. Such procedures can include washing with a solution such as PBS/Tween or borate buffer. Following the formation of fixed-antibody/antigen complexes and subsequent washing, the occurrence of even minute amounts of immune complexes may be determined. To provide a detecting means, a second or third antibody can be conjugated to an enzymatic label to allow for detection using hydro/deuterocyanine substrates as described above. Conditions that favor the development of further immune complex formation are generally used for binding of the fixed-antibody/antigen complex by additional antibodies (e.g., incubation for 2 hours at room temperature in a PBS-containing solution such as PBS-Tween).

In certain instances, the hydrocyanines are useful in imaging ROS in diverse biological experiments. Certain of the reduced dyes disclosed herein (e.g., compounds 1 and 2 of Table 1) are cell permeable with improved water solubility. In addition, the use of the Schlenk technique generates longer storage life. In certain instances, the use of DMSO increases the shelf life of the inventive compounds.

It also is contemplated that reagents may be packaged in a kit that may be produced commercially to measure the soluble antigens, antibodies or antibody/antigen complexes described herein.

The compounds described herein are suitable for use in enzyme histochemistry, immunohistology, immunocytochemistry, immunoassays, immunofluorescent assays, immunoprecipitation assays, ELISA, flow cytometry, fluorescent activated cell sorting, radioimmunochemistry, electrophoresis, two-dimensional gel electrophoresis, Western blotting, protein sequencing, mass spectrometry, proteomic analysis, and protein microarray analysis. With regard to protein microarray analysis, a product from R&D Systems known as the Proteome Profiler™ 96 Phospho-RTK Array 1 is suitable for use. The Proteome Profiler 96 Human Phospho-RTK Array 1 (Catalog #ARZ001) employs a two-site sandwich immunoassay technique to simultaneously detect multiple analytes (e.g., 16 phosphorylated receptor tyrosine kinases) in a single sample of cell lysate. Multiple capture antibodies that specifically recognize the target detected by the assay are spotted into each well of a 96-well microplate.

VIII. Examples

The following examples are offered to illustrate, but not to limit the claimed invention.

Example 1

IR780, IRDye® 800CW, or IRDye® 680RD (0.2 mmol) (each commercially available) is dissolved in 5 ml of methanol. The mixture is placed in a 25-ml flask covered with aluminum foil. Sodium borohydride (3 mg, 0.08 mmol in 0.5 ml methanol) is slowly added dropwise to the cyanine dye solution for reduction. After the addition is complete, the mixture is stirred for 10 minutes or until monitoring revealed that the reaction is complete. The reaction mixture is stirred an additional 10 minutes before removing the solvent under reduced pressure. The crude product is then purified by silica gel chromatography using hexanes/ethyl acetate as the eluent.

Deuterocyanines are prepared using the procedure above except sodium borohydride is replaced with sodium borodeuteride (i.e., NaBD$_4$).

Example 2

Preparation of Sodium 2-((1E,3Z,5E)-3-Bromo-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

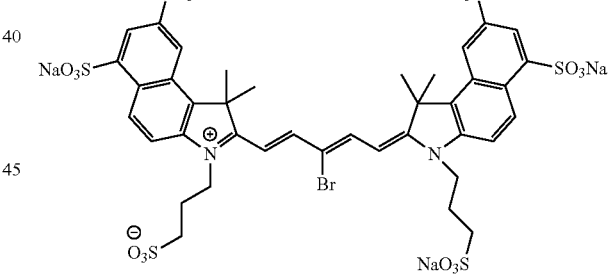

Sodium 2-((1E,3Z,5E)-3-Bromo-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (1)

A 100 ml round bottom flask fitted with a reflux condenser was charged with sodium 1,1,2-trimethyl-3-(3-sulfonatopropyl)-1H-benzo[e]indolium-6,8-disulfonate (565 mg, 1 mmol), (E)-N—((Z)-2-bromo-3-(phenylamino)allylidene)benzenaminium bromide (150 mg, 0.5 mmol), and pyridine (1 ml). Acetic anhydride (10 ml) was added to the flask, and the mixture was heated at 115° C. for 2 h, cooled to room temperature, and diluted with 25 ml of ethyl ether. The resulting dark blue dye precipitate was collected by filtration, then dissolved in 20 ml of water and purified by preparative reverse-phase HPLC to afford the compound 1 as a blue powder (285 mg, 50%; UV/vis absorption max 674 nm).

Example 3

Preparation of Sodium 2-((1E,3Z,5E)-3-Bromo-5-(1,1-dimethyl-6,8-disulfonato-3-(3-sulfonatobutyl)-1H-benzo[e]indol-2(3H)-ylidene)penta-1,3-dienyl)-1,1-dimethyl-3-(3-sulfonatobutyl)-1H-benzo[e]indolium-6,8-disulfonate

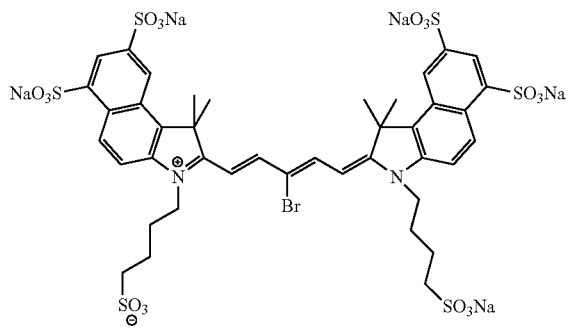

Sodium 2-((1E,3Z,5E)-3-Bromo-5-(1,1-dimethyl-6,8-disulfonato-3-(3-sulfonatobutyl)-1H-benzo[e]indol-2(3H)-ylidene)penta-1,3-dienyl)-1,1-dimethyl-3-(3-sulfonatobutyl)-1H-benzo[e]indolium-6,8-disulfonate (2)

Compound 2 was prepared analogously to compound 1 (Example 2).

Example 4

Preparation of Sodium 2-((1E,3Z,5E)-3-(3-(4-Carboxybutyl)phenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

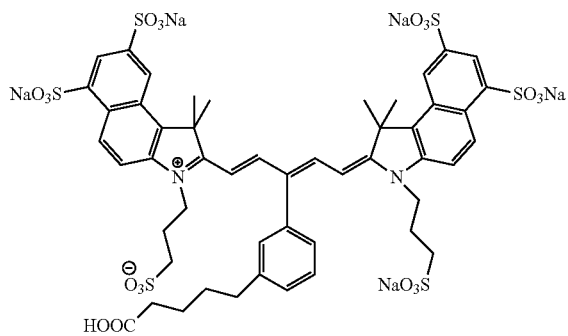

Sodium 2-((1E,3Z,5E)-3-(3-(4-Carboxybutyl)phenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (3)

Compound 1 (80 mg), 3-(4-carboxybutyl)phenylboronic acid (40 mg), and cesium carbonate (20 mg) are stirred into 1:1 water:ethanol (10 ml) under nitrogen at room temperature. Tetrakis(triphenylphosphine)palladium(0) (10 mg) is added to the reaction mixture. The mixture was refluxed for 4 hours, and the solvent and volatile compounds are evaporated under vacuum. The crude product is purified by flash chromatography on reverse-phase C18-functionalized silica by eluting with a 1:4 acetonitrile:water mixture. The purified product 3 has UV/vis absorption max of $\lambda_{MeOH}$=680 nm, $\epsilon$=229,000; $\lambda_{PBS}$=676 nm, $\epsilon$=239,000.

Example 5

Preparation of Sodium 2-((1E,3Z,5E)-5-(1,1-Dimethyl-6,8-disulfonato-3-(3-sulfonatopropyl)-1H-benzo[e]indol-2(3H)-ylidene)-3-(3-(5-(2,5-dioxopyrrolidin-1-yloxy)-5-oxopentyl)phenyl)penta-1,3-dienyl)-1,1-dimethyl-3-(3-sulfonatopropyl)-1H-benzo[e]indolium-6,8-disulfonate

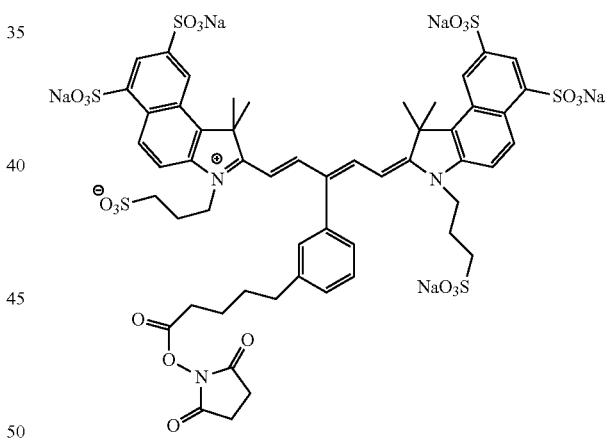

Sodium 2-((1E,3Z,5E)-5-(1,1-Dimethyl-6,8-disulfonato-3-(3-sulfonatopropyl)-1H-benzo[e]indol-2(3H)-ylidene)-3-(3-(5-(2,5-dioxopyrrolidin-1-yloxy)-5-oxopentyl)phenyl)penta-1,3-dienyl)-1,1-dimethyl-3-(3-sulfonatopropyl)-1H-benzo[e]indolium-6,8-disulfonate (4)

To a solution of compound 3 (200 mg) in dry DMSO (15 ml) was added diisopropylethylamine (150 μL) and N,N'-disuccinimidyl carbonate (82 mg). The mixture was stirred at room temperature for 2 hours and then precipitated into diethyl ether (200 mL). The crude reaction mixture was purified on reverse-phase silica gel using acetonitrile/water eluent to yield the succinimidyl ester (120 mg, 60%).

Example 6

Preparation of Sodium 2-((1E,3Z,5E)-3-(3-(2-Carboxyethyl)phenyl)-5-(1,1-dimethyl-6,8-disulfonato-3-(4-sulfonatobutyl)-1H-benzo[e]indol-2(3H)-ylidene)penta-1,3-dienyl)-1,1-dimethyl-3-(4-sulfonatobutyl)-1H-benzo[e]indolium-6,8-disulfonate

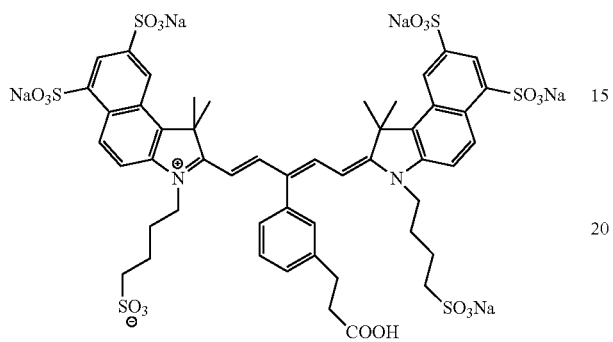

Sodium 2-((1E,3Z,5E)-3-(3-(2-Carboxyethyl)phenyl)-5-(1,1-dimethyl-6,8-disulfonato-3-(4-sulfonatobutyl)-1H-benzo[e]indol-2(3H)-ylidene)penta-1,3-dienyl)-1,1-dimethyl-3-(4-sulfonatobutyl)-1H-benzo[e]indolium-6,8-disulfonate (5)

Compound 5 was prepared analogously to compound 3, except that 3-(3-boronophenyl)propionic acid is used as a starting material.

Example 7

Preparation of Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate

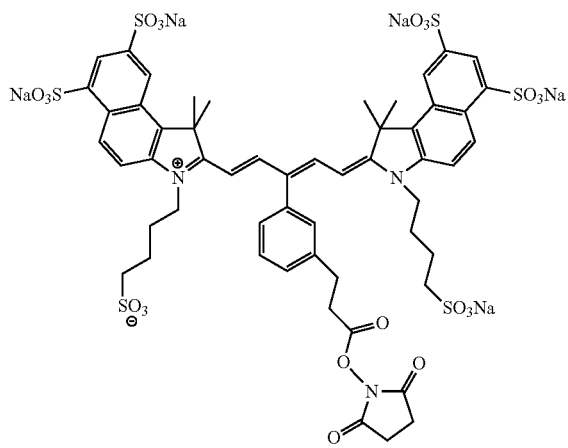

Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate (6)

Compound 6 was prepared using methods of the present invention using compound 5 as starting material.

Example 8

Preparation of Sodium (E)-2-((2Z,4E)-3-Bromo-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (7)

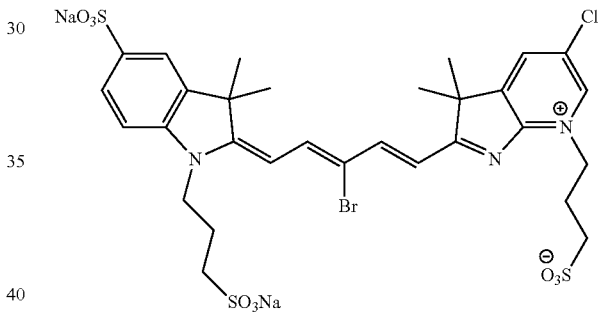

Sodium (E)-2-((2Z,4E)-3-Bromo-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (7)

A 100-mL round-bottom flask fitted with a reflux condenser was charged with 3-(5-chloro-2,3,3-trimethyl-3H-pyrrolo[2,3-b]pyridin-7-ium-7-yl)propane-1-sulfonate (500 mg), sodium 2,3,3-trimethyl-1-(3-sulfonatopropyl)-3H-indolium-5-sulfonate (500 mg), (E)-N—((Z)-2-bromo-3-(phenylamino)allylidene)benzenaminium bromide (100 mg), sodium acetate (650 mg), and methanol (40 mL) were added to the flask. The mixture was heated at 50° C. for 5 h, allowed to cool to room temperature, and diluted with ethyl ether (25 mL). The resulting dark blue dye precipitate was collected by filtration, dissolved in water (20 mL), and purified by preparative reverse-phase HPLC to afford the 7 as a blue powder (285 mg, 50%, UV 668 nm).

Example 9

Preparation of Sodium (E)-2-((2Z,4E)-3-(3-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (8)

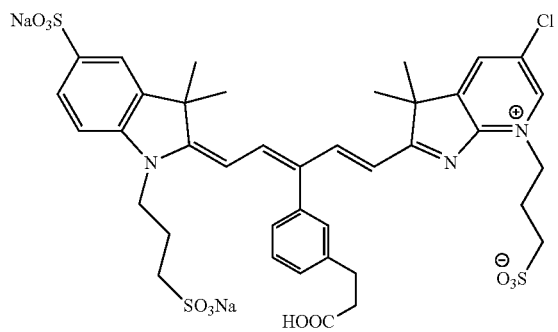

Sodium (E)-2-((2Z,4E)-3-(3-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (8)

Compound 7 (80 mg), 3-(2-carboxyethyl)phenylboronic acid (40 mg), and cesium carbonate (20 mg) were stirred into water (20 mL) under nitrogen at room temperature. Tetrakis(triphenylphosphine)palladium (0) (10 mg) were added to the reaction mixture. The mixture was refluxed for 4 h, and the solvent and volatile compounds then were evaporated under vacuum. The crude product was purified by flash chromatography on reverse-phase silica with an acetonitrile/water mixture as the eluent. The purified compound had $\lambda_{MeOH}$=680 nm, $\lambda_{PBS}$=672 nm, $\epsilon$=160,000.

TABLE 2

Absorption and Emission of Compound 8

| | Extinction Coefficient | Max. Abs. (nm) | Max. Emis. (nm) |
|---|---|---|---|
| PBS | 160,000 | 672 | 694 |
| MeOH | 170,000 | 680 | 694 |

Example 10

Reduced hydrocyanine dyes (H- or D-versions) are non-fluorescent, but turn fluorescent upon oxidation. This activation property was exploited to utilize the reduced hydrocyanine dyes as horseradish peroxidase (HRP) substrates. In certain embodiments of an enzymatic assay, the hydrocyanines can be oxidized by HRP using hydrogen peroxide as the oxidizing agent, yielding a fluorescent signal. In some preferred embodiments, this fluorescent signal's wavelength can range from 530-900 nm depending on the structure of the dye.

The following two dyes were synthesized and then tested in an enzymatic assay:

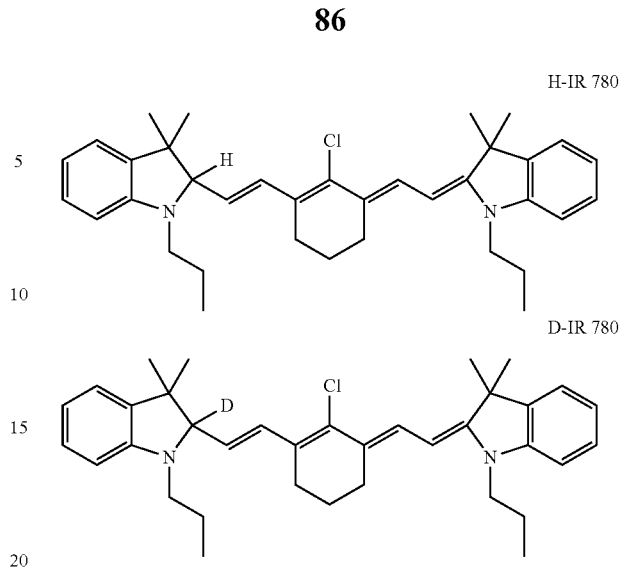

Synthesis of H-IR 780: To an oven-dried 250-mL round-bottomed flask with a stir-bar and septum under $N_2$ were added IR-780 (100 mg, 0.125 mmol), followed by methanol (100 mL). To the resulting green solution, sodium borohydride (19.0 mg, 5.0 mmol) was slowly added over 5 min. The solution turned light yellow, and the mixture was stirred @ambient temperature for an additional 15 min. The solvent was removed under reduced pressure, and the product was purified by CombiFlash system (i.e., automated flash chromatography) using hexane/ethyl acetate as eluent.

Synthesis of D-IR 780: To an oven-dried 250-mL round-bottomed flask with a stir-bar and septum under $N_2$ were added IR-780 (100 mg, 0.125 mmol), followed by methanol (100 mL). To the resulting green solution, sodium borodeuteride (21.0 mg, 5.0 mmol) was slowly added over 5 min. The solution turned light yellow, and the mixture was stirred @ambient temperature for an additional 15 min. The solvent was removed under reduced pressure, and the product was purified by CombiFlash system using hexane/ethyl acetate as eluent.

HRP 800 Assay Buffer: The HRP 800 Assay Buffer contains 60 µM Hydrogen Peroxide, 0.2 µg/mL Acetanilide, 0.02% Triton X-100, in 100 mM Citrate Buffer, pH 3.0.

H-IR 780 Substrate solution: 10 µM H-IR 780 in the HRP 800 Assay Buffer.

D-IR 780 Substrate solution: 10 µM D-IR 780 in the HRP 800 Assay Buffer.

The utility of the H-IR 780 and D-IR 780 as a HRP substrate was tested by reaction of the dye with an enzyme-labeled antibody. The substrate, when oxidized by HRP and hydrogen peroxide, yields a fluorescent signal at approximately 800 nm in the NIR. Briefly, 100 µl of either H-IR 780 substrate solution (B01-B12) or D-IR 780 substrate solution (C01-C12 and D01-D12) in the HRP assay buffer was added to the wells of 96-well plate followed by the addition of 10 µl of goat anti-mouse HRP-labeled antibody (GAM-HRP) at a concentration of 0.8 µg/ml to 0.8 pg/ml. Wells B12, C12 and D12 received 10 µL of PBS buffer (pH 7.2) and were used as a control to measure the background fluorescence. The plate was incubated at ambient temperature for 10 minutes and scanned using a LI-COR® Odyssey® imager (Channel: 800 nm, Sensitivity: 5, Focus Offset: 3.5).

The results (FIG. 1) showed that the intensity of the fluorescence signal increased with increasing concentration of GAM-HRP. Since the fluorescence response was dependent on the concentration of the GAM-HRP, proof of concept for use of hydrocyanine dyes as HRP substrates was demonstrated. This demonstrates the utility of H-IR-780 as a HRP substrate for an in-cell Western blot. FIG. 1 shows the usefulness of H-IR-780 as an HRP substrate.

Example 11

Near-infrared (NIR) HRP substrates using hydrocyanine dyes have been tested and qualified using direct ELISA assays. The substrate, when oxidized by HRP using hydrogen peroxide as the oxidizing agent, yields a fluorescent signal at approximately 800 nm in the NIR.

Initial feasibility testing focused on optimizing individual assay buffer components including pH and hydrogen peroxide concentration. Further testing considered the effects of substrate concentration, HRP enzyme concentration, surfactant selection and surfactant concentration (above and below the Critical Micelle Concentration). Once these parameters were optimized, a direct ELISA assay was performed.

Briefly, serially diluted Rabbit IgG was immobilized (via adsorption to the surface) on a high binding 96-well plate. Unbound IgG was removed and any remaining binding sites on the plate surface were blocking using Superblock (ThermoFisher Pierce). After blocking, the detection antibody (Goat anti-Rabbit HRP) was added and complexed with bound IgG. The plate was washed with 1X PBS containing 0.1% Tween 20 to remove excess detection antibody. The NIR HRP substrate was then added in assay buffer (0.1M sodium citrate pH 4 with 0.1% Triton and 60 µM hydrogen peroxide). The plate was incubated at ambient temperature (FIG. 1).

Figure 2:
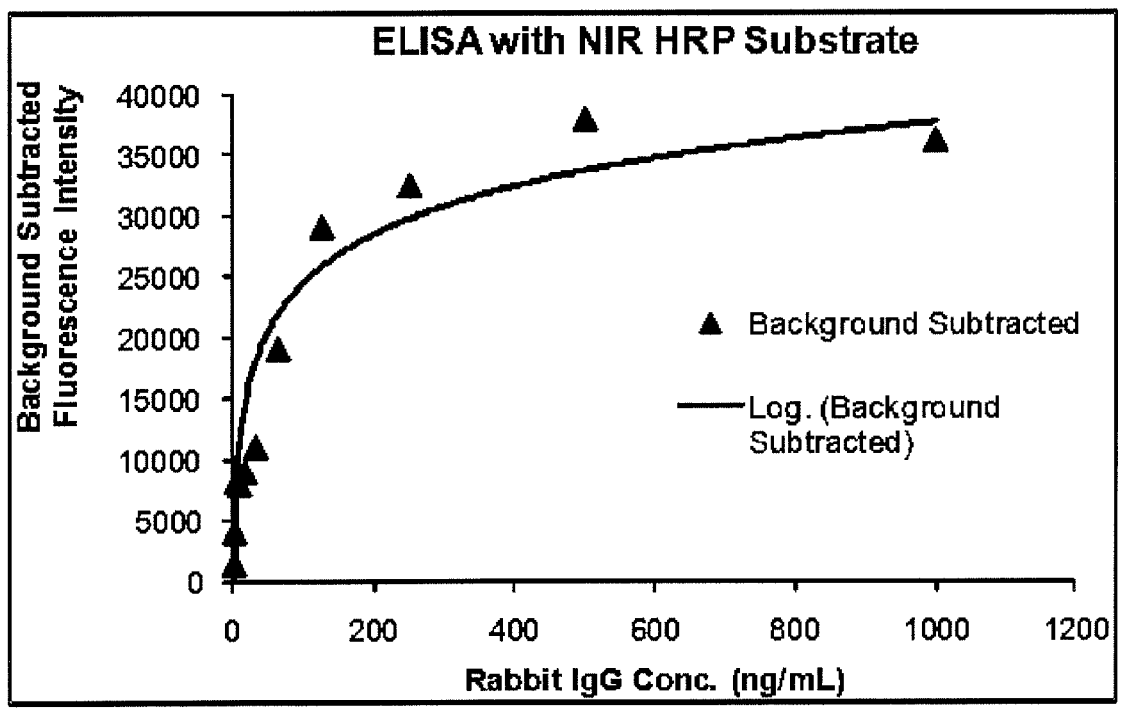
FIG. 2 shows an NIR HRP substrate in a direct ELISA assay using rabbit immunoglobulin G (IgG) as antigen and goat anti-rabbit HRP as the detection antibody.

Results showed that the intensity of the fluorescence signal increased with increasing concentration of Rabbit IgG. Since the fluorescence response was dependent on the concentration of the Rabbit IgG, proof of concept for use of hydrocyanine dyes as HRP substrates was demonstrated. FIG. 2 shows an NIR HRP Substrate in Direct ELISA Assay Using Rabbit IgG (Antigen) and Goat Anti-Rabbit HRP Detection Antibody.

Example 12

Hydrocyanines: New tools to study effects of ROS in Hypoxia. Reactive oxygen species (ROS), such as oxygen free radicals, play an exceedingly important role in cancer cell response to growth factor signaling and hypoxia. Recent studies suggest that oxygen depletion stimulates mitochondria to overproduce ROS, with subsequent activation of the transcription factor hypoxia-inducible factor 1a (HIF1a), and thus promoting cancer cell survival and tumor growth. Furthermore, as mitochondria plays a major role in the chemotherapy induced apoptosis induction, the intricate relationships among mitochondria, ROS signaling and activation of survival pathways under hypoxic conditions have drawn tremendous interests.

We present a number of near-infrared hydrocyanine probes as tools for imaging ROS for in vitro cell culture, ex vivo tissue section, and most importantly in vivo. Hydrocyanine probes are capable of detecting ROS in fluorescence microscope, fluorescence plate reader, flow cytometry and in vivo imaging platforms with high specificity and excellent sensitivity. There are several advantages for using hydrocyanine probes including 1) ease of use, 2) excellent sensitivity and specificity, 3) multiplexing assays with other cell health detection agents and 4) unprecedented flexibility in terms of imaging platforms and biological systems. Near-infrared hydrocyanine probes therefore, can potentially be used to study the ROS mediated cell signaling pathways under hypoxic conditions.

Example 13

The following hydrocyanines and deuterocyanines were synthesized. Their excitation and emission wavelengths are suitable to be imaged in the 800 channel.

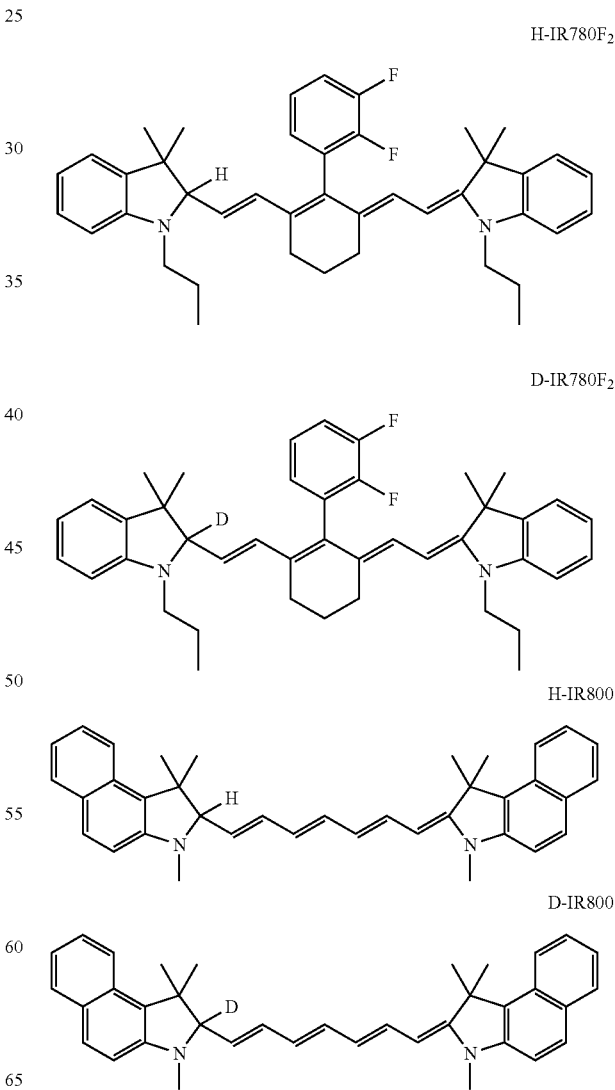

| DIR780F2-P: Two Hours at Ambient Temperature | | | | | | | | | | | | |
|---|---|---|---|---|---|---|---|---|---|---|---|---|
| Trifon X-100 | pH 5 | | | | | | pH 6 | | | | | |
| (%) | 0.1 | | 0.05 | | 0.01 | | 0.1 | | 0.05 | | 0.01 | |
| −Enzyme | 14612 | 15268 | 15096 | 16995 | 14729 | 17889 | 21194 | 15983 | 17026 | 16006 | 12646 | 15381 |
|  | 14653 | 14330 | 15697 | 16257 | 16731 | 18713 | 19749 | 14897 | 14316 | 14644 | 12242 | 12600 |
| +Enzyme | 86168 | 78778 | 110308 | 116984 | 111403 | 107251 | 73669 | 63411 | 71667 | 72420 | 65943 | 71002 |
|  | 79940 | 81063 | 91720 | 95384 | 95434 | 93017 | 72029 | 67718 | 73540 | 65401 | 70952 | 72922 |
| Mean Background | 14716 | | 16011 | | 17016 | | 17956 | | 15498 | | 13218 | |
| Mean Signal | 81487 | | 103599 | | 101776 | | 69207 | | 70757 | | 70205 | |
| Signal-Background | 66771 | | 87588 | | 84761 | | 51251 | | 55259 | | 56987 | |

A. Synthesis of IR 780F2

To an oven dried pressure tube with a magnetic stir-bar were added IR-780 (400 mg, 0.74 mmol), 2,3-difluoro phenyl boronic acid (1.17 g, 6.23 mmol), palladium (0) tetrakis (222 mg), 4.5 mL THF and 1.5 mL nano-pure water followed by 1.44 mL DIPEA. The reaction mixture was flashed with $N_2$ and was heated to 115° C. for 2 h. Mass spectral analysis indicated only the desired product with a very little peak corresponding to the decholinated starting material (m/z=506). The product was purified using Teledyne's Isco CombiFlash system using dichloromethane/methanol as eluent.

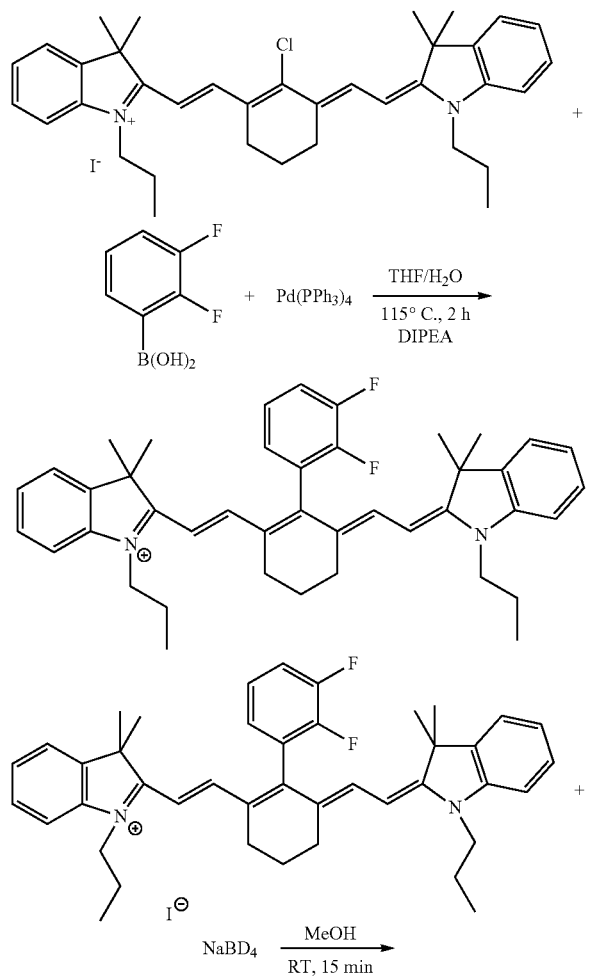

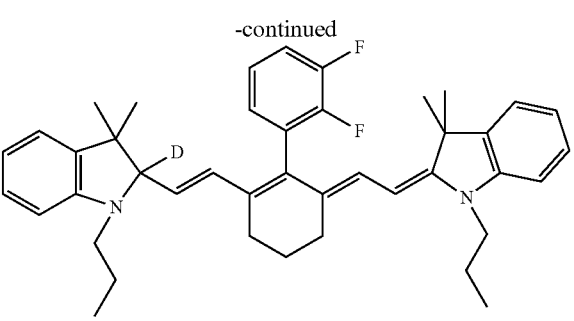

IR-780-F2 (50 mg)+methanol (20 mL); turned a green clear solution. $NaBD_4$ (10.2 mg) were added slowly. The solution turned bright yellow. The reaction mixture was stirred @RT for 15 min and the product formation and the disappearance of the starting material was observed in mass spec analysis. Silica gel (~1 g) was added and the solvent was removed to obtain a yellow sample coated silica gel. The solid silica gel coated reaction mixture was then loaded in the CombiFlash system and the product was purified using hexane/ethyl acetate as eluent. The mass spectrometric results confirmed the product H-IR 780F2.

H-IR 780F2, H-IR 800 and D-IR 800 were synthesized following similar synthetic procedure as described above.

B. 800 HRP SUBSTRATE

Figure 3:
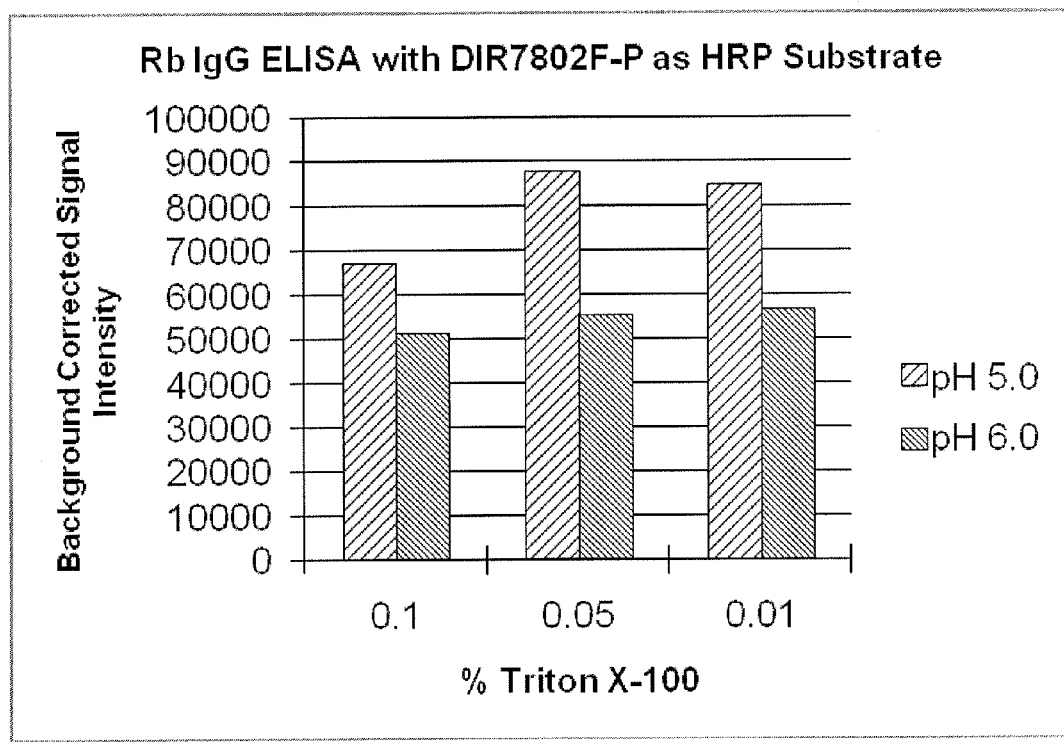
FIG. 3 illustrates the efficacies of D-IR780F2 as an 800 HRP substrate in an ELISA format.
Figures 4A, 4B:
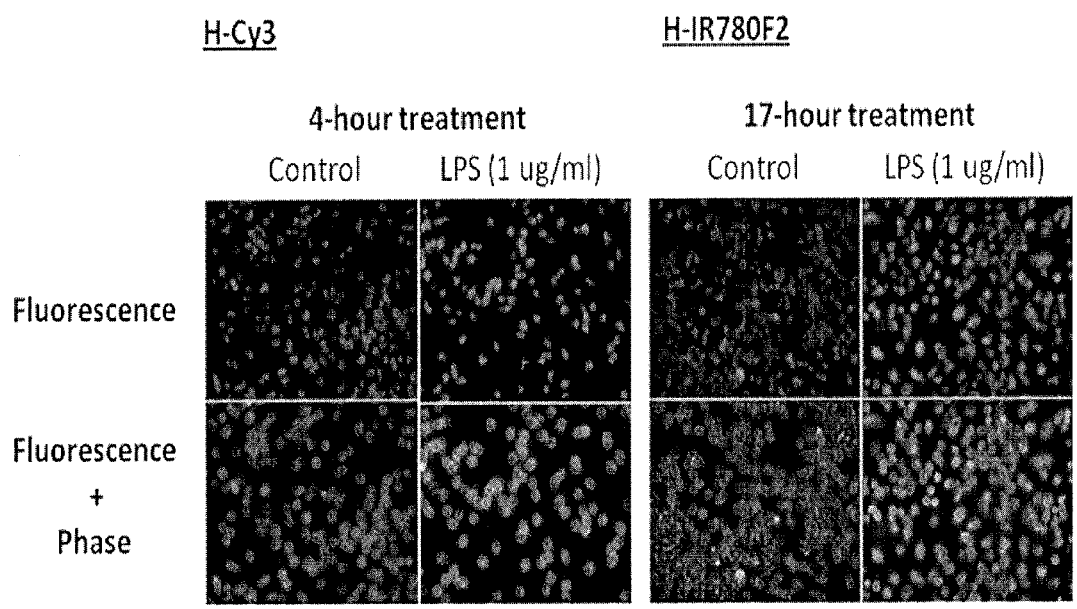
FIG. 4 A-B show representative examples of ROS imaging by H-Cy3 (FIG. 4A) and H-IR780F2 (FIG. 4B). Both H-Cy3 and H-IR780F2 showed increased fluorescent intensity in the LPS treated cells compared to the untreated cells.

Their efficacies as 800 HRP substrates have been tested in the ELISA format. The results with D-IR780F2 as the 800 HRP substrate are shown in FIG. 3.

C. NIR Chemifluorescent Substrates:

800 Chemifluorescent Substrates: The following 800 chemifluorescent substrates were designed.

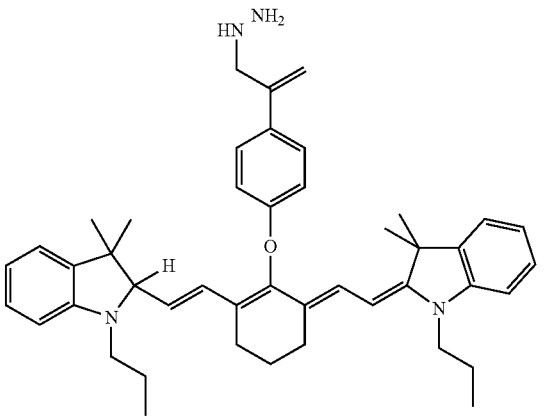

1

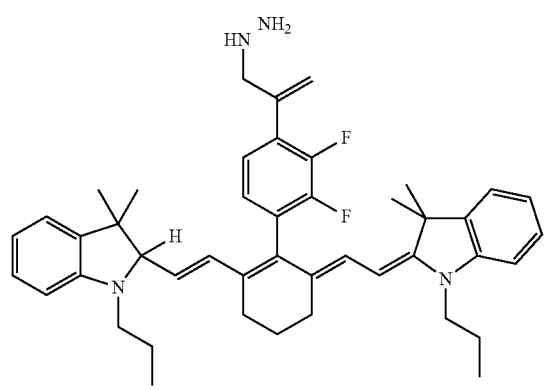
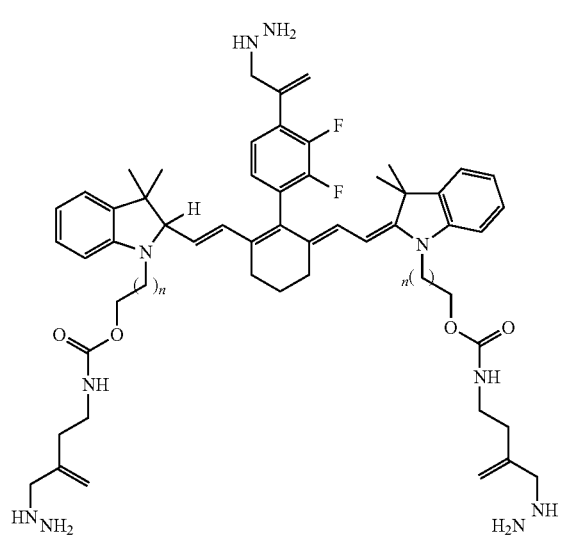
(n = 5)
The chemifluorescent was synthesized by a straightforward four-step synthetic procedure.
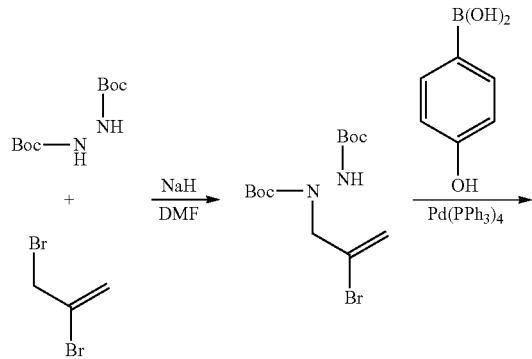
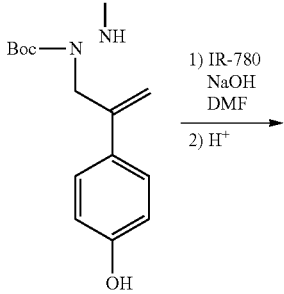
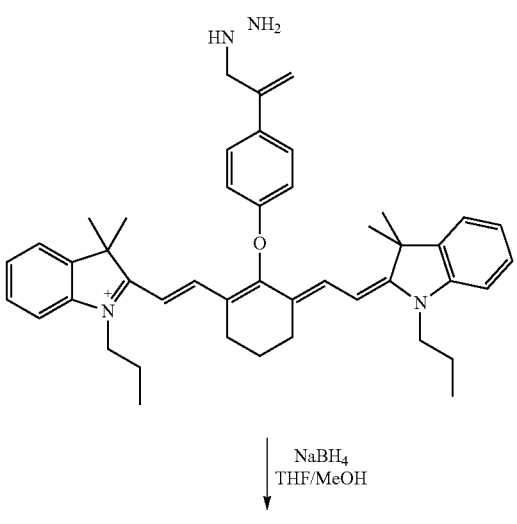
700 Chemifluorescent Substrates: The following 700 substrates were designed.
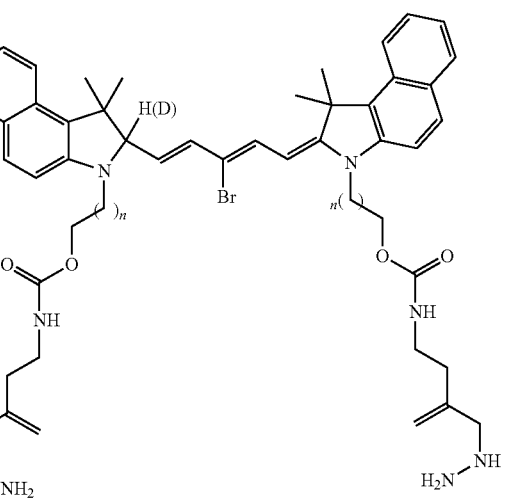

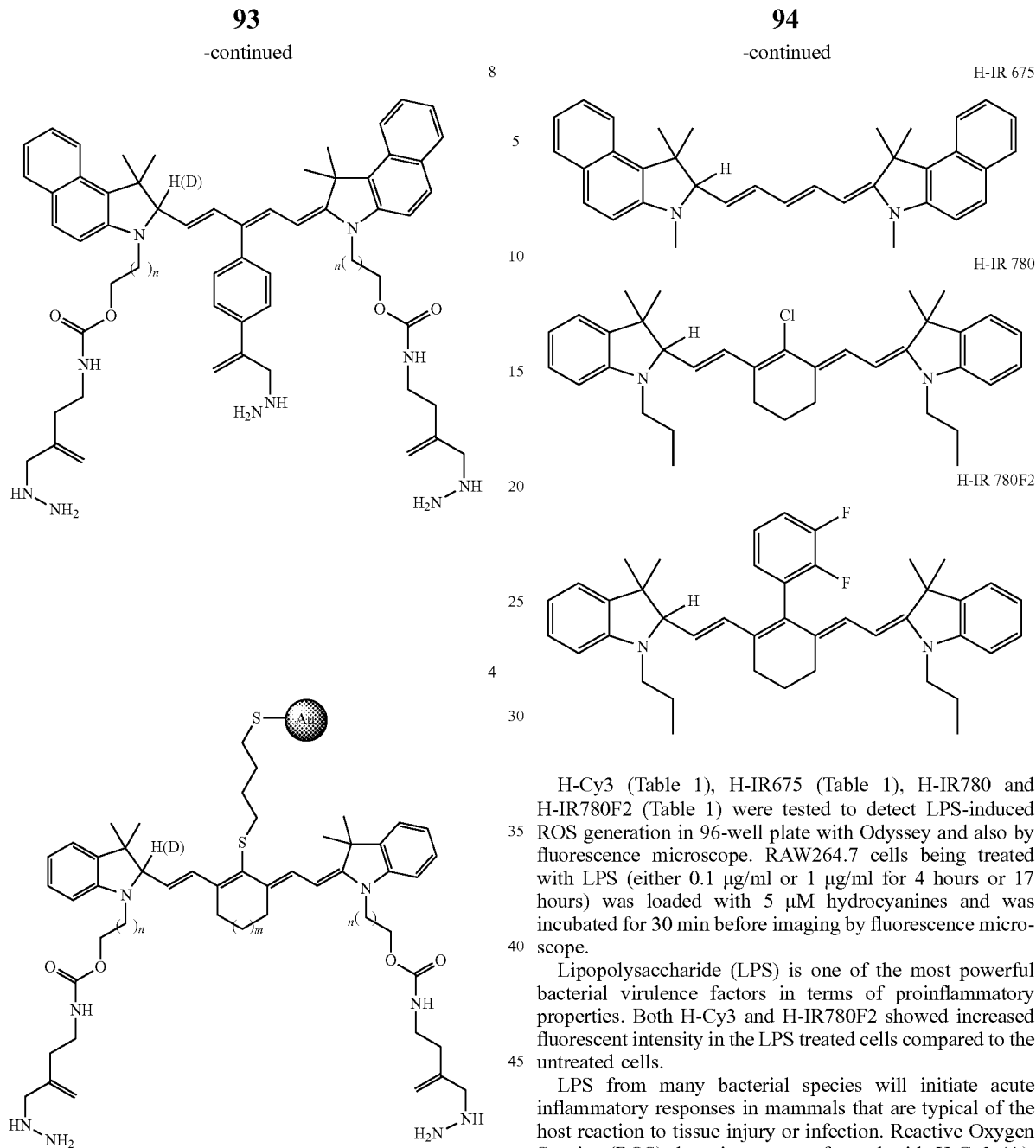

D. Imaging Reactive Oxygen Species (ROS):

Four hydrocyanines (H-Cy3, H-IR675, H-IR780, and H-IR780F2) were synthesized by the reduction of the corresponding cyanine dyes. The hydrocyanines were further tested for imaging lipopolysaccharides (LPS) induced ROS generation in RAW264.7 macrophages.

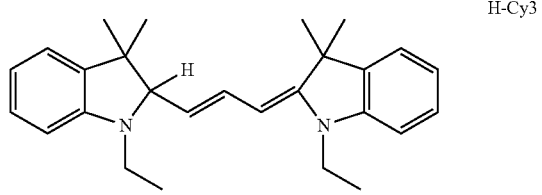

H-Cy3 (Table 1), H-IR675 (Table 1), H-IR780 and H-IR780F2 (Table 1) were tested to detect LPS-induced ROS generation in 96-well plate with Odyssey and also by fluorescence microscope. RAW264.7 cells being treated with LPS (either 0.1 μg/ml or 1 μg/ml for 4 hours or 17 hours) was loaded with 5 μM hydrocyanines and was incubated for 30 min before imaging by fluorescence microscope.

Lipopolysaccharide (LPS) is one of the most powerful bacterial virulence factors in terms of proinflammatory properties. Both H-Cy3 and H-IR780F2 showed increased fluorescent intensity in the LPS treated cells compared to the untreated cells.

LPS from many bacterial species will initiate acute inflammatory responses in mammals that are typical of the host reaction to tissue injury or infection. Reactive Oxygen Species (ROS) detection was performed with H-Cy3 (A), wherein the microscope setting: DSRED (Ex545/30×, T750P; EM620/60M); Phase; 20× Load the dye for 2 hours then treat cells for 30 minutes; and Reactive Oxygen Species (ROS) detection with H-IR780F2 (B), wherein the microscope setting: Cy7 (Ex710/75, DC760LP; EM810/90); Phase; 20× Load the dye for 2 hours then treat cells for 30 minutes.

Example 14

Synthesis of Hydrocyanines

Figure 5:
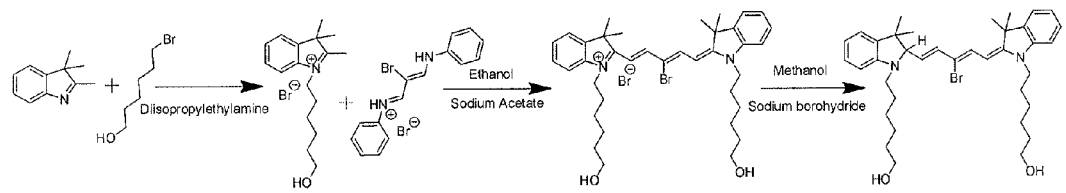
FIG. 5 shows a synthetic route for the preparation of H/D-IR650 diol.

H-IR650DIOL (i.e., 6-((E)-2-((2Z,4E)-3-bromo-5-(1-(6-hydroxyhexyl)-3,3-dimethylindolin-2-yl)penta-2,4-dien-1-ylidene)-3,3-dimethylindolin-1-yl)hexan-1-ol) was synthesized according to FIG. 5.

Synthesis of Indole Hexanol Quaternary Salt: To an oven dried 100-mL round bottom flask with stir bar and septum under N$_2$ were added 2,3,3-trimethylindolenine (4.81 g, 30.21 mmol), followed by 6-bromohexanol (7.09 g, 39.16 mmol) and diisopropylethylamine (1.93 g, 15.0 mmol). The reaction mixture was heated at 80° C. for 16 hours. The reaction mixture was triturated with 90 mL of diethyl ether to produce a powder. The powder was filtered away from the supernatant and washed 3×30 mL with diethyl ether. The powder was dried under vacuum and 6.12 g (60% yield) was recovered.

Synthesis of 650 Diol: To an oven dried 50-mL pressure tube with stir bar were added Indole hexanol quaternary Salt (1.00 g, 2.94 mmol), followed by bromo Schiff base (0.64 g, 1.67 mmol), sodium acetate (0.49 g, 5.97 mmol) and ethanol (10 mL). The reaction was purged with N$_2$, capped and heated at 100° C. for 30 minutes. Silica gel (5 g) was added and the solvent was removed to obtain a blue sample coated silica gel. The solid silica gel coated reaction mixture was then loaded in the CombiFlash system and the product was purified using water/methanol as eluent. Blue/purple crystals were obtained (0.264 g, 22% yield) and mass spectrometric analysis confirmed the product (633.5 m/z+, observed; 633.3 m/z+, expected). $^1$H-NMR (500 MHz, CD$_3$OD): δ 8.43 (d, J=13.3 Hz, 2H), 7.58 (d, J=7.6 Hz, 2H), 7.47 (t, J=7.25 Hz, 2H), 7.42 (d, J=7.9 Hz, 2H), 7.36 (t, J=7.6 Hz, 2H), 6.54 (d, J=13.2 Hz, 2H), 4.23 (t, J=7.26 Hz, 4H), 3.58 (t, J=6.3 Hz, 4H), 1.92 (comp, 4H), 1.79 (s, 12H), 1.57 (comp, 12H).

Synthesis of H-650 Diol: To an oven dried 50-mL round bottom flask was added the 650 diol (0.051 g, 71.37 μmol), followed by methanol (51 mL); turned a blue/purple solution. Sodium borohydride (0.0041 g, 108.4 μmol) was added. The solution changed to pale yellow. The reaction mixture was stirred at room temperature for 15 minutes. Silica gel (2 g) was added and the solvent was removed to obtain a yellow sample coated silica gel. The solid gel coated reaction mixture was then loaded in the CombiFlash system and the product was purified using hexane/ethyl acetate as eluent. A total of 0.0233 g (51.4% yield) were obtained and mass spectrometric analysis confirmed the product (635.5 m/z+, observed; 635.7 m/z+, expected).

Figure 6:
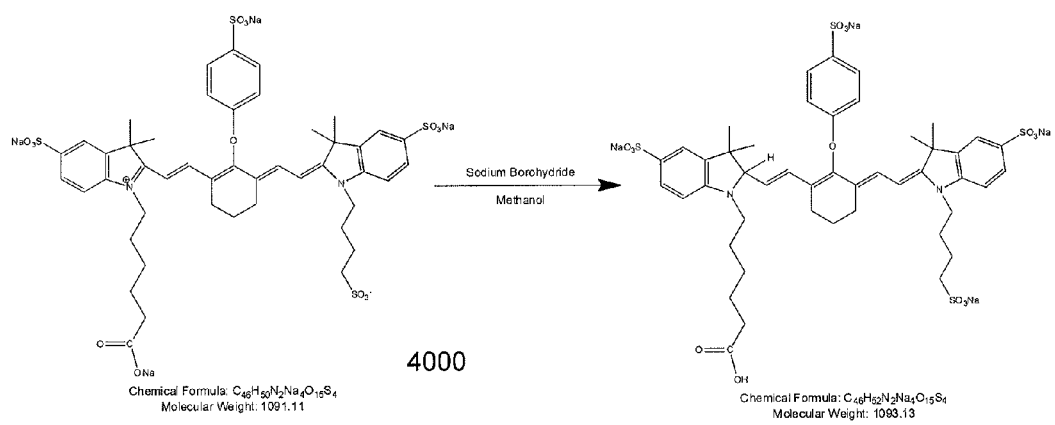
FIG. 6 shows a synthetic route to H-IRDye® 800CW from the corresponding cyanine.

Synthesis of H-IRDye® 800CW: To an oven dried 50-mL round bottom flask was added 800CW carboxylate (0.064 g, 58.66 μmol), followed by methanol (64 mL); turned a clear green solution. Sodium borohydride (0.0048 g, 126.9 μmol) was added. The solution changed to bright yellow/orange. The reaction mixture was stirred at room temperature for 15 minutes. Silica gel (2 g) was added and the solvent was removed to obtain a yellow/orange sample coated silica gel. The solid gel coated reaction mixture was then loaded in the CombiFlash system and the product was purified using water/acetonitrile as eluent. A total of 0.0329 g (51.3% yield) were obtained and mass spectrometric analysis confirmed the product (1004.3 m/z+, observed; 1004.5 m/z+, expected). $^1$H-NMR (500 MHz, D2O): δ 7.78 (d, J=7.25, 2H), 7.58 (d, J=8.51, 1H), 7.51 (comp, 3H), 7.42 (s, 1H), 7.19 (d, J=7.90, 2H), 6.8 (comp, 1H), 6.73 (comp, 2H), 6.63 (d, J=8.51, 1H), 5.85 (dd, J=9.46, 1H), 5.55 (d, J=12.3, 1H), 3.75 (comp, 4H), 3.11 (comp, 2H), 2.92 (comp, 4H), 2.59 (comp, 4H), 2.15 (comp, 4H), 1.90 (comp, 2H), 1.68 (comp, 2H), 1.60 (comp, 2H), 1.57 (comp, 2H), 1.49 (comp, 2H), 1.40 (comp, 2H), 1.34 (comp, 12H). See FIG. 6.

Example 15

In Vitro ROS Detection with Hydrocyanines

ROS detection in LPS-treated RAW cells with H-IR650DIOL. Mouse macrophase cells, RAW 264.7, were treated with lipopolysaccharide endotoxin (LPS; 500 ng/mL) for 24 hrs prior to incubation with H-IR650DIOL (5 μM) for 30 min. Cells were imaged by fluorescence microscopy, as shown in FIG. 7 (microscope settings: Cy5 (1893 ms) (Ex620/60, DC660LP; EM7000/75); Phase (38 ms); 40X).

Figure 8:
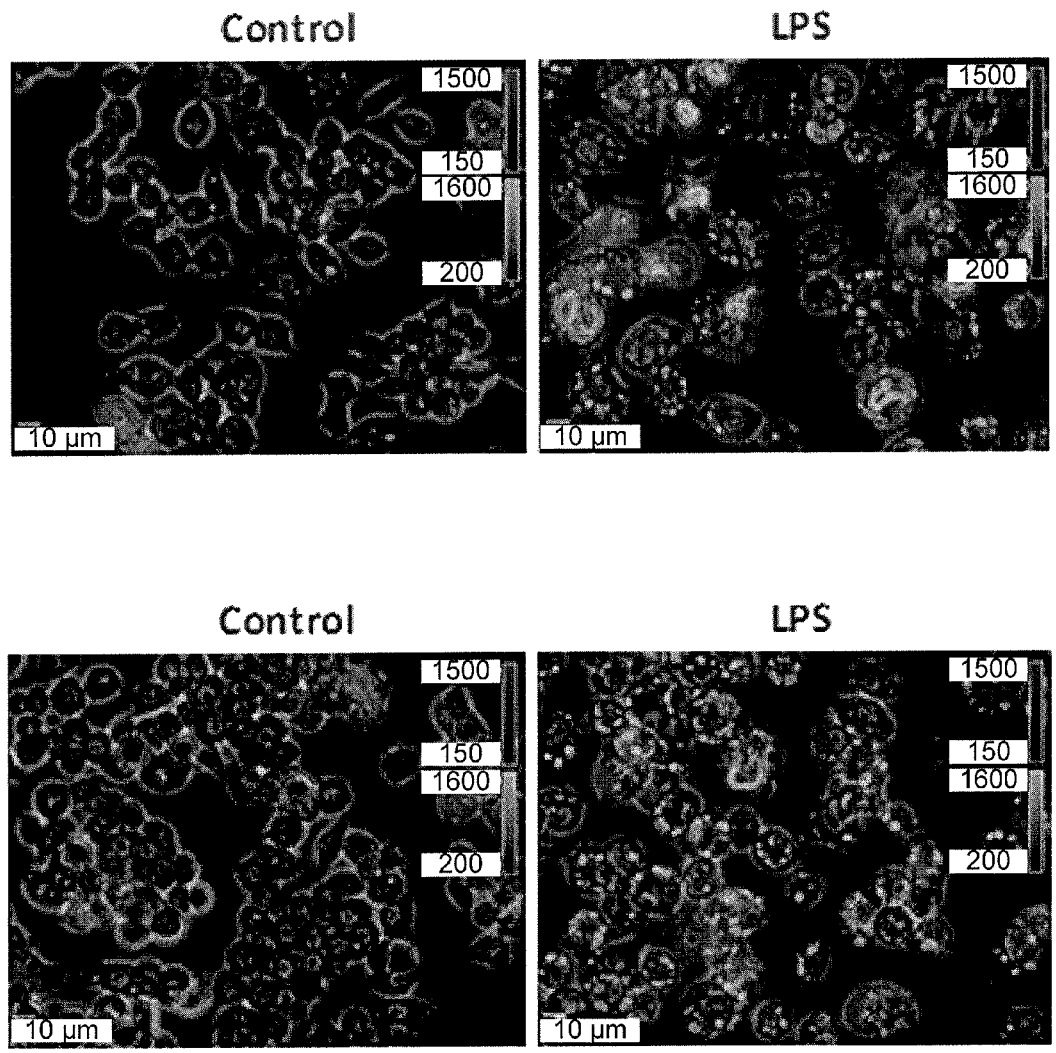
FIG. 8 shows detection of ROS in untreated RAW cells (left panels) and RAW cells treated with lipopolysaccharide endotoxin (LPS; right panels). After LPS treatment, cells were loaded with H-IR680DIOL (10 μM, top panels; 50 μM, bottom panels) and imaged via fluorescence microscopy.

ROS detection in LPS treated RAW cells with H-IR680DIOL. Mouse macrophase cells, RAW 264.7, were treated with lipopolysaccharide endotoxin (LPS; 500 ng/mL) for 24 hrs prior to incubation with H-IR680DIOL (10 or 50 μM) for 30 min. Cells were imaged by fluorescence microscopy, as shown in FIG. 8 (microscope settings: Cy5 (140 ms) (Ex620/60, DC660LP; EM7000/75; Phase (100 ms); 40×).

Figure 9:
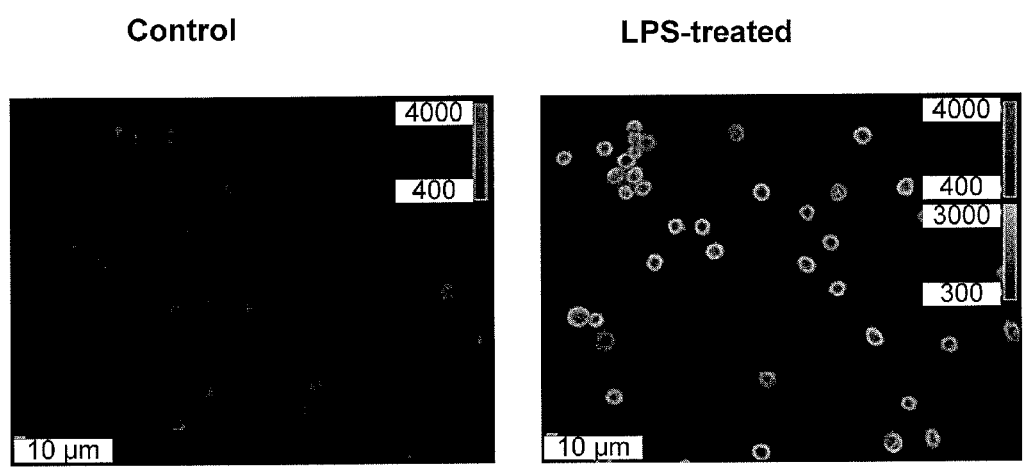
FIG. 9 shows detection of ROS in untreated RAW cells (left panels) and RAW cells treated with lipopolysaccharide endotoxin (LPS; right panels). After LPS treatment, cells were loaded with H-Cy5 and imaged via fluorescence microscopy.

ROS detection in LPS-treated RAW cells with H-Cy5. Mouse macrophase cells, RAW 264.7, were treated with lipopolysaccharide endotoxin (LPS; 500 ng/mL) for 24 hrs prior to incubation with H-IR680DIOL (25 μM) for 30 min. Cells were imaged by fluorescence microscopy, as shown in FIG. 9 (microscope settings: Cy5 (1000 ms) (Ex620/60, DC660LP; EM700/75); Phase (50 ms); 20×).

Figure 10:
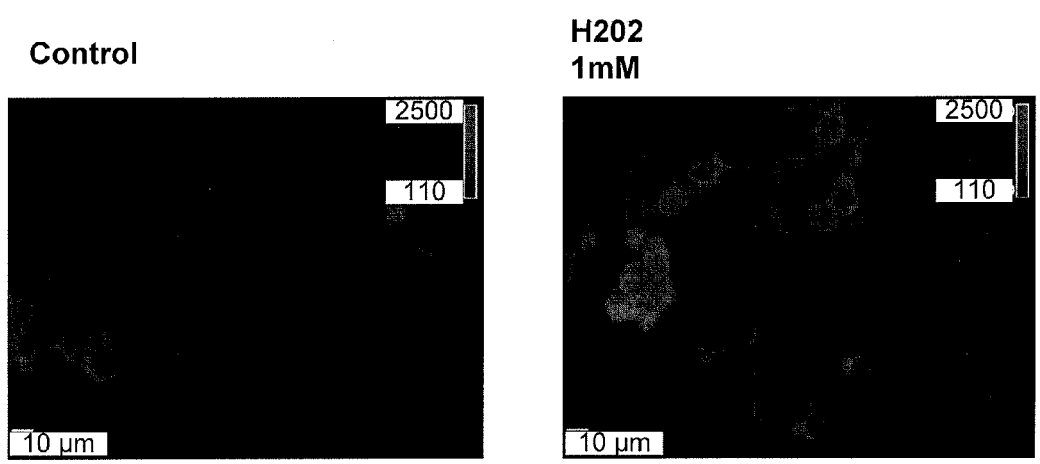
FIG. 10 shows detection of ROS RAW cells treated with varying amounts of hydrogen peroxide (0 mM, top panel; 0.1 mM, middle panel; 1 mM, bottom panel). Cells were loaded with H-IR675 prior to peroxide treatment and imaging via fluorescence microscopy

ROS detection with H-IR675. Microscope setting: Cy6 (Ex620/60, DC660LP; EM700/75); Phase; 40×. Load the dye for 1 hours then treat cells for 30 min. See FIG. 10.

Figure 11:
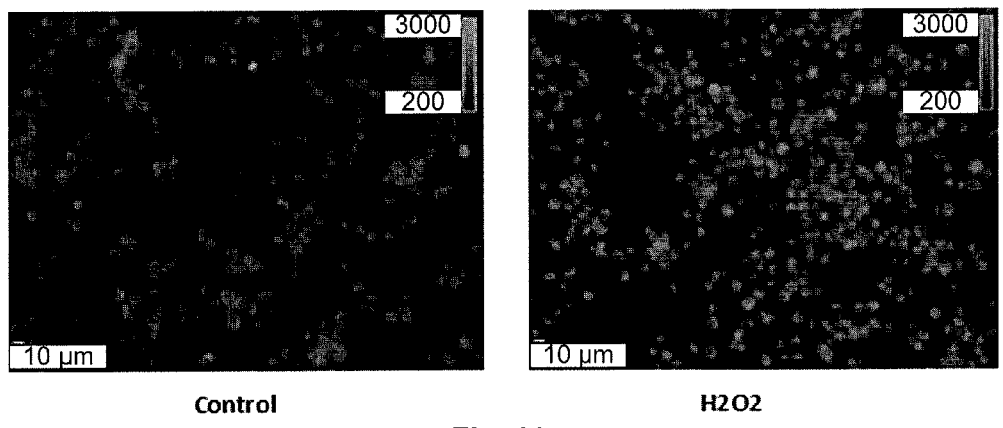
FIG. 11 shows detection of ROS in untreated RAW cells (left panels) and RAW cells treated with hydrogen peroxide (right panels). Cells were loaded with H-Cy3 prior to peroxide treatment and imaging via fluorescence microscopy.

Detection of hydrogen peroxide-induced ROS with H-Cy3. Mouse macrophage cells, RAW 264.7, were incubated with H-Cy3 (50 μM) for 2 hours followed by a 30 minute incubation with H$_2$O$_2$(1 mM). Cells were imaged by fluorescence microscopy using an Olympus IX81 inverted system microscope (20× phase), as shown in FIG. 11.

Figure 12:
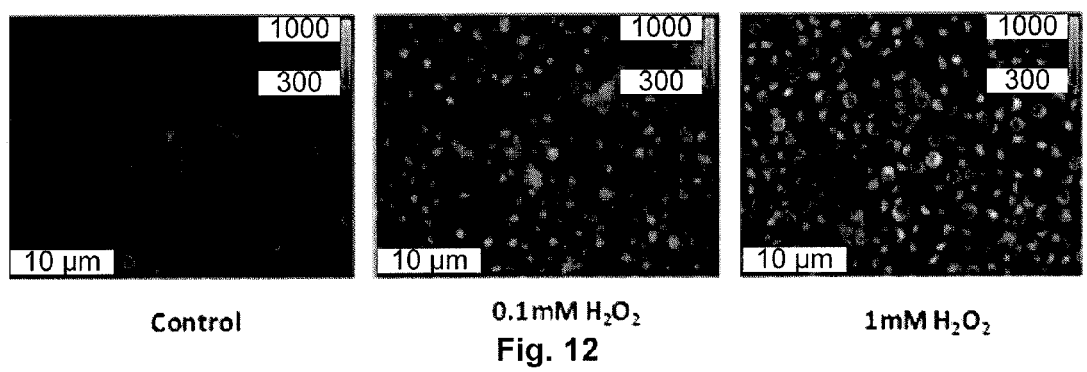
FIG. 12 shows detection of ROS RAW cells treated with varying amounts of hydrogen peroxide (0 mM, left panel; 0.1 mM, center panel; 1 mM, right panel). Cells were loaded with H-IR780F2 prior to peroxide treatment and imaging via fluorescence microscopy.

Detection of hydrogen peroxide-induced ROS with NIR probe H-IR780F2. Mouse macrophase cells, RAW 264.7, were incubated with Hydrocyanine-800 (5 μM) for 1 hour followed by a 30 minute incubation with H$_2$O$_2$. Cells were imaged by fluorescence microscopy using an using an Olympus IX81 inverted system microscope (40× phase), as shown in FIG. 12.

Figure 13:
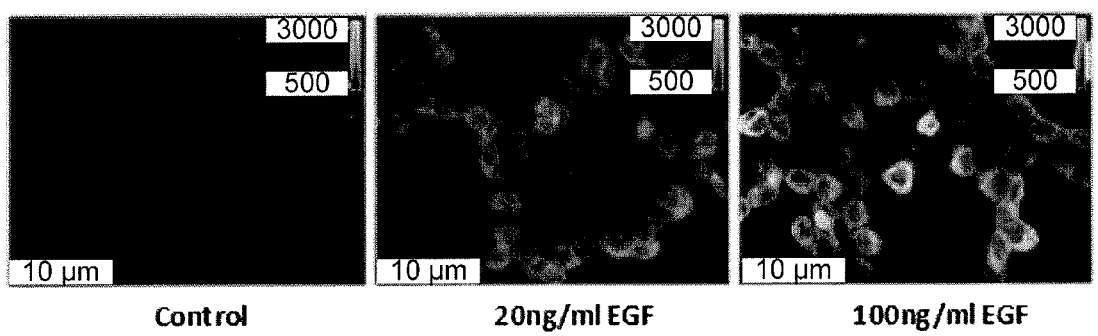
FIG. 13 shows detection of ROS RAW cells treated with varying amounts of epidermal growth factor (EGF; 0 ng/mL, left panel; 20 ng/mL, center panel; 100 ng/mL, right panel). Cells were loaded with H-IR780F2 prior to EGF treatment and imaging via fluorescence microscopy.

Detection of EGF-induced ROS with NIR probe H-IR780F2. Human epithelial carcinoma cells, A431, were incubated with Hydrocyanine-800 (50 uM, shown in green) for 2 hours followed by a 30 minute incubation with EGF. Cells were imaged by fluorescence microscopy using an using an Olympus IX81 inverted system microscope (40× phase), as shown in FIG. 13.

Example 16

In Vivo Analysis

Imaging of Implant-Induced ROS Production

Sterile, endotoxin-free PET disks (8 mm diameter) are implanted subcutaneously following IACUC-approved procedures in 6- to 8-wk-old male BALB/c mice (Jackson Laboratories) anesthetized by isofluorane. A single 1-cm incision is made on the dorsum proximal to the spine, and a subcutaneous pocket laterally spanning the dorsum is created. Sterile disks (two per subject on either side of the spine) are implanted, and the incision is closed using sterile wound clips. Mice undergoing the same surgical procedure but receiving no biomaterial implants are used as sham controls to account for surgery-associated trauma/inflammation.

For bioimaging, 30 μl of H-IRDye® 800CW at a concentration of 1 mg/ml in sterile water is injected near the vicinity of the implant. Thirty minutes after dye injection, the animal is anesthetized and the whole body of the animal is scanned in an IVIS Lumina_bioimaging system (Xenogen). Biofluorescence is integrated using Living Image_software Version 3.1 (Xenogen). ROS bioimaging is performed 30 min after dye injections immediately following surgery/implantation and 1, 4, 7 and 14 days post-surgery/implantation.

H-IRDye 800 CW was also used for imaging.

On days 4 and 8 post-surgery, 50 ml of H-IR780F2 at a concentration of 1.0 mg/ml in saline supplemented with 10% Cremophor EL and 10% DMSO is injected into the jugular vein percutaneously. 10-15 minutes after intravenous dye injections, the animals are scanned immediately in an IVIS Lumina_bioimaging system (Xenogen) and biofluorescence of imaging data sets are acquired and quantified using Living Image_software Version 3.1.

For additional material regarding a procedure, see Selvam et al. In Vivo Imaging of Biomaterial-Associated Inflammation at the Tissue-Implant Interface, Biomaterials, 2011, 32, 7785-7792.

Example 17

Hydrocyanine and Deuterocyanine Dyes as Chemifluorescent Probes for Immunoassays Detection of proteins in a complex biological sample with high sensitivity is playing an increasingly important role in understanding physiological and pathological processes. The low relative abundance of many proteins within a biological sample and the limited quantity of precious sample make sensitive detection of target proteins highly desirable in protein analysis. Chemiluminescence based detection has been the method of choice for the Western blot and ELISA, but the sensitivity of the analysis is compromised as the accumulation of signal intensity is not possible in chemiluminescence. Here, we present a novel near infrared chemifluorescent substrate, where the fluorescence signal will accumulate with each turnover by the HRP enzyme and thus leading unprecedented sensitivity.

Hydrocyanines, such as Hydro-IR780F2 or Deutero-IR780F2 are hydrophobic molecules and will stick to a blotting membrane (e.g., a nitrocellulose membrane), but they are non-fluorescent and will not emit light. Secondary antibody-HRP conjugates bound to protein bands on the membrane will oxidize the hydrocyanine or deuterocyanines to their parent fluorescent cyanine dye structure, however, and consequently the bands will emit fluorescent signals. See FIG. 14. Because of the transient nature of the hydroxyl radical formed by the reaction of hydrogen peroxide and the antibody HRP conjugates, the radicals will oxidize only the hydro/deuterocyanines present in the close proximity to the protein bands on the membrane and, therefore, the fluorescence signals will be compact. Furthermore, the oxidized fluorescent molecules are expected to accumulate with each turn over by the HRP enzyme. The oxidized molecule is also hydrophobic and therefore, is expected to stick to the hydrophobic membrane and hence, the sensitivity is expected to be better than chemiluminescence or secondary antibody detection methods.

In addition to hydro-IR780F2 and deutero-IR780F2, H-Cy5/D-Cy5 ($\lambda_{Ex}$=640, $\lambda_{Em}$=660 nm) and H-Cy7/D-Cy7 ($\lambda_{Ex}$=740, $\lambda_{Em}$=760 nm) can be used for imaging in the NIR range while H-Cy3/D-Cy3 ($\lambda_{Ex}$=540, $\lambda_{Em}$=560 nm) can be used for the visible range.

Use of H-IR780F2 and H-IRDye® 800CW for blot imaging was compared to a commercially-available 680 HRP ELISA substrate (see FIG. 15). 4-12% Bis-Tris gels were loaded with 2-fold, 7-point serial dilutions of A431 lysate (high conc.=2.0 µg), electrophoresed, transferred to Odyssey Nitrocellulose, blocked with SeaBlock Blocking Buffer (with ProClin preservative). The blots were probed with mouse anti-β actin antibodies, followed by HRP goat anti-mouse antibodies (FIG. 15, A-D) or dye-conjugated goat anti-mouse antibodies (FIG. 15, E-F). Blots probed with HRP goat anti-mouse antibodies were incubated for 5 min with chemifluorescent substrates in buffer containing hydrogen peroxide. H-IRDye® 800CW and H-IR780F2 were tested at 10 µM with 50-200 µM $H_2O_2$. HRP 680 ELISA substrate was used according to published protocols (i.e., LI-COR product no. 926-34300).

Observations: H-IRDye® 800CW substrate gave a "negative" signal with high background (FIG. 15A-B). H-IR780F2 resulted in good signal with high linearity for lower signals and moderate linearity for higher signals (FIG. 15C).

Figure 16A:
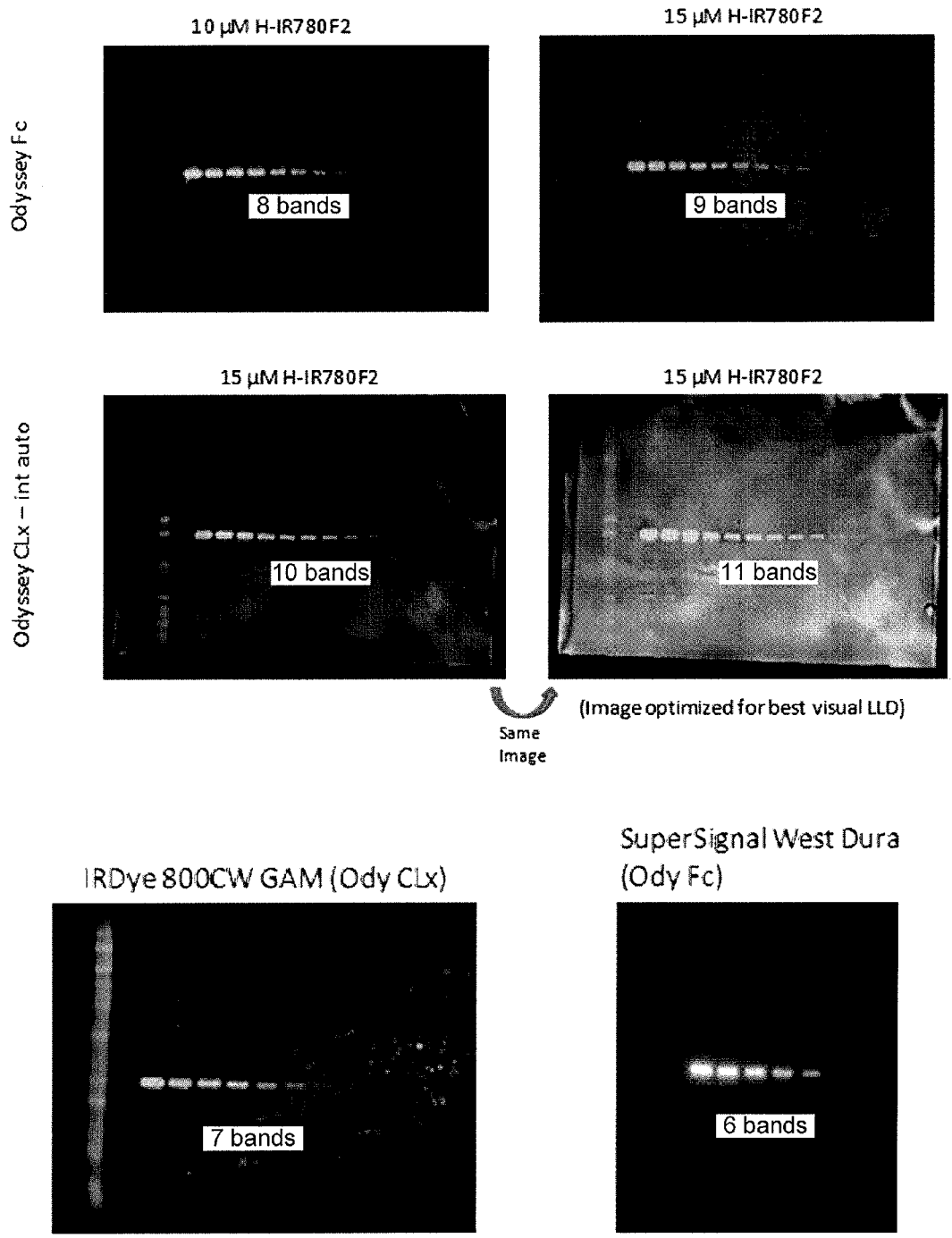
FIG. 16 A-B show the immunoassay analysis of biological samples using (FIG. 16A) chemifluorescent substrate H-IR780F2 (top and middle panels), as compared to fluroscently-labeled antibodies (bottom left panel) and chemiluminescent reagents (bottom right panel)
(FIG. 16B) shows a quantitative comparison of two duplicate Western blots using H-IR780F2 (B=red and D=blue).
Figure 16B:
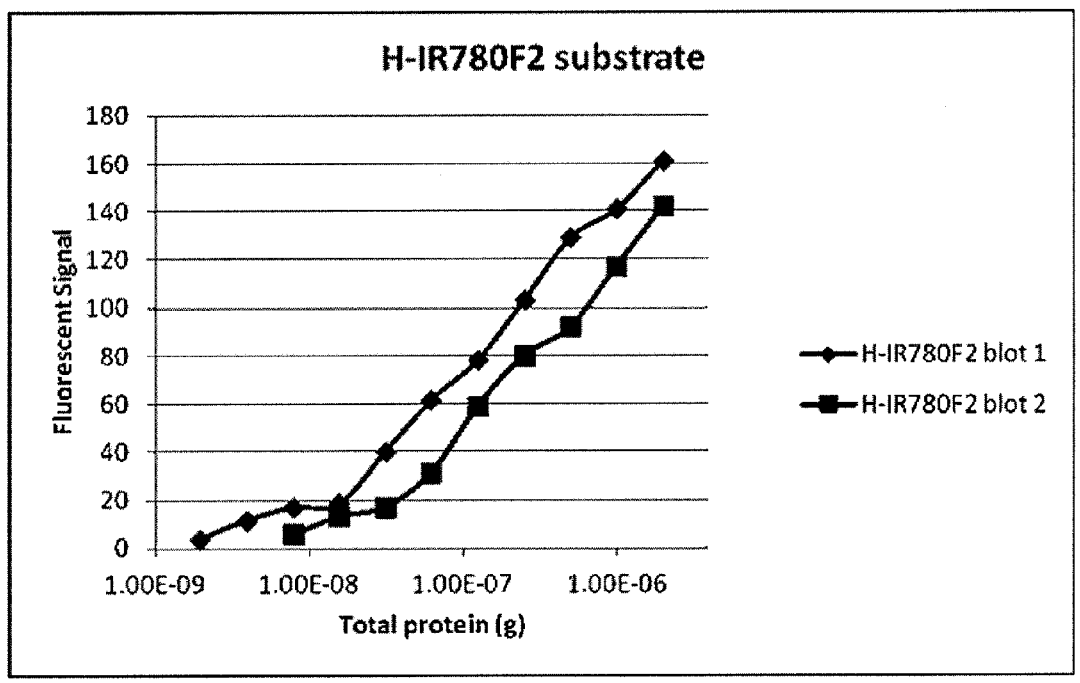

The chemifluorescent substrate H-IR780F2 (FIG. 16A-D) exhibits 32-fold sensitivity compared to chemiluminescent detection (using a luminol-based reagent system; FIG. 16D), and 16-fold sensitivity compared to fluorescent dye-conjugated secondary antibody detection in Western blots (FIG. 16E). Detection data for various probes is summarized in Table 2. The basic workflow remains unchanged and therefore, the chemifluorescent substrate based analysis is amenable to other methods of protein analysis, such as ELISAs and protein arrays.

TABLE 2

Detection Limits for Luminescent/Fluorescent Probes

| Detection Substrate | Signal Type | Lower Limit of Detection (LLD) |
|---|---|---|
| SuperSignal West Dura (Thermo Scientific) | chemiluminescence | 62.5 ng |
| IRDye 800CW-goat anti-mouse conjugate | fluorescence | 31.3 ng |
| H-IR780F2 | chemifluorescence | 1.5 ng |

Example 18

Ratiometric Probe Hydrocyanine-560-Bodipy Probe

The ratiometric probe is synthesized by starting with cyanine-660:2EG and converting it to a mixed carbonate by treating with N,N'-Disuccinimidyl carbonate and diisopropylethyl amine (DIPEA). The mixed carbonate upon treatment with commercially available BODIPY Dye amine forms cyanine-660:2EG-BODIPY. Reduction of cyanine-660:2EG-BODIPY with sodium borohydride selectively reduces the imminium cation of the cyanine dye fragment leading to the corresponding ratiometric hydrocyanine probe (below). The excitation and emission wavelengths of the BODIPY dye and the cyanine-660 dye do not overlap.

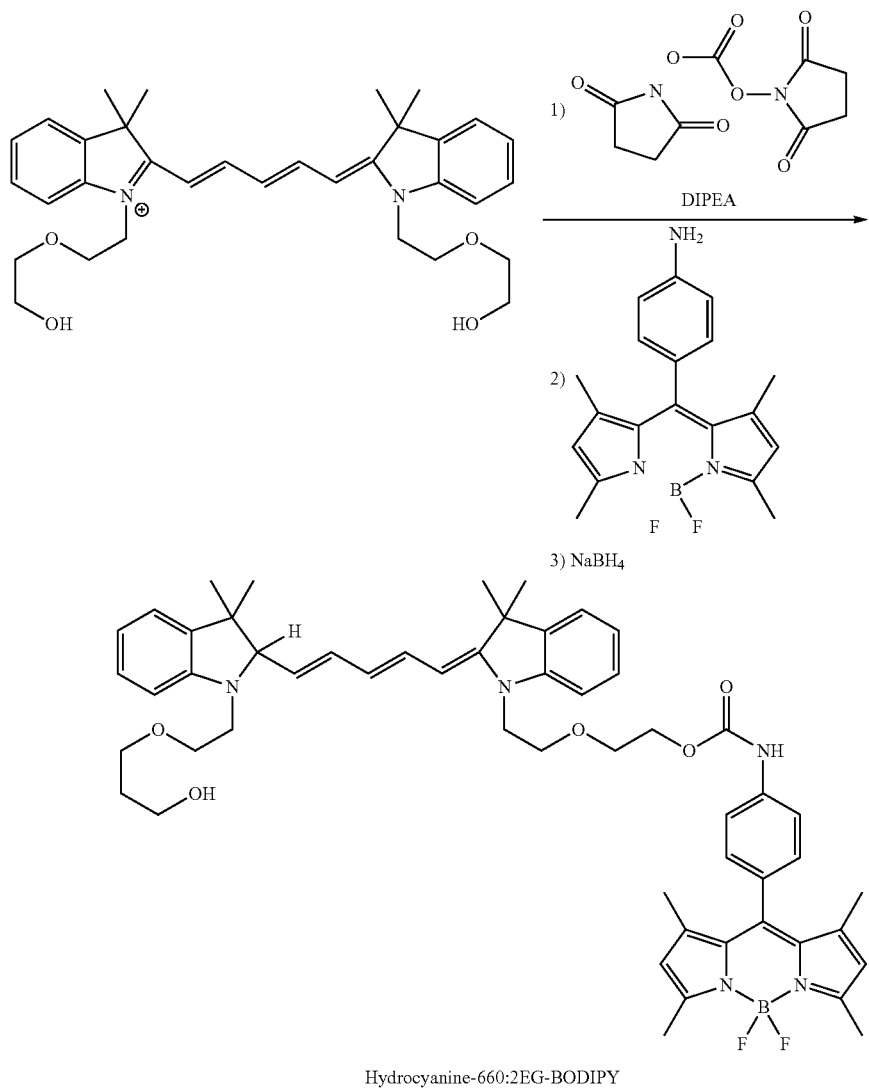

Hydrocyanine-660:2EG-BODIPY

Synthesis of Ratiometric Hydrocyanine-660:2EG-BODIPY

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having Formula I:

I

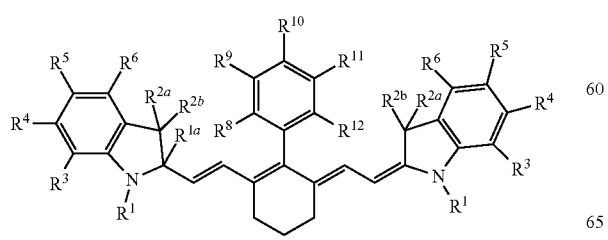

wherein
each $R^1$ is an independently selected alkyl group that is additionally substituted with from 0 to 1 $R^{14}$ and from 0 to 1 -L-Y—Z; wherein the alkyl is optionally interrupted by at least one heteroatom or an ionic group;

$R^{1a}$ is either hydrogen or deuterium;

each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 -L-Y—Z;

each $R^3$, $R^4$, $R^5$, and $R^6$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 -L-Y—Z;

$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein at least one member selected from the group consisting of $R^8$, $R^9$, and $R^{10}$ is halo;

each $R^{13}$ is a member independently selected from the group consisting of hydroxyl, amino, carboxyl, and alkoxycarbonyl;

each $R^{14}$ is a member independently selected from the group consisting of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the alkyl or alkenyl is additionally substituted with from 0 to 1 $R^{13}$ and from 0 to 1 -L-Y—Z;

each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;

each Y is an optional member independently selected from the group consisting of a bond, —O—, —S—, —NH—, —NHC(O)—, —C(O)NH—, —$NR^{15}$—, —$NR^{15}$C(O)—, —C(O)$NR^{15}$—, —N(Z)—, —N(Z)C(O)—, and —C(O)N(Z)—;

each Z is independently selected from the group consisting of -L-$R^{13}$ and -L-$R^{16}$;

or alternatively, —Y—Z is a member selected from the group consisting of —N($Z^1$)$_2$, —N($Z^1$)C(O)$Z^1$, and —C(O)N($Z^1$)$_2$, and the two $Z^1$ groups are linked to form a cycloalkynyl group;

each $R^{15}$ is a member independently selected from the group consisting of alkyl and alkoxycarbonylalkyl; wherein the alkyl is optionally interrupted by at least one heteroatom;

each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, cycloalkynyl, spirocycloalkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester; and wherein said compound has a balanced charge.

2. The compound of claim 1, wherein each $R^{16}$ is independently a member selected from the group consisting of activated acyl, acrylamido, optionally substituted alkylsulfonate ester, azido, optionally substituted arylsulfonate ester, amino, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, and vinyl sulfonyl.

3. The compound of claim 1, wherein at least one $R^{16}$ is a member independently selected from the group consisting of azido, alkynyl, cycloalkynyl, a pegylated azido, a pegylated alkynyl, a pegylated cycloalkynyl, and an o-diarylphosphino aryl ester.

4. The compound of claim 1, wherein at least one member selected from the group consisting of $R^8$, $R^9$, and $R^{10}$ is chloro or fluoro.

5. The compound of claim 4, wherein at least one member selected from the group consisting of $R^8$, $R^9$, and $R^{10}$ is fluoro.

6. The compound of claim 4, wherein at least one member selected from the group consisting of $R^8$, $R^9$, and $R^{10}$ is chloro.

7. The compound of claim 1, wherein each $R^3$, $R^4$, $R^5$, and $R^6$ is a member independently selected from the group consisting of hydrogen, alkyl, alkenyl, halo, alkoxy, cyano, carboxyl, alkoxycarbonyl, amido, sulfonato, alkoxyalkyl, carboxyalkyl, alkoxycarbonylalkyl, and sulfonatoalkyl.

8. The compound of claim 1, wherein $R^1$ is $(CH_2)_rSO_3H$ or $(CH_2)_rSO_3^-$; and wherein r is an integer from 1 to 20.

9. The compound of claim 8, wherein r is 2, 3, or 4.

10. The compound of claim 1, wherein $R^{2a}$ and $R^{2b}$ are methyl.

11. The compound of claim 1, wherein $R^8$, $R^9$, or $R^{10}$ is -L-Y—Z.

12. The compound of claim 1, having the formula:

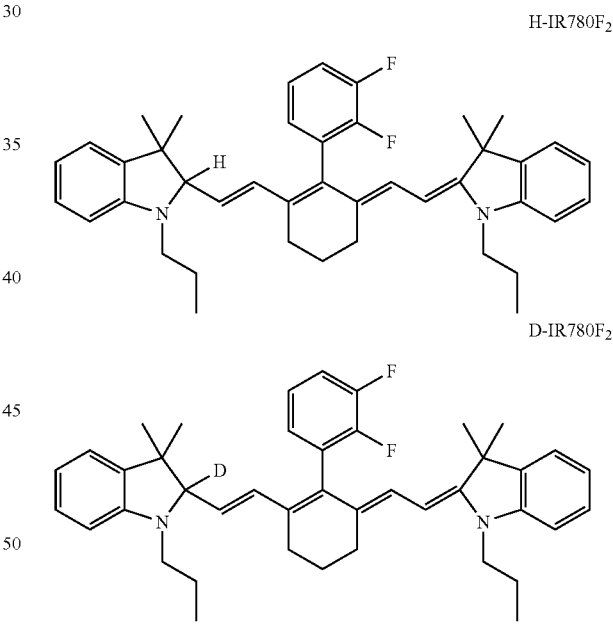

13. The compound of claim 1, wherein the cycloalkynyl group is a member selected from the group consisting of cyclopentynyl, cyclohexynyl, cyclooctynyl, and dibenzocyclooctynyl (DBCO).

* * * * *